US011358955B2

United States Patent
Cai et al.

(10) Patent No.: US 11,358,955 B2
(45) Date of Patent: *Jun. 14, 2022

(54) 1-(ARYLMETHYL)QUINAZOLINE-2,4(1H,3H)-DIONES AS PARP INHIBITORS AND THE USE THEREOF

(71) Applicant: IMPACT Therapeutics, Inc., Jiangsu (CN)

(72) Inventors: Sui Xiong Cai, Jiangsu (CN); Ye Edward Tian, Jiangsu (CN); Haijun Dong, Shanghai (CN); Qingbing Xu, Jiangsu (CN); Lizhen Wu, Jiangsu (CN); Lijun Liu, Jiangsu (CN); Yangzhen Jiang, Jiangsu (CN); Qingli Bao, Jiangsu (CN); Guoxiang Wang, Jiangsu (CN); Feng Yin, Jiangsu (CN); Chengyun Gu, Jiangsu (CN); Xiuhua Hu, Jiangsu (CN); Xiaozhu Wang, Jiangsu (CN); Sishun Kang, Jiangsu (CN); Shengzhi Chen, Jiangsu (CN)

(73) Assignee: IMPACT THERAPEUTICS, INC., Nanjing (CN)

( * ) Notice: Subject to any disclaimer, the term of this patent is extended or adjusted under 35 U.S.C. 154(b) by 114 days.

This patent is subject to a terminal disclaimer.

(21) Appl. No.: 16/415,803

(22) Filed: May 17, 2019

(65) Prior Publication Data

US 2019/0270732 A1 Sep. 5, 2019

Related U.S. Application Data

(63) Continuation of application No. 15/935,694, filed on Mar. 26, 2018, now Pat. No. 10,316,027, which is a continuation of application No. 15/042,366, filed on Feb. 12, 2016, now Pat. No. 9,926,304, which is a continuation of application No. 14/006,722, filed as
(Continued)

(30) Foreign Application Priority Data

Apr. 1, 2011 (CN) .......................... 201110082475.6
Jul. 11, 2011 (WO) ................ PCT/CN2011/077034

(51) Int. Cl.
| | |
|---|---|
| C07D 409/12 | (2006.01) |
| A61K 31/517 | (2006.01) |
| C07D 401/06 | (2006.01) |
| C07D 239/96 | (2006.01) |
| A61K 45/06 | (2006.01) |
| C07D 401/12 | (2006.01) |
| C07D 403/12 | (2006.01) |
| C07D 405/12 | (2006.01) |
| C07D 413/12 | (2006.01) |
| C07D 417/12 | (2006.01) |
| C07D 471/04 | (2006.01) |
| C07D 487/04 | (2006.01) |

(52) U.S. Cl.
CPC .......... *C07D 409/12* (2013.01); *A61K 31/517* (2013.01); *A61K 45/06* (2013.01); *C07D 239/96* (2013.01); *C07D 401/06* (2013.01); *C07D 401/12* (2013.01); *C07D 403/12* (2013.01); *C07D 405/12* (2013.01); *C07D 413/12* (2013.01); *C07D 417/12* (2013.01); *C07D 471/04* (2013.01); *C07D 487/04* (2013.01)

(58) Field of Classification Search
CPC ........................... C07D 409/12; A61K 31/517
See application file for complete search history.

(56) References Cited

U.S. PATENT DOCUMENTS

| | | | |
|---|---|---|---|
| 4,405,623 | A | 9/1983 | Ishikawa et al. |
| 4,797,403 | A | 1/1989 | Lowe, III |
| 6,201,121 | B1 | 3/2001 | Kamiya et al. |

(Continued)

FOREIGN PATENT DOCUMENTS

| | | |
|---|---|---|
| CN | 1980913 A | 6/2007 |
| DE | 26 52 144 A1 | 5/1978 |

(Continued)

OTHER PUBLICATIONS

Rouleau et al. (Nature Reviews (2010), vol. 10, pp. 293-301) (Year: 2010).*

(Continued)

*Primary Examiner* — Yong S. Chong
(74) *Attorney, Agent, or Firm* — Sterne, Kessler, Goldstein & Fox P.L.L.C.

(57) ABSTRACT

Disclosed are 1-(arylmethyl)quinazoline-2,4(1H,3H)-diones represented by the Formula (I):

(I)

wherein Ar, $R_1$-$R_6$ are defined herein. Compounds having Formula (I) are PARP inhibitors. Therefore, compounds of the invention may be used to treat clinical conditions that are responsive to the inhibition of PARP activity.

22 Claims, No Drawings

Related U.S. Application Data application No. PCT/CN2012/073362 on Mar. 31, 2012, now Pat. No. 9,290,460.

(56) References Cited

U.S. PATENT DOCUMENTS

| | | | |
|---|---|---|---|
| 6,344,559 | B1 | 2/2002 | Omori et al. |
| 9,090,568 | B2 | 7/2015 | Liu et al. |
| 9,926,304 | B2 | 3/2018 | Cai et al. |
| 2005/0159431 | A1 | 7/2005 | Albrecht et al. |
| 2008/0039480 | A1 | 2/2008 | Kennis et al. |
| 2014/0018376 | A1 | 1/2014 | Allgeier et al. |
| 2014/0023642 | A1 | 1/2014 | Cai et al. |
| 2014/0031358 | A1 | 1/2014 | Liu et al. |
| 2016/0237070 | A1 | 8/2016 | Cai et al. |

FOREIGN PATENT DOCUMENTS

| | | |
|---|---|---|
| EP | 0 795 548 A1 | 9/1997 |
| JP | 10-195058 A | 7/1998 |
| JP | 2001-302515 A | 10/2001 |
| JP | 2002-284699 A | 10/2002 |
| JP | 2007-137818 A | 6/2007 |
| WO | WO 98/27975 A1 | 7/1998 |
| WO | WO 02/102793 A2 | 12/2002 |
| WO | WO 2006/003148 A1 | 1/2006 |
| WO | WO 2008/150470 A1 | 12/2008 |
| WO | WO 2009/027730 A1 | 3/2009 |
| WO | WO 2009/118384 A1 | 10/2009 |
| WO | WO 2012/125521 A1 | 9/2012 |

OTHER PUBLICATIONS

International Search Report for PCT/CN2012/073362, dated Jul. 12, 2012, The State Intellectual Property Office, Beijing, People's Republic of China.
Ame, J.-C. et al., "The PARP superfamily," *BioEssays* 26:882-893, Wiley Periodicals, Inc. (2004).
Audeh, M.W. et al., "Oral poly (ADP-ribose) polymerase inhibitor olaparib inpatients with *BRCA1*or *BRCA2* mutations and recurrent ovarian cancer: a proof-of-concept trial," *Lancet* 376:245-251, Lancet Publishing Group (Jul. 24, 2010).
Berge, S.M. et al., "Pharmaceutical Salts," *J. Pharm. Sci.* 66:1-20, American Pharmaceutical Association (1977).
Bryant, H.E. et al., "Specific killing of BRCA2-deficient tumours with inhibitors of poly(ADP-ribose) polymerase," *Nat.* 434:913-917, Nature Publishing Group (2005).
Bundgaard, H., "(C) Means to Enhance Penetration, (1) Prodrugs as a means to improve the delivery of peptide drugs" *Adv. Drug Delivery Rev.* 8:1-38, Elsevier Science Publishers B.V. (1992).
Cho, A., "Recent Advances in Oral Prodrug Discovery," *Ann. Rep. Med. Chem.* 41:396-407, Elsevier Inc. (2006).
Chou, T.-C., "Theoretical Basis, Experimental Design, and Computerized Simulation of Synergism and Antagonism in Drug Combination Studies," *Pharmacol. Rev.* 58:621-681, The American Society for Pharmacology and Experimental Therapeutics (2006).
Dantzer, F. et al., "Base Excision Repair is Impaired in Mammalian Cells Lacking Poly(ADP-ribose) Polymerase-1," *Biochem.* 39:7559-7569, American Chemical Society (2000).
DeMurcia, J.M. et al., "Requirement of poly(ADP-ribose) polymerase in recovery from DNA damage in mice and in cells," *PNAS USA* 94:7303-7307, The National Academy of Sciences (1997).
Farmer, H. et al., "Targeting the DAN repair defect in *BRCA* mutant cells as a therapeutic strategy," *Nat.* 434:917-921, Nature Publishing Group (2005).
Hirai, S. et al., "Metabolites of Febrifugine and Its Synthetic Analogue by Mouse Liver S9 and Their Antimalarial Activity Against *Plasmodium*Malaria Parasite," *J. Med. Chem.* 46:4351-4359, American Chemical Society (2003).
Jagtop, P. and Szabó, C., "Poly(ADP-ribose) Polymerase and the Therapeutic Effects of Its Inhibitors," *Nat. Rev. Drug Disc.* 4:421-440, Nature Publishing Group (2005).
Kraus, W.L. and Lis, J.T., "PARP Goes Transcription," *Cell* 113:677-683, Cell Press (2003).
Leonard, F. et al., "Unnatural Amino Acids. II. Congeners of dl-3-Carboxy-4-methoxyphenylalanine," *J. Med. Chem.* 478-481, American Chemical Society (1967).
McMahon, G., "VEGF Receptor Signaling in Tumor Angiogenesis," *The Oncologist* 5(Suppl.1):3-10, AlphaMed Press (2000).
O'Shaughnessy, J. et al., "Iniparib plus Chemotherapy in Metastatic Triple-Negative Breast Cancer," *N. Engl. J. Med.* 364:205-214, Massachusetts Medical Society (Jan. 20, 2011).
Pal, S.K. and Mortimer, J., "Triple-negative breast cancer; Novel therapies and new directions," *Maturitas* 63:269-274, Elsevier Ireland Ltd. (2009).
Pinedo, H.M. and Slamon, D.J., "Translational Research: The Role of VEGF in Tumor Angiogensis," *The Oncologist* 5(Suppl. 1):1-2, AlphaMed Press (2000).
Plummer, R. et al., "Phase I Study of the Poly(ADP-Ribose) Polymerase Inhibitor, AG014699, in Combination with Temozolomide in Patients with Advanced Solid Tumors," *Clin. Cancer Res.* 74:7917-7923, American Association for Cancer Research (2008).
Skaper, S.D., "Poly(ADP-Ribose) Polymerase-1 in Acute Neuronal Death and Inflammation," *Ann. N.Y. Acad. Sci.* 993:217-228, New York Academy of Sciences (2003).
Skaper, S., "Questions and Answers Session VI: Mechanisms of Neuroprotection," *Ann. N.Y. Acad. Sci.* 993:287-288, New York Academy of Sciences (2003).
Szabó, G. et al., "Poly(ADP-ribose) polymerase activation in the reperfused myocardium," *Cardiovascular Res.* 67:471-480, Elsevier B.V. (2004).
Tutt, A. et al., "Oral poly(ADP-ribose) polymerase inhibitor olaparib in patients with *BRCA1* or *BCRA2* mutations and advanced breast cancer: a proof-of-concept trial," *Lancet* 576:235-244, Lancet Publishing Group (Jul. 24, 2010).
Wooster, R.W. and Weber, B.L., "Breast and Ovarian Cancer," *N. Engl. J. Med.* 348:2339-2347, Massachusetts Medical Society (2003).
Wuts, P.G.M. and Greene, T.W., "Protection for the Amino Group," *Greene's Protective Groups in Organic Sysnthesis*, Fourth ed., 11 pages, John Wiley & Sons, Inc. (2007).
Wuts, P.G.M. and Greene, T.W., "Protection for the Hydroxyl Group, Including 1,2- and 1,3-Diols," *Greene's Protective Groups in Organic Synthesis*, Fourth ed., 9 pages, John Wiley & Sons, Inc. (2007).
International Search report for International Patent Appl. No. PCT/US2012/028698, U.S. Patent and Trademark Office, Alexandria, VA, dated Jul. 5, 2012.
Office Action for U.S. Appl. No. 14/004,633, § 371(c) Date Oct. 17, 2013, Inventors: Liu et al., U.S. Patent and Trademark Office, Alexandria, VA, dated Jun. 3, 2014.
Menear, K.A. et al., "4-[3-(4-Cyclopropanecarbonylpiperazine-1-carbonyl)-4-fluorobenzyl]-2H-phthalazin-1-one: A Novel Bioavailable Inhibitor of Poly(ADP-ribose) Polymerase-1," *J. Med. Chem.* 51:6581-6591, American Chemical Society (2008).
English language machine translation of the claims of DE 26 52 144 A1 (document FP2).
English language machine translation of the claims of JP 10-195058 A (document FP9).
English language machine translation of the claims of JP 2001-302515A (document FP3).
English language machine translation of the claims of JP 2002-284699A (document FP4).
English language machine translation of the claims of JP 2007-137818A (document FP5).
Office Action for U.S. Appl. No. 14/004,633, § 371(c) Date Oct. 17, 2013, Inventors: Liu et al., U.S. Patent and Trademark Office, Alexandria, VA, dated Dec. 22, 2014.
Goto, S., et al., "The Process Development of a Novel Aldose Reductase Inhibitor, FK366. Part 1. Improvement of Discovery Process and New Syntheses of 1-Substituted Quinazolinediones," *Organic Process Research & Development* 7:700-706, American Chemical Society, United States (2003).

(56) References Cited

OTHER PUBLICATIONS

Mitsos, C., "Isosteres in Medicinal Chemistry," Group Meeting Feb. 1, 2006, 7 pages.

Lord, C.J. et al., "Targeted therapy for cancer using PARP inhibitors," Current Opinion in Pharmacology 8:363-369, Elsevier, Netherlands (2008).

Vogelstein, B. et al., "Cancer Genes and the Pathways They Control," Nature Medicine 10(8):789-799, Nature Publishing Group, England (2004).

He, J. et al., "Poly(ADP-ribose) polymerase inhibitors as promising cancer therapeutics," Acta Pharmacologica Sinica 31: 1172-1180, Nature Publishing Group, England (2010).

Chalmers, A. J., "The Potential role and application of PARP inhibitors in cancer treatment," British Medical Bulletin 89:23-40, Oxford University Press, England (2009).

Audeh, M.W., et al., "Phase II trial of the oral PARP inhibitor olaparib (AZD2281) in BRCA-deficient advanced ovarian cancer," J. Clinical Oncology 27:5500-5500, American Society of Clinical Oncology, United States) (2009).

Ferraris, D.V., et al., " Evolution of Poly(ADP-ribose) Polymerase-1 (PARP-1) Inhibitors, From Concept to Clinic," J Med Chem 53:4561-4584, American Chemical Society, United States (2010).

Chan, Y.C. et al., "PARP Inhibitors in Cancer Diagnosis and Therapy," *Clin. Cancer Res*. 27:1585-1594, American Association for Cancer Research, United States (2020).

Chen, A. "PARK inhibitors: its role in treatment of cancer," *Chin. J. Cancer* 30:463-471, Chinese Anti-Cancer Association, China (2011).

Farago, A.F. et al., "Phase 1/2 study of olaparib tablets and temozolomide in patients with small cell lung cancer (SCLC) following failure of prior chemotherapy," AACR Annual Meeting, Apr. 1-5, 2017, Abstract No. CT048, Washington, DC, United States.

Liu, J.F. et al., "Overall survival and updated progression-free survival outcomes in a randomized phase II study of combination cediranib and olaparib versus olaparib in relapsed platinum-sensitive ovarian cancer," *Ann. Oncol*. 30:551-557, Oxford University Press, United Kingdom (2019).

\* cited by examiner

1-(ARYLMETHYL)QUINAZOLINE-2,4(1H,3H)-DIONES AS PARP INHIBITORS AND THE USE THEREOF

BACKGROUND OF THE INVENTION

Field of the Invention

This invention is in the field of medicinal chemistry. In particular, the invention relates to 1-(arylmethyl)quinazoline-2,4(1H,3H)-diones, and the use of these compounds as PARP inhibitors and anti-cancer drugs.

RELATED ART

Poly (ADP-ribose) polymerase (PARP) catalyzes the addition of poly (ADP-ribose) to the target protein using NAD+ that is an important process in DNA repair. This is an essential process for maintaining DNA and chromosome integrity and stability, and for ensuring the survival of mammalian cells. PARP-1 catalyzes the majority of the intracellular ADP-ribose polymerization reactions, although PARP-2 and other subtypes also have this function. The PARP-1 knockout mice do not have the repair function for single-stranded DNA damages (Krishnakumar and Kraus, 2010, Molecular Cell 39:8). Cancer cells with DNA repair defects, such as BRCA1 (breast cancer 1) or BRCA2 (breast cancer 2) deficiency, are particularly sensitive to DNA damaging anticancer agents, including platinum chemotherapy drugs, DNA methylation anticancer drugs and DNA topoisomerase inhibitors, or radiation therapy. Phase II clinical trial data have shown that PARP-1 inhibitor olaparib (AZD2281) was effective for the treatment of advanced breast cancer (Andrew Tutt et al., 2009, J. Clin. Oncol. 27:18 s; Andrew Tutt et al., 2010 Lancet 376:235; R A Dent et al., 2010 J. Clin. Oncol. 28:15 s). These scientific and clinical results demonstrated that PARP-1 inhibitors may be used as effective anti-cancer drugs to treat a variety of cancers. The applications of PARP-1 inhibitors for the treatment of cancer are mainly based on two mechanisms. First, because of the rapid growth. DNA replication is much higher in cancer cells than in normal cells. Drugs that cause DNA damage will induce cancer cell death selectively. However, due to the presence of DNA repair enzymes such as PARP-1, the therapeutic effects of these drugs can not be fully materialized. By inhibiting the DNA repair mechanism, PARP-1 inhibitors in combination with commonly used DNA damaging anti-cancer drugs, such as temozolomide, can achieve synergy effects and greatly enhance the anticancer effects of currently used anticancer drugs. Second, for cancer cells with DNA repair deficiency, such as BRCA1 or BRCA2 deficient triple-negative breast cancer, PARP-1 inhibitors can directly kill the cancer cells and function as anticancer drugs independently. According to statistics, about 10-15% of breast cancer patients have family history of genetic factors, in which the BRCA1 or BRCA2 gene mutations account for 15-20% of all hereditary breast cancers. Since PARP-1 is involved in DNA repair, utilization of PARP-1 inhibitors to inhibit DNA repair may be an effective and selective treatment for cancers with DNA repair genetic defect, including triple-negative breast cancers. Furthermore, PARP-1 inhibitors may also be used to treat diseases due to excessive cell death, including central nervous system diseases such as stroke and neurodegenerative diseases (Akinori Iwashita et al., 2004, J. Pharmacol. Exp. Thera. 310: 425).

The inhibitory activity of PARP-1 inhibitors can be measured by directly using PARP-1 enzymes. In addition, since PARP-1 inhibitors can increase the cytotoxicity of DNA damaging anti-cancer drugs such as methyl mathanesulfonate (MMS) on cancer cells, the activity of PARP-1 inhibitors can also be determined by measuring cell viability, such as using a MTT assay, in the presence of MMS and PARP-1 inhibitors. Furthermore, Cancer cells with deficiency in DNA repair, such as in the case of BRCA1 or BRCA2 deficient triple-negative breast cancer, can be killed by PARP-1 inhibitors alone. Therefore the anticancer activity of PARP-1 inhibitors can be determined by measuring the inhibitory effect of these compounds on cell growth of BRCA-2 deficient CAPAN-1 human pancreatic cancer cells.

It has been known that many cancer chemotherapeutic drugs trigger cancer cells to undergo apoptosis. The mechanism of apoptosis involves a cascade of initiator and effector caspases that are activated sequentially. Caspases are a family of cysteine proteases that require aspartic acid residues at the 1 position of substrates for efficient cleavage. Among these caspases, caspase-3, 6, and 7 are key effector caspases that cleave multiple protein substrates in cells, leading to cell death. Cellular caspase activity can be determined using caspase substrates and used as a measurement of cell apoptosis. PARP-1 inhibitors can increase the apoptosis-inducing activity of many DNA damaging anticancer drugs such as MMS. Therefore, the activity of PARP-1 inhibitors can be determined via measuring the intracellular caspase activity of cancer cells treated with DNA damaging anticancer drugs in combination with PARP-1.

JP2007137818 disclosed the preparation of 8-hydroxyquinazoline-2,4(1H,3H)-dione derivatives as poly(ADP-ribose) polymerase (PARP) inhibitors, wherein X=$(CH_2)_n$; n=an integer of 1-4; Y=H, $NR_1R_2$, 1,2,3,4-tetrahydroisoquinolyl, decahydroisoquinolyl, 1,3-dioxo-1,3-dihydro-2H-isoindolyl, 3-oxo-3,4-dihydrobenz[1,4]oxazinyl, pyridyl, benzyl, (un)substituted optionally fused 5-membered N-heterocyclyl and (un)substituted aryloxy, etc.

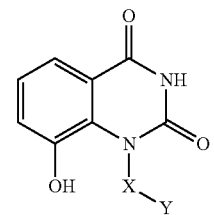

WO2006003148 disclosed the preparation of quinazolinedione derivatives as PARP inhibitors for the treatment of PARP mediated diseases, wherein X and Y are each independently N or CH; $L_1$=a bond or alkylene; $L_2$=a bond, CO, alkylene, CO-alkylene, etc.; $R_1$=H or OH; Z=H or (un)substituted (hetero)aryl; etc.

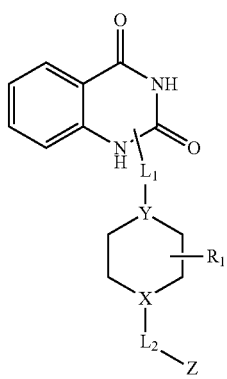

SUMMARY OF THE INVENTION

The invention provides novel 1-(arylmethyl)quinazoline-2,4(1H,3H)-diones, as represented in Formulae I, II and III. These compounds have PARP inhibitory activities.

The present invention also provides pharmaceutical compositions comprising a compound of Formula I, II or III in an effective amount for the treatment of cancer.

The invention also provides a pharmaceutical composition useful for the treatment of cancer, containing an effective amount of a compound of one of the Formula I, II or III in admixture with one or more pharmaceutical acceptable carriers or diluents.

The invention also provides a pharmaceutical composition useful for the treatment of cancer, containing an effective amount of a compound of one of the Formula I, II or III, in combination with one known anticancer drugs or its pharmaceutically acceptable salts.

The invention also is directed to methods for the preparation of novel compounds of Formulae I, II and III.

DETAILED DESCRIPTION OF THE INVENTION

The novel and potent PARP inhibitors of the present invention include 1-(arylmethyl)quinazoline-2,4(1H,3H)-diones, as represented in Formulae I, II and III.

Specifically, compounds of the present invention are represented by Formula I:

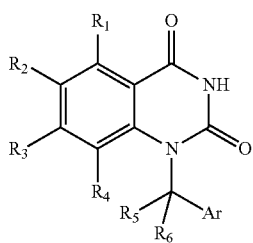

(I)

or pharmaceutically acceptable salts or prodrugs thereof, wherein:

Ar is an optionally substituted aryl or an optionally substituted heteroaryl;

$R_1$-$R_6$ independently are hydrogen, halo, optionally substituted amino, optionally substituted alkoxy, optionally substituted $C_{1-10}$ alkyl, haloalkyl, alkenyl, alkynyl, hydroxyalkyl, aminoalkyl, carboxyalkyl, nitro, cyano, acylamido, hydroxy, thiol, acyloxy, azido, carboxy, ethylenedioxo, carbonylamido or optionally substituted alkylthiol.

Preferred compounds of Formula I include compounds wherein Ar is an optionally substituted phenyl, pyridyl or furanyl. More preferably, Ar is phenyl, pyridyl or furanyl, optionally substituted with a substituted carbonyl or methyl, preferably carbonyl, at the meta-position. Another group of preferred compounds of Formula I include compounds wherein $R_5$ and $R_6$ are hydrogen.

One group of preferred compounds of the present invention are represented by Formula II:

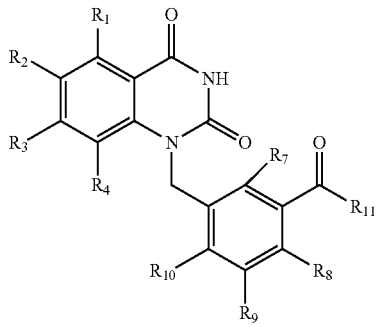

(II)

or pharmaceutically acceptable salts or prodrugs thereof, wherein:

$R_1$-$R_4$ independently are hydrogen, halo, optionally substituted amino, optionally substituted alkoxy, optionally substituted $C_{1-10}$ alkyl, haloalkyl, alkenyl, alkynyl, hydroxyalkyl, aminoalkyl, carboxyalkyl, nitro, cyano, acylamido, hydroxy, thiol, acyloxy, azido, carboxy, ethylenedioxo, carbonylamido or optionally substituted alkylthiol;

$R_7$-$R_{10}$ independently are hydrogen, halo, optionally substituted amino, alkoxy, $C_{1-10}$ alkyl, haloalkyl, aryl, heteroaryl, a carbocyclic group, a heterocyclic group, alkenyl, alkynyl, arylalkyl, arylalkenyl, arylakynyl, heteroarylalkyl, heteroarylalkenyl, heteroarylalkynyl, carbocycloalkyl, heterocycoalkyl, hydroxyalkyl, hydroxyalkoxy, aminoalkyl, aminoalkoxy, carboxyalkyl, carboxyalkoxy, nitro, cyano, acylamido, aminocarbonyl, hydroxy, thiol, acyloxy, azido, carboxy, carbonylamido, alkylsulfonyl, aminosulfonyl, dialkylaminosulfonyl, alkylsulfiniyl, alkylthiol, or substituted carbonyl;

$R_{11}$ is an optionally substituted amino, hydrazine, alkoxy, $C_{1-10}$ alkyl, haloalkyl, aryl, heteroaryl, carbocyclic group, heterocyclic group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, hydroyalkoxy, aminoalkyl, aminoalkoxy, carboxyalkyl, carboxyalkoxy, acylamido, hydroxy, thiol, carbonylamido, or alkylthiol.

One group of preferred compounds of Formula II includes compounds wherein $R_7$, $R_8$, $R_9$ or $R_{10}$ is hydrogen or halo, preferably fluoro. Another group of preferred compounds of Formula II includes compounds wherein $R_1$ or $R_2$ is hydrogen, fluoro, chloro, bromo or methyl. Another group of preferred compounds of Formula II includes compounds wherein $R_4$ is hydrogen, fluoro, methyl, methoxy or hydroxy. Another group of preferred compounds of Formula II includes compounds wherein $R_{11}$ is an optionally substituted amino, more preferably substituted piperazine or piperidine.

One group of preferred compounds of the present invention are represented by Formula III:

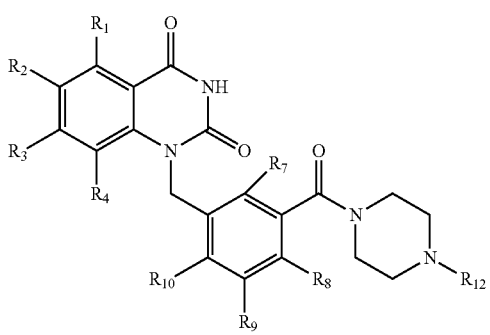

or pharmaceutically acceptable salts or prodrugs thereof, wherein:

$R_1$-$R_4$ independently are hydrogen, halo, optionally substituted amino, optionally substituted alkoxy, optionally substituted $C_{1-10}$ alkyl, haloalkyl, alkenyl, alkynyl, hydroxyalkyl, aminoalkyl, carboxyalkyl, nitro, cyano, acylamido, hydroxy, thiol, acyloxy, azido, carboxy, ethylenedioxo, carbonylamido or optionally substituted alkylthiol;

$R_7$-$R_{10}$ independently are hydrogen, halo, optionally substituted amino, alkoxy, $C_{1-10}$ alkyl, haloalkyl, aryl, heteroaryl, a carbocyclic group, a heterocyclic group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, hydroxyalkoxy, aminoalkyl, aminoalkoxy, carboxyalkyl, carboxyalkoxy, nitro, cyano, acylamido, aminocarbonyl, hydroxy, thiol, acyloxy, azido, carboxy, carbonylamido, alkylsulfonyl, aminosulfonyl, dialkylaminosulfonyl, alkylsulfiniyl, alkylthiol, or substituted carbonyl;

$R_{12}$ is an optionally substituted $C_{1-10}$ alkyl, haloalkyl, cycloalkyl, aryl, heteroaryl, carbocyclic group, heterocyclic group, alkenyl, alkynyl, acyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, alkylcarbonyl, cycloalkylcarbonyl, arylcarbonyl, heteroarylcarbonyl, heterocyclocarbonyl, aminocarbonyl, alkylsulfonyl, cycloalkylsulfonyl or aminosulfonyl.

In one preferred embodiment, one group preferred compounds of Formula III includes compounds wherein $R_{12}$ is selected from the group consisting of cycloalkyl, aryl, heteroaryl, carbocyclic group, heterocyclic group, arylalkyl, heteroarylalkyl, carbocycloalkyl, heterocycloalkyl, alkylcarbonyl, cycloalkylcarbonyl, arylcarbonyl, heteroarylcarbonyl or heterocyclocarbonyl. Another group of preferred compounds of Formula III includes compounds wherein $R_1$ or $R_2$ is hydrogen, fluoro, chloro, bromo or methyl; $R_4$ is hydrogen, fluoro, methoxy or hydroxy; $R_7$, $R_8$, $R_9$ or $R_{10}$ is hydrogen or fluoro.

Exemplary preferred compounds of Formulae I, II and III include, without limitation:

1-(3-Methoxycarbonylbenzyl)quinazoline-2,4(1H,3H)-dione;
1-(3-Carboxybenzyl)quinazoline-2,4(1H,3H)-dione;
1-(3-(4-(Pyridin-2-yl)piperazine-1-carbonyl)benzyl)quinazoline-2,4(1H,3H)-dione;
1-(3-(4-(Pyrimidin-2-yl)piperazine-1-carbonyl)benzyl)quinazoline-2,4(1H,3H)-dione;
1-(3-(4-Cyclohexylpiperazine-1-carbonyl)benzyl)quinazoline-2,4(1H,3H)-dione;
1-(3-(4-([1,2,4]Triazolo[4,3-b]pyridazin-6-yl)piperazine-1-carbonyl)benzyl)quinazoline-2,4(1H,3H)-dione;
1-(3-(4-Ethylpiperazine-1-carbonyl)benzyl)quinazoline-2,4(1H,3H)-dione;
1-(3-(4-Benzoylpiperazine-1-carbonyl)benzyl)quinazoline-2,4(1H,3H)-dione;
1-(3-(4-(4-Fluorobenzoyl)piperazine-1-carbonyl)benzyl)quinazoline-2,4(1H,3H)-dione;
1-(3-(4-(4-Chlorobenzoyl)piperazine-1-carbonyl)benzyl)quinazoline-2,4(1H,3H)-dione;
1-(3-(4-(4-Bromobenzoyl)piperazine-1-carbonyl)benzyl)quinazoline-2,4(1H,3H)-dione;
1-(3-(4-(4-Methoxybenzoyl)piperazine-1-carbonyl)benzyl)quinazoline-2,4(1H,3H)-dione;
1-(3-(4-(Tetrahydro-2H-pyran-4-yl)carbonylpiperazine-1-carbonyl)benzyl)quinazoline-2,4(1H,3H)-dione;
1-(3-(4-(Cyclopentylcarbonyl)piperazine-1-carbonyl)benzyl)quinazoline-2,4(1H,3H)-dione;
1-(3-(4-(Cyclopropylcarbonyl)piperazine-1-carbonyl)benzyl)quinazoline-2,4(1H,3H)-dione;
1-(3-(4-(Ethylsulfonyl)piperazine-1-carbonyl)benzyl)quinazoline-2,4(1H,3H)-dione;
1-(3-(4-Acetylpiperazine-1-carbonyl)benzyl)quinazoline-2,4(1H,3H)-dione;
1-(3-(4-Phenylpiperidine-1-carbonyl)benzyl)quinazoline-2,4(1H,3H)-dione;
1-(3-(4-Phenylpiperazine-1-carbonyl)benzyl)quinazoline-2,4(1H,3H)-dione;
1-(3-(4-(Pyrazin-2-yl)piperazine-1-carbonyl)benzyl)quinazoline-2,4(1H,3H)-dione;
1-(4-Fluoro-3-methoxycarbonylbenzyl)quinazoline-2,4(1H,3H)-dione;
1-(3-Carboxy-4-fluorobenzyl)quinazoline-2,4(1H,3H)-dione;
1-(3-(4-(Cyclopentylcarbonyl)piperazine-1-carbonyl)-4-fluorobenzyl)quinazoline-2,4(1H,3H)-dione;
1-(4-Fluoro-3-(4-(pyridin-2-yl)-piperazine-1-carbonyl)benzyl)quinazoline-2,4(1H,3H)-dione;
1-(4-Fluoro-3-(4-(pyrimidin-2-yl)-piperazine-1-carbonyl)benzyl)quinazoline-2,4(1H,3H)-dione;
1-(3-(4-(Cyclohexylcarbonyl)piperazine-1-carbonyl)benzyl)quinazoline-2,4(1H,3H)-dione;
1-(3-(4-(Benzo[d]isothiazol-3-yl)piperazine-1-carbonyl)benzyl)quinazoline-2,4(1H,3H)-dione;
1-(3-(4-(Piperidin-1-yl)piperidine-1-carbonyl)benzyl)quinazoline-2,4(1H,3H)-dione;
1-(3-(4-(Pyridin-4-yl)piperazine-1-carbonyl)benzyl)quinazoline-2,4(1H,3H)-dione;
1-(3-(4-(Cyclobutylcarbonyl)piperazine-1-carbonyl)benzyl)quinazoline-2,4(1H,3H)-dione;
1-(3-(4-(6-Fluorobenzo[d]isoxazol-3-yl)piperidine-1-carbonyl)benzyl)quinazoline-2,4(1H,3H)-dione;
1-(3-(4-(Thiophene-2-carbonyl)piperazine-1-carbonyl)benzyl)quinazoline-2,4(1H,3H)-dione;
1-(3-(4-(Furan-2-carbonyl)piperazine-1-carbonyl)benzyl)quinazoline-2,4(1H,3H)-dione;
1-(3-(4-(Furan-3-carbonyl)piperazine-1-carbonyl)benzyl)quinazoline-2,4(1H,3H)-dione;
1-(3-(4-(Thiophene-3-carbonyl)piperazine-1-carbonyl)benzyl)quinazoline-2,4(1H,3H)-dione;
1-(3-(4-(Pyridine-3-carbonyl)piperazine-1-carbonyl)benzyl)quinazoline-2,4(1H,3H)-dione;
1-(3-(4-(Pyridine-2-carbonyl)piperazine-1-carbonyl)benzyl)quinazoline-2,4(1H,3H)-dione;

1-(3-(4-(Pyridine-4-carbonyl)piperazine-1-carbonyl)benzyl)quinazoline-2,4(1H,3H)-dione;

1-(3-(4-Phenoxypiperidine-1-carbonyl)benzyl)quinazoline-2,4(1H,3H)-dione;

1-(3-(4-(Cycloprolycarbonyl)piperazine-1-carbonyl)-4-fluorobenzyl)quinazoline-2,4(1H,3H)-dione;

1-(3-(4-(Cyclohexylcarbonyl)piperazine-1-carbonyl)-4-fluorobenzyl)quinazoline-2,4(1H,3H)-dione;

1-(4-Fluoro-3-(4-(pyrazin-2-yl)piperazine-1-carbonyl)benzyl)quinazoline-2,4(1H,3H)-dione;

1-(3-(4-(Benzo[d]isothiazol-3-yl)piperazine-1-carbonyl)-4-fluorobenzyl)quinazoline-2,4(1H,3H)-dione;

1-(3-(4-(Cyclobutylcarbonyl)piperazine-1-carbonyl)-4-fluorobenzyl)quinazoline-2,4(1H,3H)-dione;

1-(3-(4-Benzoylpiperazine-1-carbonyl)-4-fluorobenzyl)quinazoline-2,4(1H,3H)-dione;

1-(4-Fluoro-3-(4-(thiophene-2-carbonyl)piperazine-1-carbonyl)benzyl)quinazoline-2,4(1H,3H)-dione;

1-(4-Fluoro-3-(4-(furan-2-carbonyl)piperazine-1-carbonyl)benzyl)quinazoline-2,4(1H,3H)-dione;

1-(3-(4-(Cyclopentylcarbonyl)piperazine-1-carbonyl)-6-fluorobenzyl)quinazoline-2,4(1H,3H)-dione;

1-(3-(4-(Cyclohexylcarbonyl)piperazine-1-carbonyl)-6-fluorobenzyl)quinazoline-2,4(1H,3H)-dione;

1-(6-Fluoro-3-(4-(pyrimidin-2-yl)piperazine-1-carbonyl)benzyl)quinazoline-2,4(1H,3H)-dione;

1-(6-Fluoro-3-(4-(pyridin-2-yl)piperazine-1-carbonyl)benzyl)quinazoline-2,4(1H,3H)-dione;

1-(6-Fluoro-3-(4-(thiophene-2-carbonyl)piperazine-1-carbonyl)benzyl)quinazoline-2,4(1H,3H)-dione;

1-(3-(4-(Cyclobutylcarbonyl)piperazine-1-carbonyl)-6-fluorobenzyl)quinazoline-2,4(1H,3H)-dione;

1-(6-Fluoro-3-(4-(furan-2-carbonyl)piperazine-1-carbonyl)benzyl)quinazoline-2,4(1H,3H)-dione;

1-(6-Chloro-3-(4-(cyclopentylcarbonyl)piperazine-1-carbonyl)benzyl)quinazoline-2,4(1H,3H)-dione;

1-(6-Chloro-3-(4-(pyrimidin-2-yl)piperazine-1-carbonyl)benzyl)quinazoline-2,4(1H,3H)-dione;

1-(6-Chloro-3-(4-(cyclohexylcarbonyl)piperazine-1-carbonyl)benzyl)quinazoline-2,4(1H,3H)-dione;

1-(6-Chloro-3-(4-(pyridin-2-yl)piperazine-1-carbonyl)benzyl)quinazoline-2,4(1H,3H)-dione;

1-(2-Chloro-3-(4-(cyclopentylcarbonyl)piperazine-1-carbonyl)benzyl)quinazoline-2,4(1H,3H)-dione;

1-(2-Chloro-3-(4-(pyrimidin-2-yl)piperazine-1-carbonyl)benzyl)quinazoline-2,4(1H,3H)-dione;

1-(2-Fluoro-3-(4-(pyrimidin-2-yl)piperazine-1-carbonyl)benzyl)quinazoline-2,4(1H,3H)-dione;

1-(3-(4-(Cyclopentylcarbonyl)piperazine-1-carbonyl)-2-fluorobenzyl)quinazoline-2,4(1H,3H)-dione;

1-(5-Fluoro-3-(4-(pyrimidin-2-yl)piperazine-1-carbonyl)benzyl)quinazoline-2,4(1H,3H)-dione;

1-(3-(4-(Cyclopentylcarbonyl)piperazine-1-carbonyl)-5-fluorobenzyl)quinazoline-2,4(1H,3H)-dione;

1-(4-Chloro-3-(4-(pyrimidin-2-yl)piperazine-1-carbonyl)benzyl)quinazoline-2,4(1H,3H)-dione;

1-(4-Chloro-3-(4-(cyclohexylcarbonyl)piperazine-1-carbonyl)benzyl)quinazoline-2,4(1H,3H)-dione;

1-((2-(4-(Cyclopentylcarbonyl)piperazine-1-carbonyl)furan-5-yl)methyl)quinazoline-2,4(1H,3H)-dione;

1-((2-(4-(Benzo[d]isothiazol-3-yl)piperazine-1-carbonyl)furan-5-yl)methyl)quinazoline-2,4(1H,3H)-dione;

1-((2-(4-(Cyclopentylcarbonyl)piperazine-1-carbonyl)pyridin-6-yl)methyl)quinazoline-2,4(1H,3H)-dione;

1-((2-(4-(Pyridin-2-yl)piperazine-1-carbonyl)pyridin-6-yl)methyl)quinazoline-2,4(1H,3H)-dione;

1-((2-(4-(Pyrimidin-2-yl)piperazine-1-carbonyl)pyridin-6-yl)methyl)quinazoline-2,4(1H,3H)-dione;

1-(3-(4-(Thiazol-2-yl)piperazine-1-carbonyl)benzyl)quinazoline-2,4(1H,3H)-dione;

1-(3-(4-(Cyclohexylmethyl)piperazine-1-carbonyl)benzyl)quinazoline-2,4(1H,3H)-dione;

1-(3-(4-(Cyclopentylmethyl)piperazine-1-carbonyl)benzyl)quinazoline-2,4(1H,3H)-dione;

1-(3-(4-(Cyclohexylsulfonyl)piperazine-1-carbonyl)benzyl)quinazoline-2,4(1H,3H)-dione;

1-(3-(4-(Cyclopentylcarbonyl)piperazine-1-carbonyl)benzyl)-7-fluoroquinazoline-2,4(1H,3H)-dione;

7-Fluoro-1-(3-(4-(pyrimidin-2-yl)piperazine-1-carbonyl)benzyl)quinazoline-2,4(1H,3H)-dione;

1-(3-(4-(Cyclopentylcarbonyl)piperazine-1-carbonyl)-7-methylquinazoline-2,4(1H,3H)-dione;

7-Methyl-1-(3-(4-(pyrimidin-2-yl)piperazine-1-carbonyl)benzyl)quinazoline-2,4(1H,3H)-dione;

6-Methyl-1-(3-(4-(pyrimidin-2-yl)piperazine-1-carbonyl)benzyl)quinazoline-2,4(1H,3H)-dione;

1-(3-(4-(Cyclopentylcarbonyl)piperazine-1-carbonyl)-6-methylquinazoline-2,4(1H,3H)-dione;

1-(4-Fluoro-3-(4-(pyrimidin-2-yl)piperazine-1-carbonyl)benzyl)-6-methylquinazoline-2,4(1H,3H)-dione;

1-(3-(4-(Cyclohexylcarbonyl)piperazine-1-carbonyl)-4-fluorobenzyl)-6-methylquinazoline-2,4(1H,3H)-dione;

1-(3-(4-(Cyclopentylcarbonyl)piperazine-1-carbonyl)-4-fluorobenzyl)-6-methylquinazoline-2,4(1H,3H)-dione;

6-Bromo-1-(3-(4-(cyclohexylcarbonyl)piperazine-1-carbonyl)benzyl)quinazoline-2,4(1H,3H)-dione;

6-Bromo-1-(3-(4-(cyclopentylcarbonyl)piperazine-1-carbonyl)benzyl)quinazoline-2,4(1H,3H)-dione;

6-Bromo-1-(3-(4-(pyrimidin-2-yl)piperazine-1-carbonyl)benzyl)quinazoline-2,4(1H,3H)-dione;

1-(3-(4-(Cyclopentylcarbonyl)piperazine-1-carbonyl)benzyl)-6-nitroquinazoline-2,4(1H,3H)-dione;

6-Nitro-1-(3-(4-(pyrimidin-2-yl)piperazine-1-carbonyl)benzyl)quinazoline-2,4(1H,3H)-dione;

1-(3-(4-(Cyclohexylsulfonyl)piperazine-1-carbonyl)benzyl)quinazoline-2,4(1H,3H)-dione;

1-(4-(4-Benzoylpiperazine-1-carbonyl)benzyl)piperazine-1-carbonyl)benzyl)quinazoline-2,4(1H,3H)-dione;

1-(4-(4-(Pyridin-2-yl)piperazine-1-carbonyl)benzyl)quinazoline-2,4(1H,3H)-dione;

1-(4-(4-(4-Methoxybenzoyl)piperazine-1-carbonyl)benzyl)quinazoline-2,4(1H,3H)-dione;

1-(4-(4-(4-Fluorobenzoyl)piperazine-1-carbonyl)benzyl)quinazoline-2,4(1H,3H)-dione;

1-(4-(4-(Pyrimidin-2-yl)piperazine-1-carbonyl)benzyl)quinazoline-2,4(1H,3H)-dione;

1-(4-(4-(4-Bromobenzoyl)piperazine-1-carbonyl)benzyl)quinazoline-2,4(1H,3H)-dione;

1-(4-(4-(Cyclopentylcarbonyl)piperazine-1-carbonyl)benzyl)quinazoline-2,4(1H,3H)-dione;

5-Chloro-1-(3-(4-(pyrimidin-2-yl)piperazine-1-carbonyl)benzyl)quinazoline-2,4(1H,3H)-dione;

5-Chloro-1-(3-(4-(cyclopentylcarbonyl)piperazine-1-carbonyl)benzyl)quinazoline-2,4(1H,3H)-dione;

5-Chloro-1-(3-(4-(cyclohexylcarbonyl)piperazine-1-carbonyl)benzyl)quinazoline-2,4(1H,3H)-dione;

5-Chloro-1-(4-fluoro-3-(4-(pyrimidin-2-yl)piperazine-1-carbonyl)benzyl)quinazoline-2,4(1H,3H)-dione;

5-Chloro-1-(3-(4-(cyclopentylcarbonyl)piperazine-1-carbonyl)-4-fluorobenzyl)quinazoline-2,4(1H,3H)-dione;

5-Chloro-1-(3-(4-(cyclohexylcarbonyl)piperazine-1-carbonyl)-4-fluorobenzyl)quinazoline-2,4(1H,3H)-dione;

5-Chloro-1-(4-fluoro-3-(4-(pyridin-2-yl)piperazine-1-carbonyl)benzyl)quinazoline-2,4(1H,3H)-dione;
5-Chloro-1-(4-fluoro-3-(4-(thiophene-2-yl)piperazine-1-carbonyl)benzyl)quinazoline-2,4(1H,3H)-dione;
5-Chloro-1-(3-(4-(cyclohexylcarbonyl)piperazine-1-carbonyl)-6-fluorobenzyl)quinazoline-2,4(1H,3H)-dione;
5-Chloro-1-(3-(4-(cyclopentylcarbonyl)piperazine-1-carbonyl)-6-fluorobenzyl)quinazoline-2,4(1H,3H)-dione;
5-Chloro-1-(6-fluoro-3-(4-(pyrimidin-2-yl)piperazine-1-carbonyl)benzyl)quinazoline-2,4(1H,3H)-dione;
6-Chloro-1-(3-(4-(pyrimidin-2-yl)piperazine-1-carbonyl)benzyl)quinazoline-2,4(1H,3H)-dione;
6-Chloro-1-(3-(4-(cyclopentylcarbonyl)piperazine-1-carbonyl)benzyl)quinazoline-2,4(1H,3H)-dione;
6-Chloro-1-(3-(4-(cyclohexylcarbonyl)piperazine-1-carbonyl)benzyl)quinazoline-2,4(1H,3H)-dione;
6-Chloro-1-(3-(4-(pyridin-2-yl)piperazine-1-carbonyl)benzyl)quinazoline-2,4(1H,3H)-dione;
6-Chloro-1-(3-(4-(thiophene-2-carbonyl)piperazine-1-carbonyl)benzyl)quinazoline-2,4(1H,3H)-dione;
6-Chloro-1-(3-(4-(cyclobutylcarbonyl)piperazine-1-carbonyl)benzyl)quinazoline-2,4(1H,3H)-dione;
6-Chloro-1-(4-fluoro-3-(4-pyrimidin-2-yl)piperazine-1-carbonyl)benzyl)quinazoline-2,4(1H,3H)-dione;
6-Chloro-1-(3-(4-(cyclopentylcarbonyl)piperazine-1-carbonyl)-4-fluorobenzyl)quinazoline-2,4(1H,3H)-dione;
6-Chloro-1-(3-(4-(cyclohexylcarbonyl)piperazine-1-carbonyl)-4-fluorobenzyl)quinazoline-2,4(1H,3H)-dione;
6-Chloro-1-(4-fluoro-3-(4-(pyridin-2-yl)piperazine-1-carbonyl)benzyl)quinazoline-2,4(1H,3H)-dione;
6-Chloro-1-(4-fluoro-3-(4-(thiophene-2-carbonyl)piperazine-1-carbonyl)benzyl)quinazoline-2,4(1H,3H)-dione;
6-Chloro-1-(3-(4-(cyclopropylcarbonyl)piperazine-1-carbonyl)-4-fluorobenzyl)quinazoline-2,4(1H,3H)-dione;
6-Chloro-1-(6-fluoro-3-(4-(pyrimidin-2-yl)piperazine-1-carbonyl)benzyl)quinazoline-2,4(1H,3H)-dione;
6-Chloro-1-(3-(4-(cyclopentylcarbonyl)piperazine-1-carbonyl)-6-fluorobenzyl)quinazoline-2,4(1H,3H)-dione;
6-Chloro-1-(3-(4-(cyclohexylcarbonyl)piperazine-1-carbonyl)-6-fluorobenzyl)quinazoline-2,4(1H,3H)-dione;
6-Chloro-1-(6-fluoro-3-(4-(thiophene-2-carbonyl)piperazine-1-carbonyl)benzyl)quinazoline-2,4(1H,3H)-dione;
5-Fluoro-1-(3-(4-(pyrimidin-2-yl)piperazine-1-carbonyl)benzyl)quinazoline-2,4(1H,3H)-dione;
1-(3-(4-(Cyclopentylcarbonyl)piperazine-1-carbonyl)benzyl)-5-fluoroquinazoline-2,4(1H,3H)-dione;
1-(3-(4-(Cyclohexylcarbonyl)piperazine-1-carbonyl)benzyl)-5-fluoroquinazoline-2,4(1H,3H)-dione;
5-Fluoro-1-(3-(4-(pyridin-2-yl)piperazine-1-carbonyl)benzyl)quinazoline-2,4(1H,3H)-dione;
5-Fluoro-1-(3-(4-(thiophene-2-carbonyl)piperazine-1-carbonyl)benzyl)quinazoline-2,4(1H,3H)-dione;
5-Fluoro-1-(4-fluoro-3-(4-(pyrimidin-2-yl)piperazine-1-carbonyl)benzyl)quinazoline-2,4(1H,3H)-dione;
1-(3-(4-(Cyclopentylcarbonyl)piperazine-1-carbonyl)-4-fluorobenzyl)-5-fluoroquinazoline-2,4(1H,3H)-dione;
1-(3-(4-(Cyclohexylcarbonyl)piperazine-1-carbonyl)-4-fluorobenzyl)-5-fluoroquinazoline-2,4(1H,3H)-dione;
5-Fluoro-1-(4-fluoro-3-(4-(pyridin-2-yl)piperazine-1-carbonyl)benzyl)quinazoline-2,4(1H,3H)-dione;
5-Fluoro-1-(4-fluoro-3-(4-(thiophene-2-carbonyl)piperazine-1-carbonyl)benzyl)quinazoline-2,4(1H,3H)-dione;
1-(3-(4-(Benzoylpiperazine-1-carbonyl)-4-fluorobenzyl)-5-fluoroquinazoline-2,4(1H,3H)-dione;
1-(3-(4-(Cyclohexylcarbonyl)piperazine-1-carbonyl)-8-fluoroquinazoline-2,4(1H,3H)-dione;
6-Fluoro-1-(3(4-(pyrimidin-2-yl)piperazine-1-carbonyl)benzyl)quinazoline-2,4(1H,3H)-dione;
6-Fluoro-1-(3(4-(pyridin-2-yl)piperazine-1-carbonyl)benzyl)quinazoline-2,4(1H,3H)-dione;
6-Fluoro-1-(3-(4-(thiophene-2-carbonyl)piperazine-1-carbonyl)benzyl)quinazoline-2,4(1H,3H)-dione;
1-(3-(4-(Cyclohexylcarbonyl)piperazine-1-carbonyl)-6-fluoroquinazoline-2,4(1H,3H)-dione;
1-(3-(4-(Cyclopentylcarbonyl)piperazine-1-carbonyl)-6-fluoroquinazoline-2,4(1H,3H)-dione;
6-Fluoro-1-(4-fluoro-3-(4-(pyrimidin-2-yl)piperazine-1-carbonyl)benzyl)quinazoline-2,4(1H,3H)-dione;
6-Fluoro-1-(4-fluoro-3-(4-(pyridin-2-yl)piperazine-1-carbonyl)benzyl)quinazoline-2,4(1H,3H)-dione;
6-Fluoro-1-(4-fluoro-3-(4-(thiophene-2-carbonyl)piperazine-1-carbonyl)benzyl)quinazoline-2,4(1H,3H)-dione;
1-(3-(4-(Cyclohexylcarbonyl)piperazine-1-carbonyl)-4-fluorobenzyl)-6-fluoroquinazoline-2,4(1H,3H)-dione;
1-(3-(4-(Cyclopentylcarbonyl)piperazine-1-carbonyl)-4-fluorobenzyl)-6-fluoroquinazoline-2,4(1H,3H)-dione;
6-Fluoro-1-(6-fluoro-3-(4-(pyrimidin-2-yl)piperazine-1-carbonyl)benzyl)quinazoline-2,4(1H,3H)-dione;
6-Fluoro-1-(6-fluoro-3-(4-(pyridin-2-yl)piperazine-1-carbonyl)benzyl)quinazoline-2,4(1H,3H)-dione;
6-Fluoro-1-(6-fluoro-3-(4-(thiophene-2-carbonyl)piperazine-1-carbonyl)benzyl)quinazoline-2,4(1H,3H)-dione;
1-(3-(4-(Cyclohexylcarbonyl)piperazine-1-carbonyl)-6-fluorobenzyl)-6-fluoroquinazoline-2,4(1H,3H)-dione;
1-(3-(4-(Cyclopentylcarbonyl)piperazine-1-carbonyl)-6-fluorobenzyl)-6-fluoroquinazoline-2,4(1H,3H)-dione;
5-Fluoro-1-(6-fluoro-3-(4-(pyrimidin-2-yl)piperazine-1-carbonyl)benzyl)quinazoline-2,4(1H,3H)-dione;
5-Fluoro-1-(6-fluoro-3-(4-(pyridin-2-yl)piperazine-1-carbonyl)benzyl)quinazoline-2,4(1H,3H)-dione;
5-Fluoro-1-(6-fluoro-3-(4-(thiophene-2-carbonyl)piperazine-1-carbonyl)benzyl)quinazoline-2,4(1H,3H)-dione;
1-(3-(4-(Cyclohexylcarbonyl)piperazine-1-carbonyl)-6-fluorobenzyl)-5-fluoroquinazoline-2,4(1H,3H)-dione;
1-(3-(4-(Cyclopentylcarbonyl)piperazine-1-carbonyl)-6-fluorobenzyl)-5-fluoroquinazoline-2,4(1H,3H)-dione;
5-Methyl-1-(3-(4-(pyrimidin-2-yl)piperazine-1-carbonyl)benzyl)quinazoline-2,4(1H,3H)-dione;
1-(3-(4-(Cyclopentylcarbonyl)piperazine-1-carbonyl)-5-methylquinazoline-2,4(1H,3H)-dione;
7-Chloro-1-(3-(4-(pyrimidin-2-yl)piperazine-1-carbonyl)benzyl)quinazoline-2,4(1H,3H)-dione;
7-Chloro-1-(3-(4-(cyclopentylcarbonyl)piperazine-1-carbonyl)benzyl)quinazoline-2,4(1H,3H)-dione;
1-(3-(4-(Cyclopropylcarbonyl)piperazine-1-carbonyl)-4-fluorobenzyl)-5-fluoroquinazoline-2,4(1H,3H)-dione;
6-Chloro-1-(3-(4-benzoylpiperazine-1-carbonyl)-4-fluorobenzyl)quinazoline-2,4(1H,3H)-dione;
1-(3-(4-(Cyclobutylcarbonyl)piperazine-1-carbonyl)benzyl)-5-fluoroquinazoline-2,4(1H,3H)-dione;
1-(3-(4-(Cyclobutylcarbonyl)piperazine-1-carbonyl)-4-fluorobenzyl)-5-fluoroquinazoline-2,4(1H,3H)-dione;
6-Chloro-1-(3-(4-(cyclobutylcarbonyl)piperazine-1-carbonyl)-6-fluorobenzyl)quinazoline-2,4(1H,3H)-dione;
5-Chloro-1-(3-(4-(cyclobutylcarbonyl)piperazine-1-carbonyl)-4-fluorobenzyl)quinazoline-2,4(1H,3H)-dione;
6-Chloro-1-(3-(4-(cyclobutylcarbonyl)piperazine-1-carbonyl)-4-fluorobenzyl)quinazoline-2,4(1H,3H)-dione;
5-Chloro-1-(3-(4-(cyclobutylcarbonyl)piperazine-1-carbonyl)-6-fluorobenzyl)quinazoline-2,4(1H,3H)-dione;
5-Chloro-1-(6-fluoro-3-(4-(thiophene-2-carbonyl)piperazine-1-carbonyl)benzyl)quinazoline-2,4(1H,3H)-dione;

5-Fluoro-1-(4-fluoro-3-(4-(furan-2-carbonyl)piperazine-1-carbonyl)benzyl)quinazoline-2,4(1H,3H)-dione;
5-Chloro-1-(6-fluoro-3-(4-(pyridin-2-yl)piperazine-1-carbonyl)benzyl)quinazoline-2,4(1H,3H)-dione;
6-Chloro-1-(6-fluoro-3-(4-(pyridin-2-yl)piperazine-1-carbonyl)benzyl)quinazoline-2,4(1H,3H)-dione;
6-Chloro-1-(5-fluoro-3-(4-(pyrimidin-2-yl)piperazine-1-carbonyl)benzyl)quinazoline-2,4(1H,3H)-dione;
5-Fluoro-1-(5-fluoro-3-(4-(pyrimidin-2-yl)piperazine-1-carbonyl)benzyl)quinazoline-2,4(1H,3H)-dione;
5-Chloro-1-(6-fluoro-3-(4-(pyridin-2-yl)piperazine-1-carbonyl)benzyl)quinazoline-2,4(1H,3H)-dione;
1-(3-(4-(Cyclopentylpiperazine-1-carbonyl)benzyl)quinazoline-2,4(1H,3H)-dione;
1-(3-(4-(Cyclopropylcarbonyl)piperazine-1-carbonyl)-4-fluorobenzyl)-6-fluoroquinazoline-2,4(1H,3H)-dione;
1-(3-(4-(Cyclobutylcarbonyl)piperazine-1-carbonyl)benzyl)-6-fluoroquinazoline-2,4(1H,3H)-dione;
1-(3-(4-(Cyclobutylcarbonyl)piperazine-1-carbonyl)-4-fluorobenzyl)-6-fluoroquinazoline-2,4(1H,3H)-dione;
1-(3-(4-Benzoylpiperazine-1-carbonyl)-4-fluorobenzyl)-6-fluoroquinazoline-2,4(1H,3H)-dione;
1-(3-(4-(Cyclobutylcarbonyl)piperazine-1-carbonyl)-6-fluorobenzyl)-5-fluoroquinazoline-2,4(1H,3H)-dione;
1-(3-(4-(Cyclobutylcarbonyl)piperazine-1-carbonyl)-6-fluorobenzyl)-6-fluoroquinazoline-2,4(1H,3H)-dione;
5-Fluoro-1-(6-fluoro-3-(4-(furan-2-carbonyl)piperazine-1-carbonyl)benzyl)quinazoline-2,4(1H,3H)-dione;
6-Fluoro-1-(4-fluoro-3-(4-(furan-2-carbonyl)piperazine-1-carbonyl)benzyl)quinazoline-2,4(1H,3H)-dione;
6-Fluoro-1-(5-fluoro-3-(4-(pyrimidin-2-yl)piperazine-1-carbonyl)benzyl)quinazoline-2,4(1H,3H)-dione;
1-(6-Chloro-3-(4-(pyrimidin-2-yl)piperazine-1-carbonyl)benzyl)-6-fluoroquinazoline-2,4(1H,3H)-dione;
6-Fluoro-1-(4-fluoro-3-(4-(thiazol-2-yl)piperazine-1-carbonyl)benzyl)quinazoline-2,4(1H,3H)-dione;
5-Fluoro-1-(4-fluoro-3-(4-(thiazol-2-yl)piperazine-1-carbonyl)benzyl)quinazoline-2,4(1H,3H)-dione;
1-(4-Fluoro-3-(4-(thiazol-2-yl)piperazine-1-carbonyl)benzyl)quinazoline-2,4(1H,3H)-dione;
1-(3-(4-(Cyclohexylcarbamoyl)piperazine-1-carbonyl)benzyl)quinazoline-2,4(1H,3H)-dione;
1-(4-Fluoro-3-(4-(pyrimidin-2-yl)piperazine-1-carbonyl)benzyl)quinazoline-2,4(1H,3H)-dione hydrochloride;
1-Fluoro1-(4-fluoro-3-(4-pyrimidin-2-yl)piperazine-1-carbonyl)benzyl)quinazoline-2,4(1H,3H)-dione hydrochloride;
1-(3-(4-(Pyrimidin-2-yl)piperazine-1-carbonyl)benzyl)quinazoline-2,4(1H,3H)-dione hydrochloride;
1-(3-((4-(Pyridin-2-yl)piperazine-1-yl)methyl)benzyl)quinazoline-2,4(1H,3H)-dione;
1-(3-(Naphthalen-2-yl)acetamidobenzyl)quinazoline-2,4(1H,3H)-dione;
1-(3,4-Dimethoxyphenyl)acetamidobenzyl)quinazoline-2,4(1H,3H)-dione;
1-(3-([1,2,4]Triazolo[4,3-a])pyridine-6-carbonyl)benzyl)quinazoline-2,4(1H,3H)-dione;
6-Fluoro-1-((2-(4-(pyrimidin-2-yl)piperazine-1-carbonyl)pyridin-6-yl)methyl)quinazoline-2,4(1H,3H)-dione;
5-Fluoro-1-(4-fluoro-3-(4-methoxybenzylcarbamoyl)benzyl)piperazine-1-carbonyl)pyridin-6-yl)methyl)quinazoline-2,4(1H,3H)-dione;
1-(3-(3-Chlorobenzylcarbamoyl)-4-fluorobenzyl)-5-fluoroquinazoline-2,4(1H,3H)-dione;
1-(3-(Benzylcarbamoyl)-4-fluorobenzyl)-5-fluoroquinazoline-2,4(1H,3H)-dione;
5-Methoxy-1-(3-(4-(pyrimidin-2-yl)piperazine-1-carbonyl)benzyl)quinazoline-2,4(1H,3H)-dione;
6-Methoxy-1-(3-(4-(pyrimidin-2-yl)piperazine-1-carbonyl)benzyl)quinazoline-2,4(1H,3H)-dione;
1-(3-(5-Bromopyrimidin-2-aminocarbamoyl)-5-fluorobenzyl)-5-fluoroquinazoline-2,4(1H,3H)-dione;
1-(3-(4-(Pyrimidin-2-yl)piperazine-1-carbonyl)benzyl)-7-(trifluoromethyl)quinazoline-2,4(1H,3H)-dione;
6,7-Ethylenedioxo-1-(3-(4-(pyrimidin-2-yl)piperazine-1-carbonyl)benzyl)quinazoline-2,4(1H,3H)-dione;
5-Fluoro-1-(6-methoxy-3-(4-(pyrimidin-2-yl)piperazine-1-carbonyl)benzyl)quinazoline-2,4(1H,3H)-dione;
7-Methoxy-1-(3-(4-(pyrimidin-2-yl)piperazine-1-carbonyl)benzyl)quinazoline-2,4(1H,3H)-dione;
5-Fluoro-1-(4-fluoro-3-(4-(tetrahydrofuran-2-carbonyl)piperazine-1-carbonyl)benzyl)quinazoline-2,4(1H,3H)-dione;
5-Fluoro-1-(4-nitro-3-(4-(pyrimidin-2-yl)piperazine-1-carbonyl)benzyl)quinazoline-2,4(1H,3H)-dione;
1-(3-(4-Cyclohexylpiperazine-1-carbonyl)-4-fluorobenzyl)-5-fluoroquinazoline-2,4(1H,3H)-dione;
5-Fluoro-1-(4-fluoro-3-(4-phenylpiperazine-1-carbonyl)benzyl)quinazoline-2,4(1H,3H)-dione;
5-Fluoro-1-(4-fluoro-3-(4-phenylpiperidine-1-carbonyl)benzyl)quinazoline-2,4(1H,3H)-dione;
1-(4-Bromo-3-(4-(pyrimidin-2-yl)piperazine-1-carbonyl)benzyl)-5-fluoroquinazoline-2,4(1H,3H)-dione;
6,7-Methylenedioxo-1-(3-(4-(pyrimidin-2-yl)piperazine-1-carbonyl)benzyl)quinazoline-2,4(1H,3H)-dione;
1-(3-(4-(Cyclohexylmethyl)piperazine-1-carbonyl)-4-fluorobenzyl)-5-fluoroquinazoline-2,4(1H,3H)-dione;
8-Fluoro-1-(3-(4-(pyrimidin-2-yl)piperazine-1-carbonyl)benzyl)quinazoline-2,4(1H,3H)-dione;
6-Amino-1-(3-(4-(pyrimidin-2-yl)piperazine-1-carbonyl)benzyl)quinazoline-2,4(1H,3H)-dione;
1-(2-(4-(Pyrimidin-2-yl)piperazine-1-carbonyl)benzyl)quinazoline-2,4(1H,3H)-dione;
8-Chloro-1-(3-(4-(pyrimidin-2-yl)piperazine-1-carbonyl)benzyl)quinazoline-2,4(1H,3H)-dione;
8-Methyl-1-(3-(4-(pyrimidin-2-yl)piperazine-1-carbonyl)benzyl)quinazoline-2,4(1H,3H)-dione;
8-Methoxy-1-(3-(4-(pyrimidin-2-yl)piperazine-1-carbonyl)benzyl)quinazoline-2,4(1H,3H)-dione;
8-Hydroxy-1-(3-(4-(pyrimidin-2-yl)piperazine-1-carbonyl)benzyl)quinazoline-2,4(1H,3H)-dione;
and pharmaceutically acceptable salts or prodrugs thereof.

The term "alkyl" as employed herein by itself or as part of another group refers to both straight and branched chain radicals of up to ten carbons. Useful alkyl groups include, straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups, which may be optionally substituted.

The term "alkenyl" as employed herein by itself or as part of another group means a straight or branched chain radical of 2-10 carbon atoms, unless the chain length is limited thereto, including at least one double bond between two of the carbon atoms in the chain. Typical alkenyl groups include ethenyl, 1-propenyl, 2-propenyl, 2-methyl-1-propenyl, 1-butenyl and 2-butenyl.

The term "alkynyl" is used herein to mean a straight or branched chain radical of 2-10 carbon atoms, unless the chain length is limited thereto, wherein there is at least one triple bond between two of the carbon atoms in the chain. Typical alkynyl groups include ethynyl, 1-propynyl, 1-methyl-2-propynyl, 2-propynyl, 1-butynyl and 2-butynyl.

Useful alkoxy groups include oxygen substituted by one of the $C_{1-10}$ alkyl Groups mentioned above, which may be optionally substituted. Alkoxy substituents include, without limitation, halo, morpholino, amino including alkylamino and dialkylamino, and carboxy including esters thereof.

Useful alkylthio groups include sulfur substituted by one of the $C_{1-10}$ alkyl groups mentioned above, which may be optionally substituted. Also included are the sulfoxides and sulfones of such alkylthio groups.

Useful amino and optionally substituted amino groups include —$NH_2$, —$NHR_{15}$ and —$NR_{15}R_{16}$, wherein $R_{15}$ and $R_{16}$ are optionally substituted $C_{1-10}$ alkyl, cycloalkyl, aryl, heteroaryl, or amino; or $R_{15}$ and $R_{16}$ are combined with the N to form a 5-8 membered heterocyclic ring structure, such as a piperidine; or $R_{15}$ and $R_{16}$ are combined with the N and an additional N or O atom to form a 5-8 membered heterocyclic ring, such as a piperazine, which are optionally substituted.

The groups as described herein, such as alkyl, alkoxy, alkylthio, alkenyl, alkynyl, cycloalkyl, carbonyl, carbocyclic and heterocyclic groups, aryl, arylalkyl, arylalkenyl, arylalkynyl and heteroaryl and heteroarylalkyl groups, may be optionally substituted. Generally, the term "optionally substituted" used herein indicates that the group that is "optionally substituted" may be optionally substituted by one or more (such as 1, 2, 3, or 4) substituents selected from the group consisting of halo, hydroxy, carboxyl, amino, nitro, cyano, $C_1$-$C_6$ acylamino, $C_1$-$C_6$ acyloxy, $C_1$-$C_6$ alkoxy, aryloxy, alkylthio, $C_1$-$C_6$ alkyl, $C_6$-$C_{10}$ aryl, $C_3$-$C_8$ cycloalkyl, $C_2$-$C_6$ alkenyl, $C_2$-$C_6$ alkynyl, $C_6$-$C_{10}$ aryl($C_2$-$C_6$)alkenyl, $C_6$-$C_{10}$ aryl($C_2$-$C_6$)alkynyl, saturated and unsaturated heterocyclic and heteroaryl, methylenedioxy, $C_1$-$C_6$ haloalkyl, $C_6C_6$-$C_{10}$ aryl($C_1$-$C_6$)alkyl, $C_1$-$C_6$ hydroxyalkyl, ureido, thiol, azido, $C_1$-$C_6$ alkoxy, carbonyl, di($C_{1-10}$ alkyl)amino, alkylsulfonyl, aminosulfonyl, dialkylaminosulfonyl, and alkylsulfiniyl, and the like. The substituent itself may also be optionally substituted.

Optional substituents on the alkyl, alkoxy, alkylthio, alkenyl, alkynyl, cycloalkyl, carbonyl, carbocyclic and heterocyclic groups may be one or more (such as 1, 2, 3, or 4) groups selected from the group consisting of halo, hydroxy, carboxyl, amino, nitro, cyano, $C_1$-$C_6$ acylamino, $C_1$-$C_6$ acyloxy, $C_1$-$C_6$ alkoxy, aryloxy, alkylthio, $C_6$-$C_{10}$ aryl, $C_3$-$C_8$ cycloalkyl, $C_2$-$C_6$ alkenyl, $C_2$-$C_6$ alkynyl, $C_6$-$C_{10}$ aryl($C_2$-$C_6$)alkenyl, $C_6$-$C_{10}$ aryl($C_2$-$C_6$)alkynyl, saturated and unsaturated heterocyclic and heteroaryl.

Optional substituents on the aryl, arylalkyl, arylalkenyl, arylalkynyl and heteroaryl and heteroarylalkyl groups may be one or more (such as 1, 2, 3, or 4) groups selected from the group consisting of halo, methylenedioxy, $C_1$-$C_6$ haloalkyl, $C_6$-$C_{10}$ aryl, $C_3$-$C_8$ cycloalkyl, $C_1$-$C_6$ alkyl, $C_2$-$C_6$ alkenyl, $C_2$-$C_6$ alkynyl, $C_6$-$C_{10}$ aryl($C_1$-$C_6$)alkyl, aryl($C_2$-$C_{10}$alkenyl, $C_6$-$C_{10}$ aryl($C_2$-$C_6$)alkynyl, $C_1$-$C_6$ hydroxyalkyl, nitro, amino, ureido, cyano, $C_1$-$C_6$ acylamino, hydroxy, thiol, $C_1$-$C_6$ acyloxy, azido, $C_1$-$C_6$ alkoxy, carbonyl, carboxy, di($C_{1-10}$ alkyl)amino, alkylsulfonyl, aminosulfonyl, dialkylaminosulfonyl, and alkylsulfiniyl.

The term "aryl" as employed herein by itself or as part of another group refers to monocyclic, bicyclic or tricyclic aromatic groups containing from 6 to 14 carbons in the ring portion.

Useful aryl groups include $C_{6-14}$ aryl, preferably $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

The term "carbocycle" as employed herein include cycloalkyl and partially saturated carbocyclic groups. Useful cycloalkyl groups are $C_{3-8}$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as described above, as well as cycloalkenyl groups, such as cyclopentenyl, cycloheptenyl and cyclooctenyl.

Useful halo or halogen groups include fluorine, chlorine, bromine and iodine.

The term "arylalkyl" is used herein to mean any of the above-mentioned $C_{1-10}$ alkyl groups substituted by any of the above-mentioned $C_{6-14}$ aryl groups. Preferably the arylalkyl group is benzyl, phenethyl or naphthylmethyl.

The term "arylalkenyl" is used herein to mean any of the above-mentioned $C_{2-10}$ alkenyl groups substituted by any of the above-mentioned $C_{6-14}$ aryl groups.

The term "arylalkynyl" is used herein to mean any of the above-mentioned $C_{2-10}$ alkynyl groups substituted by any of the above-mentioned $C_{6-14}$ aryl groups.

The term "aryloxy" is used herein to mean oxygen substituted by one of the above-mentioned $C_{6-14}$ aryl groups, which may be optionally substituted. Useful aryloxy groups include phenoxy and 4-methylphenoxy.

The term "arylalkoxy" is used herein to mean any of the above mentioned $C_{1-10}$ alkoxy groups substituted by any of the above-mentioned aryl groups, which may be optionally substituted. Useful arylalkoxy groups include benzyloxy and phenethyloxy.

Useful haloalkyl groups include alkyl groups, such as $C_{1-10}$ alkyl, or preferably $C_{1-6}$ alkyl substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful acylamino (acylamido) groups are any $C_{1-6}$ acyl (alkanoyl) attached to an amino nitrogen, e.g., acetamido, chloroacetamido, propionamido, butanoylamido, pentanoylamido and hexanoylamido, as well as aryl-substituted $C_{1-6}$ acylamino groups, e.g., benzoylamido, and pentafluorobenzoylamido. Useful acyl includes $C_{1-6}$ acyl, such as acetyl.

Useful acyloxy groups are any $C_{1-6}$ acyl (alkanoyl) attached to an oxy (—O—) group, e.g., formyloxy, acetoxy, propionoyloxy, butanoyloxy, pentanoyloxy and hexanoyloxy.

The term heterocycle (heterocyclic group) is used herein to mean a saturated or partially saturated 3-7 membered monocyclic, 7-10 membered bicyclic ring system, which consists of carbon atoms and one to four heteroatoms independently selected from the group consisting of O, N, and S, wherein the nitrogen and sulfur heteroatoms can be optionally oxidized, the nitrogen can be optionally quaternized. The term also includes any bicyclic group in which any of the above-defined heterocyclic rings is fused to a benzene ring. The heterocyclic ring of heterocycle can be substituted on carbon or on a nitrogen atom if the resulting compound is stable.

Useful saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl pyrazolinyl, tetronoyl and tetramoyl groups, which are optionally substituted.

The term "heteroaryl" as employed herein refers to groups having 5 to 14 ring atoms; 6, 10 or 14 π electrons shared in a cyclic array; and containing, as ring atom, carbon atoms and 1-3 heteroatoms selected from oxygen, nitrogen and sulfur.

Useful heteroaryl groups include thienyl (thiophenyl), benzo[d]isothiazol-3-yl, benzo[b]thienyl, naphtho[2,3-b]thienyl, thianthrenyl, furyl (furanyl), pyranyl, isobenzofuranyl, chromenyl, xanthenyl, phenoxanthiinyl, pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, tetrahydrocyclopenta[c]pyrazol-3-yl, pyrazolo[1,5-a]pyrimidinyl, benzoisoxazolyl such as 1,2-benzoisoxazol-3-yl, benzimidazolyl, 2-oxindolyl, thiadiazolyl, and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

The term "heteroaryloxy" is used herein to mean oxygen substituted by one of the above-mentioned heteroaryl groups, which may be optionally substituted. Useful heteroaryloxy groups include pyridyloxy, pyrazinyloxy, pyrrolyloxy, pyrazolyloxy, imidazolyloxy and thiophenyloxy.

The term "heteroarylalkoxy" is used herein to mean any of the above-mentioned $C_{1-10}$ alkoxy groups substituted by any of the above-mentioned heteroaryl groups, which may be optionally substituted.

Some of the compounds of the present invention may exist as stereoisomers including optical isomers. The invention includes all stereoisomers and both the racemic mixtures of such stereoisomers as well as the individual enantiomers that may be separated according to methods that are well known to those of ordinary skill in the art.

Examples of pharmaceutically acceptable addition salts include inorganic and organic acid addition salts, such as hydrochloride, hydrobromide, phosphate, sulphate, citrate, lactate, tartrate, maleate, fumarate, mandelate and oxalate; and inorganic and organic base addition salts with bases, such as sodium hydroxy, Tris(hydroxymethyl)aminomethane (TRIS, tromethane) and N-methyl-glucamine.

Examples of prodrugs of the compounds of the invention include the simple esters of carboxylic acid containing compounds (e.g., those obtained by condensation with a $C_{1-4}$ alcohol according to methods known in the art); esters of hydroxy containing compounds (e.g., those obtained by condensation with a $C_{1-4}$ carboxylic acid, $C_{3-6}$ dioic acid or anhydride thereof, such as succinic and fumaric anhydrides according to methods known in the art); imines of amino containing compounds (e.g., those obtained by condensation with a $C_{1-4}$ aldehyde or ketone according to methods known in the art); carbamate of amino containing compounds, such as those described by Leu, et. al., (*J. Med. Chem.* 42:3623-3628 (1999)) and Greenwald, et al., (*J. Med. Chem.* 42:3657-3667 (1999)); and acetals and ketals of alcohol containing compounds (e.g., those obtained by condensation with chloromethyl methyl ether or chloromethyl ethyl ether according to methods known in the art).

The compounds of this invention may be prepared using methods known to those skilled in the art, or the novel methods of this invention. Specifically, the compounds of this invention with Formula I, II or III can be prepared as illustrated by the exemplary reaction in Scheme 1 (Shunsuke Goto et al. Organic Process Research & Development, 2003, 7, 700-706). Reaction of quinazoline-2,4(1H,3H)-dione with hexamethyldisilazane (HMDS) in toluene in the presence of sulfuric acid produced the intermediate 2,4-di(trimethylsiloxy)quinazoline. Reaction of 2,4-di(trimethylsiloxy)quinazoline, with a substituted alkyl 3-(halomethyl)benzoate, such as methyl 3-(bromomethyl)benzoate in DMF, followed by treatment with 1,4-dioxane and methanol, produced 1-(3-methoxycarbonylbenzyl)quinazoline-2,4(1H,3H)-dione. Treatment of the ester with NaOH in water-methanol produced 1-(3-carboxybenzyl)quinazoline-2,4(1H,3H)-dione. Coupling of the acid with a substituted amine, such as 1-(pyridin-2-yl)piperazine, in the presence of coupling agents, such as 2-(7-aza-1H-benzotriazole-1-yl)-1,1,3,3-tetramethyluronium hexafluorophosphate (HATU) and N,N-diisopropylethylamine (DIPEA) in DMF, produced the targeted compound 1-(3-(4-(pyridin-2-yl)piperazine-1-carbonyl)benzyl)quinazoline-2,4(1H,3H)-dione.

Other related compounds can be prepared similarly. For example, replacement of methyl 3-(bromomethyl)benzoate with methyl 6-(bromomethyl)pyridine-2-carboxylate produced the targeted compound 1((2-(4-(pyridin-2-yl)piperazine-1-carbonyl)pyridin-6-yl)methyl)quinazoline-2,4(1H,3H)-dione. Replacement of methyl 3-(bromomethyl)benzoate with ethyl 5-(chloromethyl)furan-2-carboxylate produced the targeted compound 1((2(4-cyclopentylcarbonylpiperazine-1-carbonyl)furan-5-yl)methyl)quinazoline-2,4(1H,3H)-dione. Replacement of methyl 3-(bromomethyl)benzoate with methyl 3-(2-bromoethyl)benzoate produced the targeted compound 1-3-(4-(pyrimidin-2-yl)piperazine-1-carbonyl)phenethyl)quinazoline-2,4(1H,3H)-dione.

For quinazoline-2,4(1H,3H)-dione with a substituent in the 8-position, such as 8-chloroquinazoline-2,4(1H,3H)-dione, reaction with hexamethyldisilazane (HMDS) followed by treatment of the intermediate 8-chloro-2,4-di(trimethylsiloxy)quinazoline with methyl 3-(bromomethyl)benzoate produced a mixture of 1-(3-methoxycarbonylbenzyl)quinazoline-2,4(1H,3H)-dione and 3-(3-methoxycarbonylbenzyl)quinazoline-2,4(1H,3H)-dione. The mixture can be separated, hydrolyzed, and coupled with a substituted amine to produce the 1-substituted compound and 3-substituted compound, respectively. Alternatively, the 3-substituted compound also can be prepared from reaction of quinazoline-2,4(1H,3H)-dione with methyl 3-(bromomethyl)benzoate and $K_2CO_3$ in DMF, followed by hydrolysis and coupling of the acid with a substituted amine.

Scheme 1

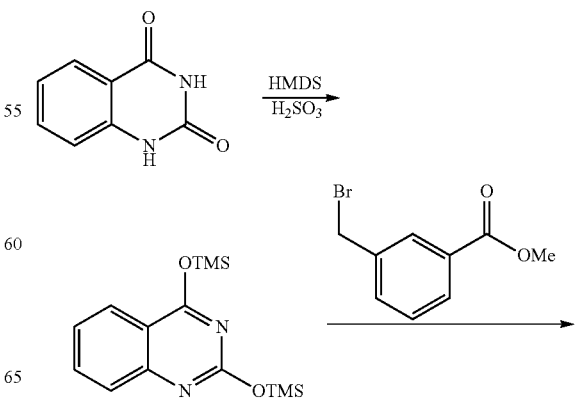

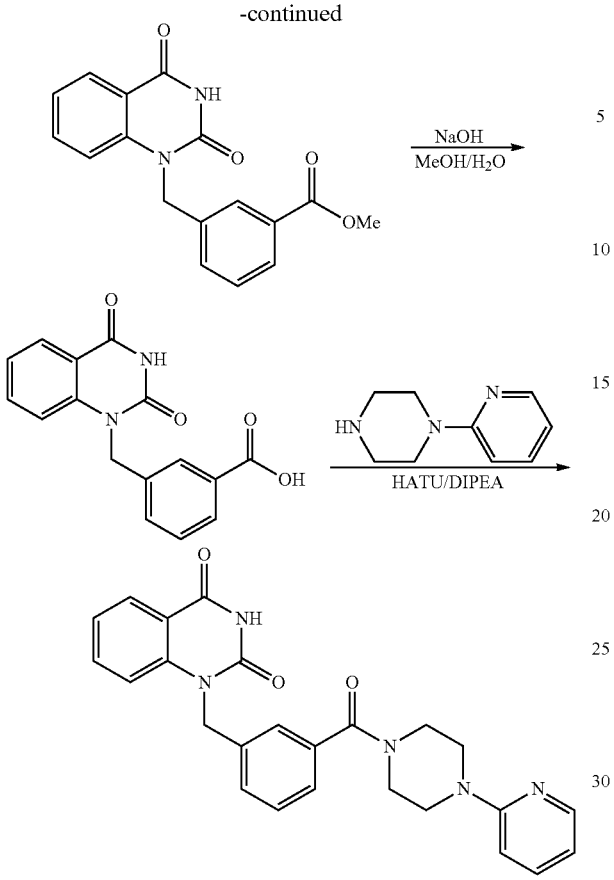

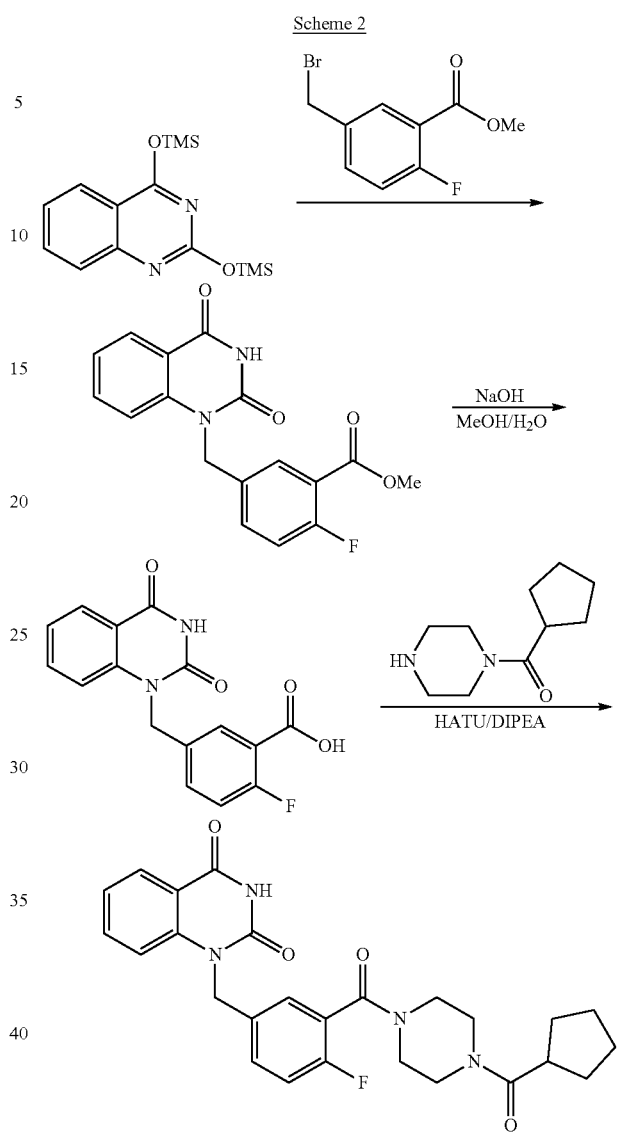

Compounds of this invention can be prepared as illustrated by the exemplary reaction in Scheme 2. Reaction of the intermediate 2,4-di(trimethylsiloxy)quinazoline with a substituted alkyl 3-(halomethyl)benzoate, such as methyl 5-(bromomethyl)-2-fluorobenzoate in DMF, followed by treatment with 1,4-dioxane and methanol, produced 1-(4-fluoro-3-methoxycarbonylbenzyl)quinazoline-2,4(1H,3H)-dione. Treatment of the ester with NaOH in water-methanol produced 1-(3-carboxy-4-fluorobenzyl)quinazoline-2,4(1H,3H)-dione. Coupling of the acid with a substituted amine, such as 1-cyclopentylcarbonylpiperazine, in the presence of coupling agents, such as HATU and DIPEA in DMF, produced the targeted compound 1-(3-(4-cyclopentylcarbonylpiperazine-1-carbonyl)-4-fluorobenzyl)quinazoline-2,4(1H,3H)-dione.

Other related compounds can be prepared similarly. For example, replacement of quinazoline-2,4(1H,3H)-dione with a substituted quinazoline-2,4(1H,3H)-dione, such as 5-fluoroquinazoline-2,4(1H,3H)-dione, which can be prepared from reaction of 2-amino-6-fluorobenzoic acid with potassium cyanate, produced the targeted compound 1-(3-(4-cyclopentylcarbonylpiperazine-1-carbonyl)-4-fluorobenzyl)-5-fluoroquinazoline-2,4(1H,3H)-dione. Replacement of methyl 5-(bromomethyl)-2-fluorobenzoate with another substituted methyl 3-(bromomethyl)benzoate, such as methyl 3-(bromomethyl)-4-fluorobenzoate, produced the targeted compound 1-(3-(4-cyclopentylcarbonylpiperazine-1-carbonyl)-6-fluorobenzyl)quinazoline-2,4(1H,3H)-dione. Replacement of 1-cyclopentylcarbonylpiperazine with another substituted amine, such as 1-(pyrimidin-2-yl)piperazine, produced the targeted compound 1-(-4-fluoro-3-(-4-pyrimidin-2-yl)carbonylpiperazine-1-carbonyl)benzyl)quinazoline-2,4(1H,3H)-dione.

The compounds of this invention can be prepared as illustrated by the exemplary reaction in Scheme 3. Reaction of 2-amino-3-methylbenzoic acid with triphosgene in THF produced 8-methyl-1H-benzo[d][1,3]oxazine-2,4-4-dione, which was treated with tert-butylamine and DMAP in DMF to produce 2-amino-N-tert-butyl-3-methylbenzamide. Reaction of the benzamide with CDI in THF produced 3-tert-butyl-8-methylquinazoline-2,4(1H,3H)-dione, which was reacted with methyl 3-(bromomethyl)benzoate and MeOna in DMF, followed by treatment with hydrochloric acid aqueous solution, to produce 8-methyl-1-(3-carboxybenzyl)quinazoline-2,4(1H,3H)-dione. Coupling of the acid with 2-(piperazin-1-yl)pyrimidine in the presence of coupling agents, such as HATU and DIPEA in DMF, produced the targeted compound 8-methyl-1-(3-(4-(pyrimidin-2-yl)piperazine-1-carbonyl)benzyl)quinazoline-2,4(1H,3H)-dione.

Other related compounds can be prepared similarly. For example, replacement of 2-amino-3-methylbenzoic acid with other substituted 2-aminobenzoic acid, such as 2-amino-3-methoxybenzoic acid, produced the targeted compound 8-methoxy-1-(3-(4-(pyrimidin-2-yl)piperazine-1-carbonyl)benzyl)quinazoline-2,4(1H,3H)-dione.

Scheme 3

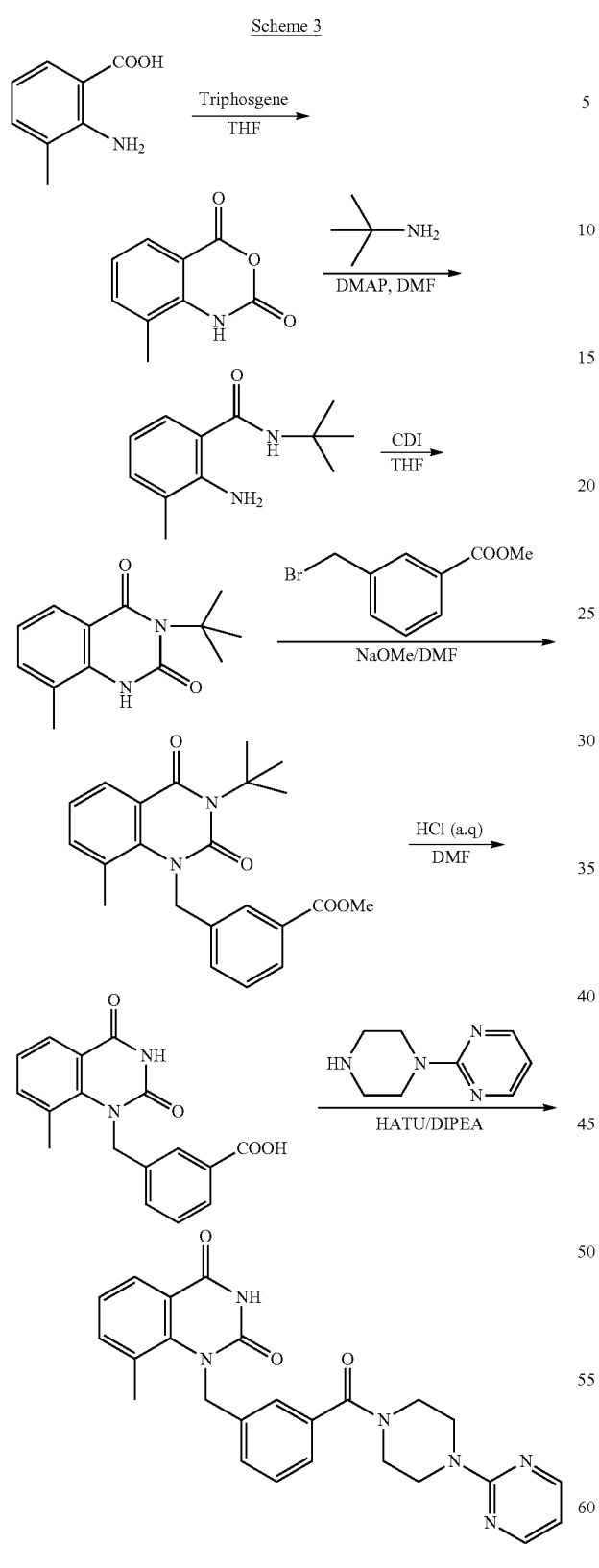

methyl 3-(3-(2-bromobenzoyl)ureido)benzoate. Reaction of the benzoate with potassium tert-butoxide in DMF produced 1-(3-methoxycarbonylphenyl)quinazoline-2,4(1H,3H)-dione. Hydrolysis of the ester with NaOH in water-methanol produced 1-(3-carboxyphenyl)quinazoline-2,4(1H,3H)-dione. Coupling of the acid with 2-(piperazin-1-yl)pyrimidine in the presence of coupling agents, such as HATU and DIPEA in DMF, produced the targeted compound 1-(3-(1-(pyrimidin-2-yl)piperazine-4-carbonyl)phenyl)quinazoline-2,4(1H,3H)-dione.

Scheme 4

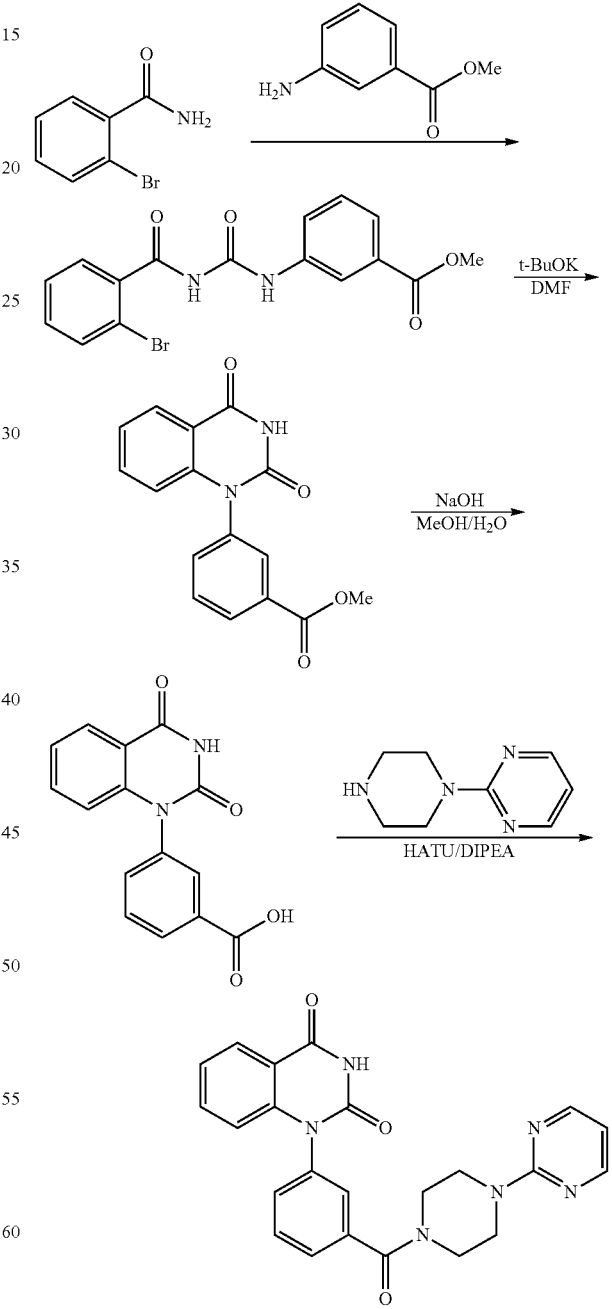

The 1-phenyl substituted compound can be prepared as illustrated by the exemplary reaction in Scheme 4. Reaction of 2-bromobenzamide with oxalyl chloride in DCM, followed by addition of methyl 3-aminobenzoate produced An important aspect of the present invention is the discovery that compounds having Formula I, II or III are PARP inhibitors. Therefore, these compounds are useful for the treatment of a variety of clinical conditions responsive to the inhibition of PARP activity, such as cancer.

The present invention includes a therapeutic method comprising administering to a mammal an effective amount of a compound of Formula I, II or III, or a pharmaceutically acceptable salt or prodrug thereof, wherein said therapeutic method is useful for the treatment of diseases due to abnormal PARP activity, such as cancer. Such diseases that can be treated or prevented by the method or pharmaceutical composition of the present invention include, but are not limited to, liver cancer, melanoma, Hodgkin's disease, non-Hodgkin's lymphoma, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinoma, mycosis fungoides, head or neck carcinoma, osteogenic sarcoma, pancreatic carcinoma, acute granulocytic leukemia, hairy cell leukemia, neuroblastoma, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, and prostatic carcinoma.

Compounds of the present invention also are useful for the treatment or prevention of other clinical conditions due to abnormal PARP activity, such as excessive cell death, including central nervous system diseases such as stroke and neurodegenerative diseases.

In practicing the therapeutic methods, effective amounts of compositions containing therapeutically effective concentrations of the compounds of Formula I, II or III formulated for oral, intravenous, local or topical application, for the treatment of neoplastic diseases and other diseases, are administered to an individual exhibiting the symptoms of one or more of these disorders. The amounts are effective to ameliorate or eliminate one or more symptoms of the disorders. An effective amount of a compound for treating a particular disease is an amount that is sufficient to ameliorate, or in some manner reduce, the symptoms associated with the disease. Such amount may be administered as a single dosage or may be administered according to a regimen, whereby it is effective. The amount may cure the disease but, typically, is administered in order to ameliorate the symptoms of the disease. Typically, repeated administration is required to achieve the desired amelioration of symptom.

In another embodiment, a pharmaceutical composition comprising a compound of Formula I, II or III or a pharmaceutically acceptable salt thereof, which functions as PARP inhibitor, in combination with a pharmaceutically acceptable vehicle, is provided.

Another embodiment of the present invention is directed to a composition effective to inhibit neoplasia comprising a compound of Formula I, II or III, or a pharmaceutically acceptable salt or prodrug thereof, which functions as a PARP inhibitor, in combination with at least one known anticancer agent or a pharmaceutically acceptable salt thereof. Examples of known anticancer agents which may be used for combination therapy include, but not are limited to alkylating agents, such as busulfan, melphalan, chlorambucil, cyclophosphamide, ifosfamide, temozolomide, bendamustine, cis-platin, mitomycin C, bleomycin, and carboplatin; topoisomerase I inhibitors, such as camptothecin, irinotecan, and topotecan; topoisomerase II inhibitors, such as doxorubicin, epirubicin, aclarubicin, mitoxantrone, elliptinium and etoposide; RNA/DNA antimetabolites, such as 5-azacytidine, gemcitabine, 5-fluorouracil and methotrexate; DNA antimetabolites, such as 5-fluoro-2'-deoxy-uridine, fludarabine, nelarabine, ara-C, alanosine, pralatrexate, pemetrexed, hydroxyurea and thioguanine; antimitotic agents, such as colchicine, vinblastine, vincristine, vinorelbine, paclitaxel, ixabepilone, cabazitaxel, and docetaxel; antibodies, such as campath, Panitumumab, Ofatumumab, Avastin, Herceptin®, Rituxan®; kinase inhibitors such as imatinib, gefitinib, erlotinib, lapatinib, sorafenib, sunitinib, nilotinib, dasatinib, pazopanib, temsirolimus and everolimus; HDAC inhibitors such as vorinostat and romidepsin. Other known anticancer agents which may be used for combination therapy include tamoxifen, letrozole, fulvestrant, mitoguazone, octreotide, retinoic acid, arsenic trioxide, zoledronic acid, bortezomib, thalidomide and lenalidomide.

In practicing the methods of the present invention, the compound of the invention may be administered together with at least one known anticancer agent as part of a unitary pharmaceutical composition. Alternatively, the compound of the invention may be administered apart from at least one known anticancer agent. In one embodiment, the compound of the invention and at least one known anticancer agent are administered substantially simultaneously, i.e. the compounds are administered at the same time or one after the other, so long as the compounds reach therapeutic levels in the blood at the same time. In another embodiment, the compound of the invention and at least one known anticancer agent are administered according to their individual dose schedule, so long as the compounds reach therapeutic levels in the blood.

Another embodiment of the present invention is directed to a composition effective to inhibit neoplasia comprising a bioconjugate of a compound described herein, which functions as a PARP inhibitor, in bioconjugation with at least one known therapeutically useful antibody, such as Herceptin® or Rituxan®, growth factors, such as DGF, NGF; cytokines, such as IL-2, IL-4, or any molecule that binds to the cell surface. The antibodies and other molecules will deliver a compound described herein to its targets and make it an effective anticancer agent. The bioconjugates could also enhance the anticancer effect of the therapeutically useful antibodies, such as Herceptin® or Rituxan®.

Similarly, another embodiment of the present invention is directed to a composition effective to inhibit neoplasia comprising a compound of Formula I, II or III, or its pharmaceutically acceptable salt or prodrug, which functions as a PARP inhibitor, in combination with radiation therapy. In this embodiment, the compound of the invention may be administered at the same time as the radiation therapy is administered or at a different time.

Yet another embodiment of the present invention is directed to a composition effective for post-surgical treatment of cancer, comprising a compound of Formula I, II or III, or its pharmaceutically acceptable salt or prodrug, which functions as a PARP inhibitor. The invention also relates to a method of treating cancer by surgically removing the cancer and then treating the mammal with one of the pharmaceutical compositions described herein.

Pharmaceutical compositions within the scope of this invention include all compositions wherein the compounds of the present invention are contained in an amount that is effective to achieve its intended purpose. While individual needs vary, determination of optimal ranges of effective amounts of each component is within the skill of the art. Typically, the compounds may be administered to mammals, orally at a dose of 0.0025 to 50 mg/kg of body weight, per day, or an equivalent amount of the pharmaceutically acceptable salt thereof, to a mammal being treated. Preferably, approximately 0.01 to approximately 10 mg/kg of body weight is orally administered. If a known anticancer agent is also administered, it is administered in an amount that is effective to achieve its intended purpose. The amounts of such known anticancer agents effective for cancer are well known to those skilled in the art.

The unit oral dose may comprise from approximately 0.01 to approximately 50 mg, preferably approximately 0.1 to approximately 10 mg of the compound of the invention. The unit dose may be administered one or more times daily, as one or more tablets, each containing from approximately 0.1 to approximately 50 mg, conveniently approximately 0.25 to 10 mg of the compound or its solvates.

In a topical formulation, the compound may be present at a concentration of approximately 0.01 to 100 mg per gram of carrier.

In addition to administering the compound as a raw chemical, the compounds of the invention may be administered as part of a pharmaceutical preparation containing suitable pharmaceutically acceptable carriers comprising excipients and auxiliaries, which facilitate processing of the compounds into preparations that may be used pharmaceutically. Preferably, the preparations, particularly those preparations which may be administered orally and that may be used for the preferred type of administration, such as tablets, dragees, and capsules, as well as suitable solutions for administration by injection or orally, contain from approximately 0.01 to 99 percent, preferably from approximately 0.25 to 75 percent of active compound(s), together with the excipient.

Also included within the scope of the present invention are the non-toxic pharmaceutically acceptable salts of the compounds of the present invention. Acid addition salts are formed by mixing a solution of the compounds of the present invention with a solution of a pharmaceutically acceptable non-toxic acid, such as hydrochloric acid, fumaric acid, maleic acid, succinic acid, acetic acid, citric acid, tartaric acid, carbonic acid, phosphoric acid, oxalic acid, and the like. Base addition salts are formed by mixing a solution of the compounds of the present invention with a solution of a pharmaceutically acceptable non-toxic base, such as sodium hydroxide, potassium hydroxide, choline hydroxide, sodium carbonate, Tris, N-methyl-glucamine and the like.

The pharmaceutical compositions of the invention may be administered to any mammal, which may experience the beneficial effects of the compounds of the invention. Foremost, among such mammals are humans and veterinary animals, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner, which is itself known, e.g., by means of conventional mixing, granulating, dragee-making, dissolving, or lyophilizing processes. Thus, pharmaceutical preparations for oral use may be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular: fillers, such as saccharides, e.g. lactose or sucrose, mannitol or sorbitol; cellulose preparations and/or calcium phosphates, e.g. tricalcium phosphate or calcium hydrogen phosphate; as well as binders, such as starch paste, using, e.g., maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, e.g., silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropylmethyl-cellulose phthalate, are used. Dye stuffs or pigments may be added to the tablets or dragee coatings, e.g., for identification or in order to characterize combinations of active compound doses.

Other pharmaceutical preparations, which may be used orally, include push-fit capsules made of gelatin, as well as soft, sealed capsules made of gelatin and a plasticizer, such as glycerol or sorbitol. The push-fit capsules may contain the active compounds in the form of: granules, which may be mixed with fillers, such as lactose; binders, such as starches; and/or lubricants, such as talc or magnesium stearate and, optionally, stabilizers. In soft capsules, the active compounds are preferably dissolved or suspended in suitable liquids, such as fatty oils, or liquid paraffin. In addition, stabilizers may be added.

Suitable formulations for parenteral administration include aqueous solutions of the active compounds in water-soluble form, e.g., water-soluble salts and alkaline solutions. In addition, suspensions of the active compounds as appropriate oily injection suspensions may be administered. Suitable lipophilic solvents or vehicles include fatty oils, e.g., sesame oil, or synthetic fatty acid esters, e.g., ethyl oleate or triglycerides or polyethylene glycol-400, or cremophor, or cyclodextrins. Aqueous injection suspensions may contain substances which increase the viscosity of the suspension include, e.g., sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of skin cancer.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included, as well as agents imparting color or fragrance, if desired. Additionally, transdermal penetration enhancers may be employed in these topical formulations. Examples of such enhancers are found in U.S. Pat. Nos. 3,989,816 and 4,444,762.

Creams are preferably formulated from a mixture of mineral oil, self-emulsifying beeswax and water in which mixture of the active ingredient, dissolved in a small amount of an oil, such as almond oil, is admixed. A typical example of such a cream is one which includes approximately 40 parts water, approximately 20 parts beeswax, approximately 40 parts mineral oil and approximately 1 part almond oil.

Ointments may be formulated by mixing a solution of the active ingredient in a vegetable oil, such as almond oil, with warm soft paraffin and allowing the mixture to cool. A typical example of such an ointment is one which includes approximately 30% almond oil and approximately 70% white soft paraffin by weight.

The present invention also includes the use of the compounds of the subject invention in the manufacture of a medicament for treating or preventing a disorder responsive to the inhibition of PARP activity in a mammal suffering therefrom. The medicament may include, such as the pharmaceutical compositions as described above.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLES

General Remarks

All reagents were of commercial quality. Solvents were dried and purified by standard methods. Mass spectrum analyses were recorded on a Platform II (Agilent 6110) quadrupole mass spectrometer fitted with an electrospray rinterface. $^1$H NMR spectra was recorded at 300 MHz and at 300 K, on a Brücker AMX 300 apparatus. Chemical shifts were recorded as parts per million (ppm) downfield from TMS (0.00 ppm), and J coupling constants were reported in hertz (Hz).

Example 1

1-(3-Methoxycarbonylbenzyl)quinazoline-2,4(1H,3H)-dione

Quinazoline-2,4(1H,3H)-dione (1.0 g, 6.2 mmol), hexamethyldisilazane (HMDS, 2.5 g, 15.4 mmol), and toluene (50 mL) were added into 100 mL two-mouth flask. Concentrated sulfuric acid (0.06 g) was added into the flask when stirring. The mixture was refluxed and reacted for 8 h. Toluene and excessive HMDS were removed via evaporation under reduced pressure, thus obtaining an intermediate product 2,4-di(trimethylsilyloxy)quinazoline.

The intermediate product 2,4-di(trimethylsilyloxy)quinazoline, methyl 3-(bromomethyl)benzoate (2.1 g, 9.2 mmol) and DMF (1 mL) were added in turn into a 50 mL single-mouth flask, and then the temperature were raised to 115-130° C. and reacted for 3 hours. 1,4-dioxane (6 mL) and methanol (10 mL) were added after the reaction mixture was cooled to 100° C. Then the mixture was refluxed for 30 minutes. The mixture was filtered after it was cooled to room temperature. The precipitate was washed with water (20 mL) and methonal (10 mL), respectively, and dried to give the title compound (1.6 g, 83.7% yield) as white powder. $^1$H NMR (DMSO-$d_6$): 11.76 (s, 1H), 8.00 (dd, J=7.8 and 1.2 Hz, 1H), 7.89 (s, 1H), 7.83 (d, J=7.8 Hz, 1H), 7.65-7.43 (m, 3H), 7.25-7.20 (m, 2H), 5.36 (s, 2H), 3.80 (s, 3H). MS: m/z 311.1 $[M+H]^+$.

Example 2

1-(3-Carboxybenzyl)quinazoline-2,4(1H,3H)-dione 1-(3-methoxycarbonylbenzyl)quinazoline-2,4(1H,3H)-dione (1.6 g, 5.2 mmol), NaOH (0.31 g, 7.7 mmol), water (40 mL) and methanol (40 mL) were added into a 250 mL three-mouth flask. The mixture was refluxed and reacted for 3 hours. The methanol was removed via evaporation under reduced pressure after the reaction was finished. The mixture was adjusted to pH=2-3 by 3N HCl, forming many precipitates. The mixture was filtered and the solid was washed by water and methonal. The solids were dried to give the title compound as white solid (1.2 g, 78% yield). $^1$H NMR (300 M, DMSO-$d_6$): 13.09 (brs, 1H), 11.77 (s, 1H), 8.01 (dd, J=7.7 and 1.4 Hz, 1H), 7.84-7.80 (m, 2H), 7.66-7.61 (m, 1H), 7.53 (d, J=7.8 Hz, 1H), 7.44 (t, J=7.7 Hz, 1H), 7.27-7.21 (m, 2H), 5.36 (s, 2H). MS: m/z 297.1 $[M+H]^+$.

Example 3

1-(3-(4-(Pyridin-2-yl)piperazine-1-carbonyl)benzyl)quinazoline-2,4(1H,3H)-dione 1-(3-carboxybenzyl)quinazoline-2,4(1H,3H)-dione (0.2 mmol), 1-(pyridin-2-yl)piperazine (0.2 mmol), 2-(7-aza-1H-benzotriazole-1-yl)-1,1,3,3-tetramethyluronium hexafluorophosphate (HATU, 0.26 mmol), N,N-diisopropylethylamine (DIPEA, 0.4 mmol) and DMF (5 mL) were added into a 50 mL two-mouth flask. The obtained mixture was stirred at room temperature for 3 hours. To the mixture was added 50 mL of water and it was extracted by dichloromethane (DCM, 50 mL×2). The organic layer was washed by 1N HCl (50 mL×2) and saturated NaCl aquenous solution (50 mL×2), dried with anhydrous sodium sulphate, and evaporated under reduced pressure to give the crude product. The crude product was purified by column chromatography (ethyl acetate) to give the title compound as white solid (7.7 mg, 8.6% yield). $^1$H NMR (DMSO-$d_6$): 11.69 (s, 1H), 8.09 (dd, J=5.0 and 1.7 Hz, 1H), 7.99 (dd, J=8.0 and 1.7 Hz, 1H), 7.64 (t, J=7.1 Hz, 1H), 7.53 (t, J=7.8 Hz, 1H), 7.40-7.21 (m, 6H), 6.77 (d, J=8.7 Hz, 1H), 6.64 (dd, J=7.1 and 5.0 Hz, 1H), 5.34 (s, 2H), 3.40-3.20 (m, 8H). MS: m/z 442.3 $[M+H]^+$.

The following compounds were prepared from 1-(3-carboxybenzyl)quinazoline-2,4(1H,3H)-dione and the corresponding substituted piperazine or piperidine using a procedure similar to those described for the synthesis of compound of Example 3.

Example 4

1-(3-(4-(Pyrimidin-2-yl)piperazine-1-carbonyl)benzyl)quinazoline-2,4(1H,3H)-dione White solid. $^1$H NMR (DMSO-$d_6$): 11.71 (s, 1H), 8.36 (d, J=4.8 Hz, 2H), 8.01 (d, J=6.9 Hz, 1H), 7.67-7.61 (m, 1H), 7.42-7.24 (m, 6H), 6.65 (t, J=4.8 Hz, 1H), 5.35 (s, 2H), 3.40-3.20 (m, 8H). MS: m/z 443.3 [M+H]$^+$.

Example 5

1-(3-(4-Cyclohexylpiperazine-1-carbonyl)benzyl)quinazoline-2,4(1H,3H)-dione

White solid. $^1$H NMR (DMSO-d$_6$): 11.74 (s, 1H), 8.00 (d, J=7.8 Hz, 1H), 7.62 (t, J=7.5 Hz, 1H), 7.43-7.38 (m, 2H), 7.26-7.20 (m, 4H), 5.33 (s, 2H), 3.40-3.20 (m, 4H), 2.21-2.15 (m, 4H), 1.96-1.70 (m, 5H), 1.21-1.08 (m, 6H). MS: m/z 447.3 [M+H]$^+$.

Example 6

1-(3-(4-([1,2,4]Triazolo[4,3-b]pyridazin-6-yl)piperazine-1-carbonyl)benzyl)quinazoline-2,4(1H,3H)-dione White solid. $^1$H NMR (DMSO-d$_6$): 11.73 (s, 1H), 9.24 (s, 1H), 8.12 (d, J=10.2 Hz, 1H), 8.02 (d, J=7.8 Hz, 1H), 7.66 (t, J=6.9 Hz, 1H), 7.42-7.24 (m, 7H), 5.36 (s, 2H), 3.40-3.20 (m, 8H). MS: m/z 483.3 [M+H]$^+$.

Example 7

1-(3-(4-Ethylpiperazine-1-carbonyl)benzyl)quinazoline-2,4(1H,3H)-dione

White solid. $^1$H NMR (DMSO-d$_6$): 11.72 (s, 1H), 8.01 (dd, J=7.8 and 1.2 Hz, 1H), 7.63 (t, J=8.0 Hz, 1H), 7.42-7.38 (m, 2H), 7.26-7.23 (m, 4H), 5.34 (s, 2H), 3.40-3.20 (m, 4H), 2.35-2.29 (m, 6H), 0.97 (t, J=7.1 Hz, 3H). MS: m/z 393.2 [M+H]$^+$.

Example 8

1-(3-(4-Benzoylpiperazine-1-carbonyl)benzyl)quinazoline-2,4(1H,3H)-dione

White solid. $^1$H NMR (DMSO-d$_6$): 11.71 (s, 1H), 7.97 (d, J=8.1 Hz, 1H), 7.60-7.56 (m, 1H), 7.45-7.18 (m, 11H), 5.34 (s, 2H), 3.40-3.20 (m, 8H). MS: m/z 469.3 [M+H]$^+$.

Example 9

1-(3-(4-(4-Fluorobenzoyl)piperazine-1-carbonyl)benzyl)quinazoline-2,4(1H,3H)-dione White solid. $^1$H NMR (DMSO-d$_6$): 11.71 (s, 1H), 7.99 (d, J=7.8 Hz, 1H), 7.60-7.19 (m, 1H), 5.34 (s, 2H), 3.60-3.20 (m, 8H). MS: m/z 487.3 [M+H]$^+$.

Example 10

1-(3-(4-(4-Chlorobenzoyl)piperazine-1-carbonyl)benzyl)quinazoline-2,4(1H,3H)-dione White solid. $^1$H NMR (DMSO-d$_6$): 11.73 (s, 1H), 7.98-7.97 (m, 1H), 7.63-7.57 (m, 1H), 7.48-7.19 (m, 10H), 5.33 (s, 2H), 3.75-3.15 (m, 8H). MS: m/z 503.2, 505.2 [M+H]$^+$.

Example 11

1-(3-(4-(4-Bromobenzoyl)piperazine-1-carbonyl)benzyl)quinazoline-2,4(1H,3H)-dione White solid. $^1$H NMR (DMSO-d$_6$): 11.74 (s, 1H), 8.02-7.95 (m, 2H), 7.68-7.59 (m, 2H), 7.40-7.15 (m, 8H), 5.35 (s, 2H), 3.40-3.20 (m, 8H). MS: m/z 547.2 [M+H]$^+$.

Example 12

1-(3-(4-(4-Methoxybenzoyl)piperazine-1-carbonyl)benzyl)quinazoline-2,4(1H,3H)-dione White solid. $^1$H NMR (DMSO-d$_6$): 11.73 (s, 1H), 7.99 (d, J=7.2 Hz, 1H), 7.70-7.50 (m, 1H), 7.40-7.29 (m, 6H), 7.21-7.18 (m, 2H), 6.99-6.96 (s, 2H), 5.33 (s, 2H), 3.77 (s, 3H), 3.56-3.15 (m, 8H). MS: m/z 499.3 [M+H]$^+$.

Example 13

1-(3-(4-(Tetrahydro-2H-pyran-4-carbonyl)piperazine-1-carbonyl)benzyl)quinazoline-2,4(1H,3H)-dione White solid. $^1$H NMR (DMSO-d$_6$): 11.74 (s, 1H), 8.02 (d, J=7.5 Hz, 1H), 7.65 (t, J=7.8 Hz, 1H), 7.45-7.38 (m, 2H), 7.32-7.23 (m, 4H), 5.36 (s, 2H), 3.86-3.82 (m, 2H), 3.75-3.10 (m, 10H), 2.90-2.80 (m, 1H), 1.64-1.48 (m, 4H). MS: m/z 477.3 [M+H]$^+$.

Example 14

1-(3-(4-(Cyclopentylcarbonyl)piperazine-1-carbonyl)benzyl)quinazoline-2,4(1H,3H)-dione White solid. $^1$H NMR (DMSO-d$_6$): 11.71 (s, 1H), 8.01 (d, J=6.9 Hz, 1H), 7.70-7.60 (m, 1H), 7.41-7.39 (m, 2H), 7.30-7.21 (m, 4H), 5.34 (s, 2H), 3.70-3.10 (m, 8H), 2.95-2.89 (m, 1H), 1.80-1.40 (m, 8H). MS: m/z 461.3 [M+H]$^+$.

Example 15

1-(3-(4-(Cyclopropylcarbonyl)piperazine-1-carbonyl)benzyl)quinazoline-2,4(1H,3H)-dione White solid. $^1$H NMR (DMSO-d$_6$): 11.71 (s, 1H), 8.01 (d, J=6.6 Hz, 1H), 7.63 (t, J=7.2 Hz, 1H), 7.41-7.21 (m, 6H), 5.34 (s, 2H), 3.80-3.15 (m, 8H), 1.94-1.91 (m, 1H), 0.72-0.69 (m, 4H). MS: m/z 433.2 [M+H]$^+$.

Example 16

1-(3-(4-(Ethylsulfonyl)piperazine-1-carbonyl)benzyl)quinazoline-2,4(1H,3H)-dione White solid. $^1$H NMR (DMSO-d$_6$): 11.74 (s, 1H), 8.01 (dd, J=7.8 and 1.2 Hz, 1H), 7.70-7.55 (m, 1H), 7.45-7.35 (m, 2H), 7.31-7.19 (m, 4H), 5.35 (s, 2H), 3.75-3.11 (m, 6H), 3.10-2.90 (m, 4H), 1.20 (t, J=7.4 Hz, 3H). MS: m/z 457.2 [M+H]$^+$.

Example 17

1-(3-(4-Acetylpiperazine-1-carbonyl)benzyl)quinazoline-2,4(1H,3H)-dione

White solid. $^1$H NMR (DMSO-d$_6$): 11.71 (s, 1H), 8.01 (d, J=6.6 Hz, 1H), 7.63 (t, J=7.2 Hz, 1H), 7.43-7.37 (m, 2H), 7.30-7.21 (m, 4H), 5.34 (s, 2H), 3.70-3.10 (m, 8H), 1.93 (s, 3H). MS: m/z 407.2 [M+H]$^+$.

Example 18

1-(3-(4-Phenylpiperidine-1-carbonyl)benzyl)quinazoline-2,4(1H,3H)-dione

White solid. $^1$H NMR (300M, DMSO-d$_6$): 11.75 (s, 1H), 7.99 (dd, J=7.8 and 1.2 Hz, 1H), 7.61 (t, J=7.2 Hz, 1H), 7.41-7.17 (m, 11H), 5.37 (s, 2H), 3.55-3.42 (m, 2H), 3.06-2.99 (m, 1H), 2.78-2.71 (m, 2H), 1.97-1.51 (m, 4H). MS: m/z 407.2 [M+H]$^+$.

Example 19

1-(3-(4-Phenylpiperazine-1-carbonyl)benzyl)quinazoline-2,4(1H,3H)-dione

White solid. $^1$H NMR (300M, DMSO-d$_6$): 11.75 (s, 1H), 8.03 (d, J=6.6 Hz, 1H), 7.67 (t, J=7.2 Hz, 1H), 7.46-7.39 (m, 2H), 7.34-7.21 (m, 6H), 6.93-6.91 (m, 2H), 6.81 (t, J=7.2 Hz, 1H), 5.37 (s, 2H), 3.85-2.85 (m, 8H). MS: m/z 441.3 [M+H]$^+$.

Example 20

1-(3-(4-(Pyrazin-2-yl)piperazine-1-carbonyl)benzyl) quinazoline-2,4(1H,3H)-dione White solid. $^1$H NMR (300 M, DMSO-d$_6$): 11.75 (s, 1H), 8.31 (s, 1H), 8.11 (s, 1H), 8.02 (d, J=7.8 Hz, 1H), 7.87 (d, J=2.7 Hz, 1H), 7.67 (t, J=7.2 Hz, 1H), 7.44-7.24 (m, 6H), 5.37 (s, 2H), 3.80-3.25 (m, 8H). MS: m/z 443.3 [M+H]$^+$.

Example 21

1-(4-Fluoro-3methoxycarbonylbenzyl)quinazoline-2, 4(1H,3H)-dione

The title compound was prepared from quinazoline-2,4 (1H,3H)-dione and methyl 5-(bromomethyl)-2-fluorobenzoate using a procedure similar to those described for the synthesis of compound of Example 1. $^1$H NMR (DMSO-d$_6$): 11.75 (s, 1H), 8.00 (d, J=7.8 Hz, 1H), 7.84 (d, J=6.9 Hz, 1H), 7.67-7.55 (m, 2H), 7.32-7.21 (m, 3H), 5.32 (s, 2H), 3.81 (s, 3H). MS: m/z 3.29 [M+H]$^+$.

Example 22

1-(3-Carboxy-4-fluorobenzyl)quinazoline-2,4(1H, 3H)-dione

The title compound was prepared from 1-(4-fluoro-3-methoxycarbonylbenzyl)quinazoline-2,4(1H,3)-dione using a procedure similar to those described for the synthesis of compound of Example 2. $^1$H NMR (DMSO-d$_6$): 13.23 (brs, 1H), 11.75 (s, 1H), 8.00 (d, J=7.5 Hz, 1H), 7.80 (dd, J=6.9 and 2.1 Hz, 1H), 7.67-7.54 (m, 2H), 7.30-7.21 (m, 3H), 5.31 (s, 2H). MS: m/z 315.3 [M+H]$^+$.

The following compounds were prepared from 1-(3-carboxy-4-fluorobenzyl)quinazoline-2,4(1H,3H)-dione and the corresponding substituted piperazine using a procedure similar to those described for the synthesis of compound of Example 3.

Example 23

1-(3-(4-(Cyclopentylcarbonyl)piperazine-1-carbonyl)-4-fluorobenzyl)quinazoline-2,4(1H,3H)-dione White solid. $^1$H NMR (300 M, DMSO-d$_6$): 11.73 (s, 1H), 8.00 (d, J=6.9 Hz, 1H), 7.64 (t, J=7.8 Hz, 1H), 7.43-7.21 (m, 5H), 5.30 (s, 2H), 3.56-2.97 (m, 8H), 2.89-2.84 (m, 1H), 1.80-1.40 (m, 8H). MS: m/z 479.3 [M+H]$^+$.

Example 24

1-(4-Fluoro-3-(4-(pyridin-2-yl)piperazine-1-carbonyl)benzyl)quinazoline-2,4(1H,3H)-dione White solid. $^1$H NMR (300 M, DMSO-d$_6$): 11.74 (s, 1H), 8.12 (d, J=3.3 Hz, 1H), 8.02 (d, J=6.6 Hz, 1H), 7.67 (t, J=8.4 Hz, 1H), 7.58-7.53 (m, 1H), 7.47-7.39 (m, 2H), 7.32-7.24 (m, 3H), 6.82 (d, J=8.4 Hz, 1H), 6.67 (t, J=6.9 Hz, 1H), 5.32 (s, 2H), 3.75-3.67 (m, 2H), 3.61-3.53 (m, 2H), 3.42-3.37 (m, 2H), 3.28-3.20 (m, 2H). MS: m/z 460.3 [M+H]$^+$.

Example 25

1-(4-Fluoro-3-(4-(pyrimidin-2-yl)piperazine-1-carbonyl)benzyl)quinazoline-2,4(1H,3H)-dione White solid. $^1$H NMR (300 M, DMSO-d$_6$): 11.72 (s, 1H), 8.37 (d, J=4.8 Hz, 2H), 8.00 (d, J=7.8 Hz, 1H), 7.65 (t, J=6.8 Hz, 1H), 7.48-7.38 (m, 2H), 7.30-7.22 (m, 3H), 6.66 (t, J=4.8 Hz, 1H), 5.31 (s, 2H), 3.70-3.10 (m, 8H). MS: m/z 461.3 [M+H]$^+$.

The following compounds were prepared from 1-(3-carboxybenzyl)quinazoline-2,4(1H,3H)-dione and the corresponding substituted piperazine or piperidine using a procedure similar to those described for the synthesis of compound of Example 3.

Example 26

1-(3-(4-(Cyclohexylcarbonyl)piperazine-1-carbonyl) benzyl)quinazoline-2,4(1H,3H)-dione $^1$H NMR (DMSO-d$_6$): 11.75 (s, 1H), 8.02 (d, J=7.8 Hz, 1H), 7.64 (t, J=7.2 Hz, 1H), 7.50-7.45 (m, 2H), 7.35-7.20 (m, 4H), 5.35 (s, 2H), 3.50-3.10 (m, 9H), 1.80-1.25 (m, 10H). MS: m/z 475.3 [M+H]$^+$.

Example 27

1-(3-(4-(Benzo[d]isothiazol-3-yl)piperazine-1-carbonyl)benzyl)quinazoline-2,4(1H,3H)-dione $^1$H NMR (DMSO-d$_6$): 11.75 (s, 1H), 8.08-8.06 (m, 2H), 8.01 (d, J=7.8 Hz, 1H), 7.87 (s, 1H), 7.67-7.54 (m, 2H), 7.48-7.30 (m, 5H), 7.27-7.20 (m, 2H), 5.37 (s, 2H), 3.80-3.31 (m, 8H). MS: m/z 498.3 [M+H]$^+$.

Example 28

1-(3-(4-(Piperidin-1-yl)piperidine-1-carbonyl)benzyl)quinazoline-2,4(1H,3H)-dione $^1$H NMR (DMSO-d$_6$): 11.76 (s, 1H), 8.03 (d, J=7.2 Hz, 1H), 7.65 (t, J=7.8 Hz, 1H), 7.42-7.21 (m, 6H), 5.41-5.32 (m, 2H), 3.10-2.60 (m, 9H), 1.90-1.30 (m, 10H). MS: m/z 447.3 [M+H]$^+$.

Example 29

1-(3-(4-(Pyridin-4-yl)piperazine-1-carbonyl)benzyl)
quinazoline-2,4(1H,3H)-dione $^1$H NMR (DMSO-d$_6$): 11.72 (s, 1H), 8.19 (d, J=6.6 Hz, 2H), 8.02 (d, J=6.3 Hz, 1H), 7.68-7.63 (m, 1H), 7.46-7.39 (m, 2H), 7.34-7.23 (m, 4H), 6.89 (d, J=6.6 Hz, 2H), 5.35 (s, 2H), 3.84-3.31 (m, 8H). MS: m/z 442.3 [M+H]$^+$.

Example 30

1-(3-(4-(Cyclobutylcarbonyl)piperazine-1-carbonyl)
benzyl)quinazoline-2,4(1H,3H)-dione $^1$H NMR (DMSO-d$_6$): 11.72 (s, 1H), 8.03 (d, J=6.4 Hz, 1H), 7.66 (t, J=7.8 Hz, 1H), 7.46-7.39 (m, 2H), 7.32-7.23 (m, 4H), 5.36 (s, 2H), 3.52-3.31 (m, 9H), 2.19-1.75 (m, 6H). MS: m/z 447.3 [M+H]$^+$.

Example 31

1-(3-(4-(6-Fluorobenzo[d]isoxazol-3-yl)piperidine-
1-carbonyl)benzyl)quinazoline-2,4(1H,3H)-dione $^1$H NMR (DMSO-d$_6$): 11.72 (s, 1H), 8.06 (dd, J=8.7 and 6.4 Hz, 1H), 7.95 (dd, J=7.8 and 1.5 Hz, 1H), 7.70 (dd, J=9.3 and 2.1 Hz, 1H), 7.64-7.59 (m, 1H), 7.46-7.14 (m, 7H), 5.36 (s, 2H), 3.45-3.28 (m, 5H), 2.10-2.04 (m, 1H), 1.99-1.94 (m, 3H). MS: m/z 499.3 [M+H]$^+$.

Example 32

1-(3-(4-(Thiophene-2-carbonyl)piperazine-1-carbonyl)benzyl)quinazoline-2,4(1H,3H)-dione $^1$H NMR (DMSO-d$_6$): 11.70 (s, 1H), 8.00 (dd, J=8.1 and 1.2 Hz, 1H), 7.76 (d, J=5.1 Hz, 1H), 7.64-7.59 (m, 1H), 7.44-7.11 (m, 8H), 5.34 (s, 2H), 3.81-3.40 (m, 8H). MS: m/z 475.2 [M+H]$^+$.

Example 33

1-(3-(4-(Furan-2-carbonyl)piperazine-1-carbonyl)
benzyl)quinazoline-2,4(1H,3H)-dione $^1$H NMR (DMSO-d$_6$): 11.72 (s, 1H), 8.02 (d, J=6.9 Hz, 1H), 7.86 (s, 1H), 7.65 (t, J=7.5 Hz, 1H), 7.50-7.15 (m, 6H), 7.00 (d, J=3.3 Hz, 1H), 6.70-6.60 (m, 1H), 5.37 (s, 2H), 3.85-3.20 (m, 8H). MS: m/z 459.2 [M+H]$^+$.

Example 34

1-(3-(4-(Furan-3-carbonyl)piperazine-1-carbonyl)
benzyl)quinazoline-2,4(1H,3H)-dione $^1$H NMR (DMSO-d$_6$): 11.71 (s, 1H), 8.15-7.90 (m, 2H), 7.73 (s, 1H), 7.62 (t, J=7.5 Hz, 1H), 7.50-7.10 (m, 6H), 6.64 (s, 1H), 5.34 (s, 2H), 3.80-3.10 (m, 8H). MS: m/z 459.3 [M+H]$^+$.

Example 35

1-(3-(4-(Thiophene-3-carbonyl)piperazine-1-carbonyl)benzyl)quinazoline-2,4(1H,3H)-dione $^1$H NMR (DMSO-d$_6$): 11.70 (s, 1H), 7.99 (d, J=7.5 Hz, 1H), 7.77 (s, 1H), 7.63-7.58 (m, 2H), 7.41-7.39 (m, 2H), 7.30-7.28 (m, 2H), 7.22-7.17 (m, 3H), 5.34 (s, 2H), 3.81-3.40 (m, 8H). MS: m/z 475.3 [M+H]$^+$.

Example 36

1-(3-(4-(Pyridine-3-carbonyl)piperazine-1-carbonyl)
benzyl)quinazoline-2,4(1H,3H)-dione $^1$H NMR (DMSO-d$_6$): 11.72 (s, 1H), 8.67 (dd, J=4.8 and 1.5 Hz, 1H), 8.61 (s, 1H), 8.01 (d, J=7.2 Hz, 1H), 7.82 (d, J=6.8 Hz, 1H), 7.52-7.20 (m, 8H), 5.36 (s, 2H), 3.52-3.31 (m, 8H). MS: m/z 470.3 [M+H]$^+$.

Example 37

1-(3-(4-(Pyridine-2-carbonyl)piperazine-1-carbonyl)
benzyl)quinazoline-2,4(1H,3H)-dione $^1$H NMR (DMSO-d$_6$): 11.78 (s, 1H), 8.68 (d, J=4.2 Hz, 1H), 8.20-7.95 (m, 2H), 7.68-7.27 (m, 9H), 5.43 (s, 2H), 3.90-3.50 (m, 8H). MS: m/z 470.3 [M+H]$^+$.

Example 38

1-(3-(4-(Pyridine-4-carbonyl)piperazine-1-carbonyl)
benzyl)quinazoline-2,4(1H,3H)-dione $^1$H NMR (DMSO-d$_6$): 11.62 (s, 1H), 8.58 (d, J=4.2 Hz, 2H), 7.91-7.89 (m, 1H), 7.57-7.44 (m, 1H), 7.29-7.10 (m, 8H), 5.25 (s, 2H), 3.80-2.75 (m, 8H). MS: m/z 470.3 [M+H]$^+$.

Example 39

1-(3-(4-Phenoxypiperidine-1-carbonyl)benzyl)quinazoline-2,4(1H,3H)-dione $^1$H NMR (DMSO-d$_6$): 11.67 (s, 1H), 7.95 (d, J=8.1 Hz, 1H), 7.57 (t, J=7.8 Hz, 1H), 7.38-7.30 (m, 2H), 7.27-7.14 (m, 6H), 6.92-6.85 (m, 3H), 5.30 (s, 2H), 4.58-4.52 (m, 1H), 3.90-3.10 (m, 4H), 1.95-1.35 (m, 4H). MS: m/z 456.3 [M+H]$^+$.

The following compounds were prepared from 1-(3-carboxy-4-fluorobenzyl)quinazoline-2,4(1H,3H)-dione and the corresponding substituted piperazine using a procedure similar to those described for the synthesis of compound of Example 3.

Example 40

1-(3-(4-(Cyclopropylcarbonyl)piperazine-1-carbonyl)-4-fluorobenzyl)quinazoline-2,4(1H,3H)-dione $^1$H NMR (DMSO-d$_6$): 11.72 (s, 1H), 8.01 (d, J=6.6 Hz, 1H), 7.65 (t, J=7.8 Hz, 1H), 7.39-7.22 (m, 5H), 5.31 (s, 2H), 3.52-3.31 (m, 8H), 2.01-1.86 (m, 1H), 0.73-0.70 (m, 4H). MS: m/z 451.3 [M+H]$^+$.

Example 41

1-(3-(4-(Cyclohexylcarbonyl)piperazine-1-carbonyl)-4-fluorobenzyl)quinazoline-2,4(1H,3H)-dione $^1$H NMR (DMSO-d$_6$): 11.71 (s, 1H), 8.00 (dd, J=7.8 and 1.2 Hz, 1H), 7.64 (t, J=7.4 Hz, 1H), 7.43-7.21 (m, 5H), 5.30 (s, 2H), 3.58-3.10 (m, 9H), 1.68-1.00 (m, 10H). MS: m/z 493.3 [M+H]$^+$.

Example 42

1-(4-Fluoro-3-(4-(pyrazin-2-yl)piperazine-1-carbonyl)benzyl)quinazoline-2,4(1H,3H)-dione $^1$H NMR (DMSO-d$_6$): 11.71 (s, 1H), 8.29 (s, 1H), 8.08 (s, 1H), 8.00 (d, J=7.8 Hz, 1H), 7.86 (d, J=2.1 Hz, 1H), 7.65 (t, J=7.5 Hz, 1H), 7.46-7.36 (m, 2H), 7.30-7.22 (m, 3H), 5.31 (s, 2H), 3.81-3.40 (m, 8J). MS: m/z 461.3 [M+H]$^+$.

Example 43

1-(3-(4-(Benzo[d]isothiazol-3-yl)piperazine-1-carbonyl)-4-fluorobenzyl)quinazoline-2,4(1H,3H)-dione $^1$H NMR (DMSO-d$_6$): 11.72. (s, 1H), 8.08-8.05 (m, 2H), 8.00 (dd, J=7.8 and 1.2 Hz, 1H), 7.64 (t, J=7.2 Hz, 1H), 7.56 (t, J=7.7 Hz, 1H), 7.46-7.41 (m, 3H), 7.31-7.19 (m, 3H), 5.31 (s, 2H), 3.87-3.81 (m, 2H), 3.49-3.31 (m, 6H). MS: m/z 516.2 [M+H]$^+$.

Example 44

1-(3-4-(Cyclobutylcarbonyl)piperazine-1-carbonyl)-4-fluorobenzyl)quinazoline-2,4(1H,3H)-dione $^1$H NMR (DMSO-d$_6$): 11.69 (s, 1H), 8.00 (d, J=7.8 Hz, 1H), 7.64 (t, J=8.0 Hz, 1H), 7.44-7.41 (m, 1H), 7.35 (d, J=5.7 Hz, 1H), 7.28-7.21 (m, 3H), 5.30 (s, 2H), 3.70-3.00 (m, 9H), 2.25-1.60 (m, 6H). MS: m/z, 465.3 [M+H]$^+$.

Example 45

1-(3-(4-Benzoylpiperazine-1-carbonyl)-4-fluorobenzyl)quinazoline-2,4(1H,3H)-dione $^1$H NMR (DMSO-d$_6$): 11.68 (s, 1H), 7.99 (d, J=7.8 Hz, 1H), 7.70-7.10 (m, 1), 5.30 (s, 2H), 3.80-3.10 (m, 8H). MS: m/z 487.3 [M+H]$^+$.

Example 46

1-(4-Fluoro-3-(4-(thiophene-2-carbonyl)piperazine-1-carbonyl)benzyl)quinazoline-2,4(1H,3H)-dione $^1$H NMR (DMSO-d$_6$): 11.67 (s, 1H), 8.00 (d, J=7.5 Hz, 1H), 7.75 (d, J=5.1 Hz, 1H), 7.62 (t, J=7.7 Hz, 1H), 7.50-7.15 (m, 6H), 7.12 (t, J=4.4 Hz, 1H), 5.30 (s, 2H), 3.80-3.10 (m, 8H). MS: m/z 493.2 [M+H]$^+$.

Example 47

1-(4-Fluoro-3-(4-(furan-2-carbonyl)piperazine-1-carbonyl)benzyl)quinazoline-2,4(1H,3H)-dione $^1$H NMR (DMSO-d$_6$): 11.69 (s, 1H), 8.00 (d, J=6.6 Hz, 1H), 7.83 (s, 1H), 7.64 (t, J=7.1 Hz, 1H), 7.50-7.35 (m, 2H), 7.30-7.15 (m, 3H), 6.99 (d, J=3.3 Hz, 1H), 6.70-6.55 (m, 1H), 5.31 (s, 2H), 3.85-3.10 (m, 8H). MS: m/z 477.3 [M+H]$^+$.

The following compounds were prepared from 1-(3-carboxy-6-fluorobenzyl)quinazoline-2,4(1H,3H)-dione (prepared from quinazoline-2,4(1H,3H)-dione and methyl 3-(bromomethyl)-4-fluorobenzoate using a procedure similar to those used for compounds of Example 1 and 2), and the corresponding substituted piperazine using a procedure similar to those described for the synthesis of compound of Example 3.

Example 48

1-(3-(4-(Cyclopentylcarbonyl)piperazine-1-carbonyl)-6-fluorobenzyl)quinazoline-2,4(1H,3H)-dione $^1$H NMR (DMSO-d$_6$): 11.75 (s, 1H), 8.03 (dd, J=7.8 and 1.2 Hz, 1H), 7.66 (t, J=7.8 Hz, 1H), 7.38-7.35 (m, 2H), 7.26 (t, J=7.7 Hz, 1H), 7.20-7.15 (m, 2H), 5.35 (s, 2H), 3.38-3.15 (m, 9H), 1.70-1.55 (m, 8H). MS: m/z 479.3 [M+H]$^+$.

Example 49

1-(3-(4-(Cyclohexylcarbonyl)piperazine-1-carbonyl)-6-fluorobenzyl)quinazoline-2,4(1H,3H)-dione $^1$H NMR (DMSO-d$_6$): 11.75 (s, 1), 8.04 (d, J=7.8 Hz, 1H), 7.67 (d, J=7.4 Hz, 1H), 7.50-7.10 (m, 5H), 5.37 (s, 2H), 3.70-2.90 (m, 9H), 1.80-1.00 (m, 10H). MS: m/z 493.3 [M+H]$^+$.

Example 50

1-(6-Fluoro-3-(4-(pyrimidin-2-yl)piperazine-1-carbonyl)benzyl)quinazoline-2,4(1H,3H)-dione $^1$H NMR (DMSO-d$_6$): 11.71 (s, 1H), 8.35 (d, J=4.5 Hz, 2H), 8.01 (d, J=7.6 Hz, 1H), 7.67 (t, J=8.4 Hz, 1H), 7.40-7.17 (m, 5H), 6.64 (t, J=4.8 Hz, 1H), 5.35 (s, 2H), 3.81-3.14 (m, 8H). MS: m/z 461.2 [M+H]$^+$.

Example 51

1-(6-Fluoro-3-(4-(pyridin-2-yl)piperazine-1-carbonyl)benzyl)quinazoline-2,4(1H,3H)-dione $^1$H NMR (DMSO-d$_6$): 11.72 (s, 1H), 8.12 (d, J=3.3 Hz, 1H), 8.03 (d, J=6.6 Hz, 1H), 7.70 (t, J=8.0 Hz, 1H), 7.56 (t, J=8.0 Hz, 1H), 7.42-7.18 (m, 5H), 6.76 (d, J=8.4 Hz, 1H), 6.67 (dd, J=6.9 and 5.1 Hz, 1H), 5.38 (s, 2H), 3.70-3.00 (m, 8H). MS: m/z 460.3 [M+H]$^+$.

Example 52

1-(6-Fluoro-3-(4-(thiophene-2-carbonyl)piperazine-1-carbonyl)benzyl)quinazoline-2,4(1H,3H)-dione $^1$H NMR (DMSO-d$_6$): 11.71 (s, 1H), 8.01 (d, J=8.1 Hz, 1H), 7.76 (d, J=4.8 Hz, 1H), 7.62 (t, J=7.8 Hz, 1H), 7.43-7.32 (m, 3H), 7.22-7.12 (m, 4H), 5.35 (s, 2H), 3.80-2.90 (m, 8H). MS: m/z 493.2 [M+H]$^+$.

Example 53

1-(3-(4-(Cyclobutylcarbonyl)piperazine-1-carbonyl)-6-fluorobenzyl)quinazoline-2,4(1H,3H)-dione $^1$H NMR (DMSO-d$_6$): 11.71 (s, 1H), 8.02 (d, J=7.8 Hz, 1H), 7.65 (t, J=8.0 Hz, 1H), 7.36-7.13 (m, 5H), 5.34 (s, 2H), 3.60-2.80 (m, 9H), 2.20-1.70 (m, 6H). MS: m/z 465.3 [M+H]$^+$.

Example 54

1-(6-Fluoro-3-(4-(furan-2-carbonyl)piperazine-1-carbonyl)benzyl)quinazoline-2,4(1H,3H)-dione $^1$H NMR (DMSO-d$_6$): 11.71 (s, 1H), 8.01 (d, J=6.6 Hz, 1H), 7.84 (s, 1H), 7.64 (t, J=7.5 Hz, 1H), 7.43-7.32 (m, 2H), 7.25-7.16 (m, 3H), 6.96 (d, J=3.0 Hz, 1H), 7.63-6.62 (m, 1H), 5.35 (s, 2H), 3.80-2.90 (m, 8H). MS: m/z 477.3 [M+H]$^+$.

The following compounds were prepared from 1-(3-carboxy-6-chlorobenzyl)quinazoline-2,4(1H,3H)-dione (prepared From quinazoline-2,4(1H,3H)-dione and methyl 3-(bromomethyl)-4-chlorobenzoate using a procedure similar to those for compounds of Example 1 and 2), and the corresponding substituted piperazine using a procedure similar to those described for the synthesis of compound of Example 3.

Example 55

1-(6-Chloro-3-(4-(cyclopentylcarbonyl)piperazine-1-carbonyl)benzyl)quinazoline-2,4(1H,3H)-dione $^1$H NMR (DMSO-d$_6$): 11.75 (s, 1H), 8.05 (d, J=7.8 Hz, 1H), 7.69-7.64 (m, 2H), 7.37 (d, J=8.1 Hz, 1H), 7.28 (t, J=7.3 Hz, 1H), 7.08-7.02 (m, 2H), 5.33 (s, 2H), 3.70-2.80 (m, 9H), 1.80-1.55 (m, 8H). MS: m/z 495.3 [M+H]$^+$.

Example 56

1-(6-Chloro-3-(4-(pyrimidin-2-yl)piperazine-1-carbonyl)benzyl)quinazoline-2,4(1H,3H)-dione $^1$H NMR (DMSO-d$_6$): 11.71 (s, 1H), 8.36 (d, J=4.8 Hz, 2H), 8.03 (d, J=6.6 Hz, 1H), 7.69-7.64 (m, 2H), 7.38 (d, J=6.9 Hz, 1H), 7.28 (t, J=7.5 Hz, 1H), 7.09-7.04 (m, 2H), 6.65 (t, J=4.8 Hz, 1H), 5.33 (s, 2H), 3.80-3.00 (m, 8H). MS: m/z 477.2 [M+H]$^+$.

Example 57

1-(6-Chloro-3-(4-(cyclohexylcarbonyl)piperazine-1-carbonyl)benzyl)quinazoline-2,4(1H,3H)-dione $^1$H NMR (DMSO-d$_6$): 11.71 (s, 1H), 8.02 (d, J=7.5 Hz, 1H), 7.75-7.55 (m, 2H), 7.34 (d, J=8.1 Hz, 1H), 7.25 (t, J=7.5 Hz, 1H), 7.10-6.90 (m, 2H), 5.30 (s, 2H), 3.60-2.80 (m, 9H), 1.80-1.00 (m, 10H). MS: m/z 509.3 [M+H]$^+$.

Example 58

1-(6-Chloro-3-(4-(pyridin-2-yl)piperazine-1-carbonyl)benzyl)quinazoline-2,4(1H,3H)-dione $^1$H NMR (DMSO-d$_6$): 11.73 (s, 1H), 8.11 (d, J=3.6 Hz, 1H), 8.03 (d, J=7.8 Hz, 1H), 7.80-7.60 (m, 2H), 7.55 (t, J=6.9 Hz, 1H), 7.39 (d, J=6.6 Hz, 1H), 7.30 (t, J=7.5 Hz, 1H), 7.15-7.00 (m, 2H), 6.72 (d, J=8.4 Hz, 1H), 6.66 (dd, J=6.8 and 5.0 Hz, 1H), 5.34 (s, 2H), 3.70-3.00 (m, 8H). MS: m/z 476.2 [M+H]$^+$.

The following compounds were prepared from 1-(3-carboxyl-2-chlorobenzyl)quinazoline-2,4(1H,3H)-dione (prepared from quinazoline-2,4(1H,3H)-dione and methyl 3-bromomethyl)-2-chlorobenzoate using a procedure similar to those used for compounds of Example 1 and 2), and the corresponding substituted piperazine using a procedure similar to those described for the synthesis of compound of Example 3.

Example 59

1-(2-Chloro-3-(4-(cyclopentylcarbonyl)piperazine-1-carbonyl)benzyl)quinazoline-2,4(1H,3H)-dione $^1$H NMR (DMSO-d$_6$): 11.78 (s, 1H), 8.07 (d, J=7.8 Hz, 1H), 7.67 (t, J=7.5 Hz, 1H), 7.45-7.20 (m, 3H), 7.15-6.95 (m, 2H), 5.50-5.15 (m, 2H), 3.80-3.10 (m, 8H), 3.04-2.94 (m, 1H), 1.90-1.35 (m, 8H). MS: m/z 495.3 [M+H]$^+$.

Example 60

1-(2-Chloro-3-(4-(pyrimidin-2-yl)piperazine-1-carbonyl)benzyl)quinazoline-2,4(1H,3H)-dione $^1$H NMR (DMSO-d$_6$): 11.88 (s, 1H), 8.49 (d, J=4.8 Hz, 2H), 8.16 (d, J=7.8 Hz, 1H), 7.77 (t, J=7.8 Hz, 1H), 7.50-7.30 (m, 3H), 7.25-7.05 (m, 2H), 6.78 (t, J=7.7 Hz, 1H), 5.60-5.30 (m, 2H), 4.10-3.70 (m, 8H). MS: m/z 477.2 [M+H]$^+$.

The following compounds were prepared from 1-(3-carboxy-2-fluorobenzyl)quinazoline-2,4(1H,3H)-dione (prepared from quinazoline-2,4(1H,3H)-dione and methyl 3-(bromomethyl)-2-fluorobenzoate using a procedure similar to those used for compounds of Example 1 and 2), and the corresponding substituted piperazine using a procedure similar to those described for the synthesis compound of Example 3.

Example 61

1-(2-Fluoro-3-(4-(pyrimidin-2-yl)piperazine-1-carbonyl)benzyl)quinazoline-2,4(1H,3H)-dione $^1$H NMR (DMSO-d$_6$): 11.71 (s, 1H), 8.37 (d, J=4.8 Hz, 2H), 8.03 (d, J=6.6 Hz, 1H), 7.66 (t, J=7.1 Hz, 1H), 7.45-7.05 (m, 5H), 6.66 (t, J=4.7 Hz, 1H), 5.35 (s, 2H), 3.90-3.60 (m, 8H). MS: m/z 461.3 [M+H]$^+$.

Example 62

1-(3-(4-(Cyclopentylcarbonyl)piperazine-1-carbonyl)-2-fluorobenzyl)quinazoline-2,4(1H,3H)-dione $^1$H NMR (DMSO-d$_6$): 11.74 (s, 1H), 8.03 (d, J=7.5 Hz, 1H), 7.66 (t, J=7.7 Hz, 1H), 7.40-7.10 (m, 5H), 5.34 (s, 2H), 3.80-3.20 (m, 8H), 3.10-2.80 (m, 1H), 1.90-1.40 (m, 8H). MS: m/z 479.3 [M+H]$^+$.

The following compounds were prepared from 1-(3-carboxy-5-fluorobenzyl)quinazoline-2,4(1H,3H)-dione (prepared from quinazoline-2,4(1H,3H)-dione and methyl 3-(bromomethyl)-5-fluorobenzoate using a procedure similar to those used for compounds of Example 1 and 2), and the corresponding substituted piperazine using a procedure similar to those described for the synthesis compound of Example 3.

Example 63

1-(5-Fluoro-3-(4-(pyrimidin-2-yl)piperazine-1-carbonyl)benzyl)quinazoline-2,4(1H,3H)-dione $^1$H NMR (DMSO-d$_6$): 11.68 (s, 1H), 8.36 (d, J=4.8 Hz, 2H), 8.00 (d, J=7.8 Hz, 1H), 7.64 (t, J=8.0 Hz, 1H), 7.30-7.15 (m, 5H), 6.64 (t, J=4.8 Hz, 1H), 5.34 (s, 2H), 3.80-3.50 (m, 8H). MS: m/z 461.3 [M+H]$^+$.

Example 64

1-(3-(4-(Cyclopentylcarbonyl)piperazine-1-carbonyl)-5-fluorobenzyl)quinazoline-2,4(1H,3H)-dione

$^1$H NMR (DMSO-d$_6$): 11.69 (s, 1H), 8.00 (d, J=9.0 Hz, 1H), 7.64 (t, J=7.1 Hz, 1H), 7.31-7.15 (m, 5H), 5.34 (s, 2H), 3.70-3.10 (m, 8H), 2.94-2.86 (m, 1H), 1.80-1.40 (m, 8H). MS: m/z 479.3 [M+H]$^+$.

The following compounds were prepared from 1-(3-carboxy-4-chlorobenzyl)quinazoline-2,4(1H,3H)-dione (prepared from quinazoline-2,4(1H,3H)-dione and methyl 5-(bromomethyl)-2-chlorobenzoate using a procedure similar to those used for compounds of Example 1 and 2), and the corresponding substituted piperazine using a procedure similar to those described for the synthesis compound of of Example 3.

Example 65

1-(4-Chloro-3-(4-(pyrimidin-2-yl)piperazine-1-carbonyl)benzyl)quinazoline-2,4(1H,3H)-dione

$^1$H NMR (CD$_3$OD): 8.38 (d, J=4.6 Hz, 2H), 8.16 (d, J=9.0 Hz, 1H), 7.69 (t, J=8.7 Hz, 1H), 7.54-7.29 (m, 5H), 6.67 (t, J=4.6 Hz, 1H), 5.51-5.39 (m, 2H), 3.98-3.57 (m, 8H). MS: m/z 477.2 [M+H]$^+$.

Example 66

1-(4-Chloro-3-(4-(cyclohexycarbonyl)piperazine-1-carbonyl)benzyl)quinazoline-2,4(1H,3H)-dione

$^1$H NMR (DMSO-d$_6$): 11.60 (s, 1H), 7.91 (d, J=7.8 Hz, 1H), 7.53 (t, J=7.5 Hz, 1H), 7.39 (d, J=9.0 Hz, 1H), 7.28-7.26 (m, 2H), 7.16-7.07 (m, 2H), 5.31-5.13 (m, 2H), 3.48-2.90 (m, 9H), 1.59-1.09 (m, 10H). MS: m/z 509.3 [M+H]$^+$.

The following compounds were prepared from 1((2-carboxy-furan-5-yl)methyl)quinazoline-2,4(1H,3H)-dione (prepared from quinazoline-2,4(1H,3H)-dione and ethyl 5-(chloromethyl)furan-2-carboxylate using a procedure similar to those described for the synthesis of compounds of Example 1 and 2), and the corresponding substituted piperazine using procedure similar to those described for the synthesis of compound of Example 3.

Example 67

1-((2-(4-(Cyclopentylcarbonyl)piperazine-1-carbonyl)furan-5-yl)methyl)quinazoline-2,4(1H,3H)-dione

$^1$H NMR (DMSO-d$_6$): 11.75 (s, 1H), 8.01 (d, J=7.5 Hz, 1H), 7.74 (t, J=7.5 Hz, 1H), 7.57 (d, J=8.1 Hz, 1H), 7.28 (t, J=7.5 Hz, 1H), 6.96 (d, J=3.3 Hz, 1H), 6.59 (d, J=3.3 Hz, 1H), 5.36 (s, 2H), 3.61-3.14 (m, 9H), 1.73-1.54 (m, 8H). MS: m/z 451.3 [M+H]$^+$.

Example 68

1-((2-(4-(Benzo[d]isothiazol-3-yl)piperazine-1-carbonyl)furan-5-yl)methyl)quinazoline-2,4(1H,3H)-dione

$^1$H NMR (DMSO-d$_6$): 11.74 (s, 1H), 8.10-8.08 (m, 2H), 8.02 (d, J=7.8 Hz, 1H), 7.76 (t, J=4.5 Hz, 1H), 7.61-7.57 (m, 2H), 7.48 (t, J=7.5 Hz, 1H), 7.30-7.25 (m, 1H), 7.00 (d, J=3.3 Hz, 1H), 6.60 (d, J=3.3 Hz, 1H), 5.39 (s, 2H), 3.85-3.78 (m, 4H), 3.49-3.40 (m, 4H). MS: m/z 488.2 [M+H]$^+$.

The following compounds were prepared from 1-((2-carboxylpyridin-6-yl)methyl)quinazoline-2,4(1H,3H)-dione (prepared from quinazoline-2,4(1H,3H)-dione and methyl 6-(bromomethyl)pyridine-2-carboxylate using a procedure similar to those described for the synthesis of compounds of Example 1 and 2), and the corresponding substituted piperazine using a procedure similar to those described for the synthesis of compound of Example 3.

Example 69

1-((2-(4-(Cyclopentylcarbonyl)piperazine-1-carbonyl)pyridin-6-yl)methyl)quinazoline-2,4(1H,3H)-dione

$^1$H NMR (CD$_3$OD): 8.16 (d, J=6.3 Hz, 1H), 7.98-7.96 (m, 1H), 7.64-7.59 (m, 3H), 7.32-7.26 (m, 2H), 5.57 (s, 2H), 3.70-3.58 (m, 4H), 3.31-2.92 (m, 5H), 1.84-1.70 (m, 8H). MS: m/z 462.3 [M+H]$^+$.

Example 70

1-((2-(4-(Pyridin-2-yl)piperazine-1-carbonyl)pyridin-6-yl)methyl)quinazoline-2,4(1H,3H)-dione

$^1$H NMR (CD$_3$OD): 8.15-8.12 (m, 2H), 7.96 (t, J=7.5 Hz, 1H), 7.67-7.58 (m, 4H), 7.30-7.25 (m, 2H), 6.80-6.71 (m, 2H), 5.57 (s, 2H), 3.81-3.78 (m, 2H), 3.59-3.55 (m, 2H), 3.44-3.41 (m, 2H), 3.23-3.19 (m, 2H). MS: m/z 443.3 [M+H]$^+$.

Example 71

1-((2-(4-(Pyrimidin-2-yl)piperazine-1-carbonyl)pyridin-6-yl)methyl)quinazoline-2,4(1H,3H)-dione

$^1$H NMR (CD$_3$OD): 8.36 (d, J=4.8 Hz, 2H), 8.14 (d, J=6.9 Hz, 1H), 7.96 (t, J=7.5 Hz, 1H), 7.65-7.58 (m, 3H), 7.31-7.28 (m, 2H), 6.64 (t, J=4.8 Hz, 1H), 5.57 (s, 2H), 3.85-3.82 (m, 2H), 3.78-3.73 (m, 2H), 3.57-3.53 (m, 2H), 3.39-3.35 (m, 2H). MS: m/z 444.3 [M+H]$^+$.

The following compounds were prepared from 1-(3-carboxybenzyl)quinazoline-2,4(1H,3H)-dione and the corresponding substituted piperazine using a procedure similar to those described for the synthesis of compound of Example 3.

Example 72

1-(3-(4-(Thiazol-2-yl)piperazine-1-carbonyl)benzyl)quinazoline-2,4(1H,3H)-dione

$^1$H NMR (DMSO-d$_6$): 11.72 (s, 1H), 8.03 (d, J=7.3 Hz, 1H), 7.66 (t, J=7.7 Hz, 1H), 7.46-7.23 (m, 6H), 7.18 (d, J=3.6 Hz, 1H), 6.88 (d, J=3.6 Hz, 1H), 5.37 (s, 2H), 3.80-3.40 (m, 8H). MS: m/z 448.3 [M+H]$^+$.

Example 73

1-(3-(4-(Cyclohexylmethyl)piperazine-1-carbonyl)benzyl)quinazoline-2,4(1H,3H)-dione

$^1$H NMR (DMSO-d$_6$): 11.75 (s, 1H), 8.02 (dd, J=8.0 and 1.4 Hz, 1H), 7.67-7.62 (m, 1H), 7.41-7.39 (m, 2H), 7.27-

7.23 (m, 4H), 5.35 (s, 2H), 3.54-3.15 (m, 4H), 2.32-2.03 (m, 6H), 1.73-1.44 (m, 5H), 1.23-1.06 (m, 6H). MS: m/z 461.3 [M+H]$^+$.

Example 74

1-(3-(4-(Cyclopentylmethyl)piperazine-1-carbonyl) benzyl)quinazoline-2,4(1H,3H)-dione $^1$H NMR (DMSO-d$_6$): 11.73 (s, 1H), 8.03 (d, J=7.5 Hz, 1H), 7.65 (d, J=7.5 Hz, 1H), 7.42-7.23 (m, 6H), 5.36 (s, 2H), 3.54-2.87 (m, 6H), 2.25-2.20 (m, 4H), 1.80-1.24 (m, 9H). MS: m/z 447.3 [M+H]$^+$.

Example 75

1-(3-(4-(Cyclohexysulfonyl)piperazine-1-carbonyl) benzyl)quinazoline-2,4(1H,3H)-dione $^1$H NMR (DMSO-d$_6$): 11.69 (s, 1H), 8.01 (dd, J=8.0 and 1.4 Hz, 1H), 7.64-7.60 (m, 1H), 7.42-7.38 (m, 2H), 7.29-7.16 (m, 4H), 5.35 (s, 2H), 3.56-3.52 (m, 2H), 3.20-3.05 (m, 6H), 1.96-1.93 (m, 1H), 1.80-1.76 (m, 2H), 1.62-1.58 (m, 2H), 1.27-1.22 (m, 6H). MS: m/z 511.3 [M+H]$^+$.

Example 76

7-Fluoroquinazoline-2,4(1H,3H)-dione

To a mixture of 2-amino-4-fluorobenzoic acid (4.0 g, 26 mmol) and potassium cyanate (3.5 g, 43 mmol) in water (200 mL) was added acetic acid (3 mL, 45 mmol) and the mixture was stirred at room temperature for about 5 h. To the mixture was added NaOH (15 g, 375 mmol) and it was stirred for another 1 h. The mixture was filtered and the solid was mixed in hot water, and it was adjusted to pH=5-6 by addition of acetic acid. The mixture was filtered and washed with water, dried to give the title compound (3.0 g, 65% yield) as gray solid. MS: m/z 181.1. [M+H]$^+$.

The following compounds were prepared from 1-(3-carboxybenzyl)-7-fluoroquinazoline-2,4(1H,3H)-dione (prepared from 7-fluoroquinazoline-2,4(1H,3H)-dione and methyl 3-bromomethyl)benzoate using a procedure similar to those for compounds of Example 1 and 2), and the corresponding substituted piperazine using a procedure similar to those described for the synthesis of compound of Example 3.

Example 77

1-(3-(4-(Cyclopentylcarbonyl)piperazine-1-carbonyl)benzyl)-7-fluoroquinazoline-2,4(1H,3H)-dione $^1$H NMR (DMSO-d$_6$): 11.81 (s, 1H), 8.08 (t, J=7.6 Hz, 1H), 7.44-7.31 (m, 4H), 7.18-7.12 (m, 2H), 5.34 (s, 2H), 3.70-2.80 (m, 9H), 1.80-1.55 (m, 8H). MS: m/z 479.3 [M+H]$^+$.

Example 78

7-Fluoro-1-(3-(4-(pyrimidin-2-yl)piperazine-1-carbonyl)benzyl)quinazoline-2,4(1H,3H)-dione $^1$H NMR (DMSO-d$_6$): 11.79 (s, 1H), 8.37 (cd, J=4.8 Hz, 2H), 8.05 (t, J=7.6 Hz, 1H), 7.45-7.31 (m, 4H), 7.17-7.07 (m, 2H), 6.65 (t, J=4.8 Hz, 1H), 5.33 (s, 2H), 3.78-3.55 (m, 8H). MS: m/z 461.3 [M+H]$^+$.

The following compounds were prepared from 1-(3-carboxybenzyl)-7-methylquinazoline-2,4(1H,3H)-dione (prepared from 7-methylquinazoline-2,4(1H,3H)-dione and methyl 3-(bromomethyl)benzoate using a procedure similar to those for compounds of Example 1 and 2), and the corresponding substituted piperazine using a procedure similar to those described for the synthesis of compound of Example 3.

Example 79

1-(3-(4-(Cyclopentylcarbonyl)piperazine-1-carbonyl)benzyl)-7-methylquinazoline-2,4(1H,3H)-dione $^1$H NMR (CD$_3$OD): 8.04 (d, J=8.1 Hz, 1H), 7.51-7.49 (m, 2H), 7.40-7.38 (m, 2H), 7.15-7.11 (m, 2H), 5.45 (s, 2H), 3.75-3.50 (m, 8H), 3.12-3.09 (m, 1H), 2.39 (s, 3H), 1.88-1.64 (m, 8H). MS: m/z 475.3 [M+H]$^+$.

Example 80

7-Methyl-1-(3-(4-(pyrimidin-2-yl)piperazine-1-carbonyl)benzyl)quinazoline-2,4(1H,3H)-dione $^1$H NMR (CD$_3$OD): 8.38-8.36 (m, 2H), 8.04 (d, J=7.8 Hz, 1H), 7.52-7.50 (m, 2H), 7.42-7.40 (m, 2H), 7.16-7.13 (m, 2H), 6.66 (t, J=4.8 Hz, 1H), 5.46 (s, 2H), 3.92-3.56 (m, 8H), 2.40 (s, 3H). MS: m/z 457.3 [M+H]$^+$.

The following compounds were prepared from 1-(3-carboxybenzyl)-6-methylquinazoline-2,4(1H,3H)-dione (prepared from 6-methylquinazoline-2,4(1H,3H)-dione and methyl 3-(bromomethyl)benzoate using a procedure similar to those for compounds of Example 1 and 2), and the corresponding substituted piperazine using a procedure similar to those described for the synthesis of compound of Example 3.

Example 81

6-Methyl-1-(3-(4-(pyrimidin-2-yl)piperazine-1-carbonyl)benzyl)quinazoline-2,4(1H,3H)-dione $^1$H NMR (CD$_3$OD): 8.34 (d, J=4.8 Hz, 2H), 7.94 (s, 1H), 7.49-7.47 (m, 3H), 7.39-7.34 (m, 2H), 7.18 (d, J=8.4 Hz, 1H), 6.64 (t, J=4.8 Hz, 1H), 5.44 (s, 2H), 3.89-3.39 (m, 8H), 2.39 (s, 3H). MS: m/z 457.3 [M+H]$^+$.

Example 82

1-(3-(4-(Cyclopentylcarbonyl)piperazine-1-carbonyl)benzyl)-6-methylquinazoline-2,4(1H,3H)-dione $^1$H NMR (CD$_3$OD): 7.95 (s, 1H), 7.49-7.47 (m, 3H), 7.38-7.35 (m, 2H), 7.18 (d, J=8.7 Hz, 1H), 5.43 (s, 2H), 3.71-3.69 (m, 4H), 3.49-3.47 (m, 4H), 3.09-3.08 (m, 1H), 2.39 (s, 3H), 1.88-1.63 (m, 8H). MS: m/z 475.3 [M+H]$^+$.

The following compounds were prepared from 1-(3-carboxy-4-fluorobenzyl)-6-methylquinazoline-2,4(1H,3H)-dione prepared from 6-methylquinazoline-2,4(1H,3H)-dione and methyl 5-(bromomethyl)-2-fluorobenzoate using a procedure similar to those for compounds of Example 1 and 2), and the corresponding substituted piperazine using a procedure similar to those described for the synthesis compound of Example 3.

Example 83

1-(4-Fluoro-3-(4-(pyrimidin-2-yl)piperazine-1-carbonyl)benzyl)-6-methylquinazoline-2,4(1H,3H)-dione $^1$H NMR (CD$_3$OD): 8.37 (d, J=4.8 Hz, 2H), 7.96 (s, 1H), 7.54-7.51 (m, 2H), 7.40 (dd, J=6.3 and 2.1 Hz, 1H), 7.28-7.21 (m, 2H), 6.66 (t, J=4.8 Hz, 1H), 5.41 (s, 2H), 3.93-3.56 (m, 8H), 2.41 (s, 3H). MS: m/z 475.3 [M+H]$^+$.

Example 84

1-(3-(4-(Cyclohexylcarbonyl)piperazine-1-carbonyl)-4-fluorobenzyl)-6-methylquinazoline-2,4(1H,3H)-dione $^1$H NMR (DMSO-d$_6$): 11.54 (s, 1H), 7.71 (s, 1H), 7.38-7.24 (m, 3H), 7.16 (t, J=9.0 Hz, 1H), 7.04 (d, J=8.7 Hz, 1H), 5.19 (s, 2H), 3.45-2.99 (m, 9H), 2.22 (s, 3H), 1.59-1.49 (m, 5H), 1.22-1.13 (m, 5H). MS: m/z 507.3 [M+H]$^+$.

Example 85

1-(3-(4-(Cyclopentylcarbonyl)piperazine-1-carbonyl)-4-fluorobenzyl)-6-methylquinazoline-2,4(1H,3H)-dione $^1$H NMR (DMSO-d$_6$): 11.63 (s, 1H), 7.80 (s, 1H), 7.46-7.22 (m, 4H), 7.12 (d, J=8.4 Hz, 1H), 5.27 (s, 2H), 3.35-2.97 (m, 8H), 2.99-2.84 (m, 1H), 2.30 (s, 3H), 1.73-1.49 (m, 8H). MS: m/z 493.3 [M+H]$^+$.

The following compounds were prepared from 6-bromo-1-(3-carboxybenzyl)quinazoline-2,4(1H,3H)-dione (prepared from 6-bromoquinazoline-2,4(1H,3H)-dione and methyl 3-(bromomethyl)benzoate using a procedure similar to those for compounds of Example 1 and 2), and the corresponding substituted piperazine using a procedure similar to those described for the synthesis of compound of Example 3.

Example 86

6-Bromo-1-(3-(4-(cyclohexylcarbonyl)piperazine-1-carbonyl)benzyl)quinazoline-2,4(1H,3H)-dione $^1$H NMR (DMSO-d$_6$): 11.86 (s, 1H), 8.05 (d, J=2.4 Hz, 1H), 7.79 (dd, J=9.0 and 2.4 Hz, 1H), 7.40-7.38 (m, 2H), 7.30-7.27 (m, 2H), 7.16 (d, J=9.0 Hz, 1H), 5.32 (s, 2H), 3.80-3.11 (m, 9H), 1.68-1.59 (m, 5H), 1.32-1.19 (m, 5H). MS: m/z 553.3 [M+H]$^+$.

Example 87

6-Bromo-1-(3-(4-(cyclopentylcarbonyl)piperazine-1-carbonyl)benzyl)quinazoline-2,4(1H,3H)-dione $^1$H NMR (DMSO-d$_6$): 11.86 (s, 1H), 8.04 (d, J=2.4 Hz, 1H), 7.86 (dd, J=9.0 and 2.4 Hz, 1H), 7.41-7.38 (m, 2H), 7.29-7.27 (m, 2H), 7.15 (d, J=8.7 Hz, 1H), 5.32 (s, 2H), 3.57-2.90 (m, 9H), 1.71-1.51 (m, 8H). MS: m/z 539.2 [M+H]$^+$.

Example 88

6-Bromo-1-(3-(4-(pyrimidin-2-yl)piperazine-1-carbonyl)benzyl)quinazoline-2,4(1H,3H)-dione $^1$H NMR (CD$_3$OD): 8.38 (d, J=4.8 Hz, 2H), 8.25-8.24 (m, 1H), 7.78 (dd, J=8.9 and 2.3 Hz, 1H), 7.52-7.50 (m, 2H), 7.42-7.41 (m, 2H), 7.25 (d, J=9.3 Hz, 1H), 6.66 (t, J=4.6 Hz, 1H), 5.45 (s, 2H), 3.93-3.40 (m, 8H). MS: m/z 521.2 [M+H]$^+$.

Example 89

6-Nitroquinazoline-2,4(1H,3H)-dione

A mixture of 2-amino-5-nitrobenzoic acid (0.588 g, 3.23 mmol) and urea (1.164 g, 19.38 mmol) was heated at 200° C. under N$_2$ for 1 h. The mixture was cooled to room temperature and 4 M NaOH was added until pH=14. It was acidified to pH=5.0 via addition of AcOH. The mixture was filtered and the yellow solid was dried to give the title compound (0.49 g, 72.8%) as a yellow solid. MS: m/z 208.1 [M+H]$^+$.

The following compounds were prepared from 1-(3-carboxybenzyl)-6-nitroquinazoline-2,4(1H,3H)-dione (prepared from 6-nitroquinazoline-2,4(1H,3H)-dione and methyl 3-(bromomethyl)benzoate using a procedure similar to those for compounds of Example 1 and 2), and the corresponding substituted piperazine using a procedure similar to those described for the synthesis of compound of Example 3.

Example 90

1-(3-(4-(Cyclopentylcarbonyl)piperazine-1-carbonyl)benzyl)-6-nitroquinazoline-2,4(1H,3H)-dione $^1$H NMR (DMSO-d$_6$): 12.22 (s, 1H), 8.77 (d, J=2.4 Hz, 1H), 8.51 (dd, J=9.3 and 2.4 Hz, 1H), 7.52-7.46 (m, 3H), 7.43-7.39 (m, 2H), 5.50 (s, 2H), 3.58-2.96 (m, 9H), 1.68-1.31 (m, 8H). MS: m/z 506.3 [M+H]$^+$.

Example 91

6-Nitro-1-(3-(4-(pyrimidin-2-yl)piperazine-1-carbonyl)benzyl)quinazoline-2,4(1H,3H)-dione $^1$H NMR (DMSO-d$_6$): 12.10 (s, 1H), 8.66 (d, J=2.7 Hz, 1H), 8.44 (d, J=9.3 Hz, 1H), 8.33 (d, J=4.5 Hz, 2H), 7.45-7.39 (m, 3H), 7.34-7.32 (m, 2H), 6.65 (t, J=4.6 Hz, 1H), 5.42 (s, 2H), 3.77-3.46 (m, 8H). MS: m/z 488.3 [M+H]$^+$.

Example 92

1-(3-(4-(Cyclohexylcarbonyl)piperazine-1-carbonyl)benzyl)-6-nitroquinazoline-2,4(1H,3H)-dione $^1$H NMR (DMSO-d$_6$): 12.21 (s, 1H), 8.77 (d, J=, 2.7 Hz, 1H), 8.51 (dd, J=9.2 and 2.6 Hz, 1H), 7.52-7.50 (m, 3H), 7.44-7.39 (m, 2H), 5.50 (s, 2H), 3.68-3.24 (m, 9H), 1.78-1.68 (m, 5H), 1.45-1.23 (m, 5H). MS: m/z 520.3 [M+H]$^+$.

The following compounds were prepared from 1-(4-carboxybenzyl)quinazoline-2,4(1H,3H)-dione (prepared from quinazoline-2,4(1H,3H)-dione and methyl 4-(bromomethyl)benzoate using a procedure similar to those used for Examples 1 and 2), and the corresponding substituted piperazine using a procedure similar to those described for the synthesis of compound of Example 3.

Example 93

1-(4-(4-(Benzoylpiperazine-1-carbonyl)benzyl)quinazoline-2,4(1H,3H)-dione

¹H NMR (CD₃OD): 8.17 (d, J=7.5 Hz, 1H), 7.68-7.63 (m, 1H), 7.53-7.41 (m, 9H), 7.30-7.27 (m, 2H), 5.46 (s, 2H), 3.76-3.40 (m, 8H). MS: m/z, 469.2 [M+H]⁺.

Example 94

1-(4-(4-(Pyridin-2-yl)piperazine-1-carbonyl)benzyl)quinazoline-2,4(1H,3H)-dione

¹H NMR (CD₃OD): 8.15 (d, J=8.1 Hz, 1H), 8.11 (d, J=5.1 Hz, 1H), 7.67-7.59 (m, 2H), 7.49-7.43 (m, 4H), 7.32-7.27 (m, 2H), 6.86 (d, J=8.4 Hz, 1H), 6.72 (t, J=6.0 Hz, 1H), 5.46 (s, 2H), 3.85-3.42 (m, 8H). MS: m/z 442.2 [M+H]⁺.

Example 95

1-(4-(4-(4-Methoxybenzoyl)piperazine-1-carbonyl)benzyl)quinazoline-2,4(1H,3H)-dione ¹H NMR (CD₃OD): 8.15 (d, J=7.5 Hz, 1H), 7.64 (t, J=7.5 Hz, 1H), 7.43-7.41 (m, 6H), 7.31-7.26 (m, 2H), 7.02-6.99 (m, 2H), 5.45 (s, 2H), 3.84 (s, 3H), 3.80-3.40 (m, 8H). MS: m/z 499.2 [M+H]⁺.

Example 96

1-(4-(4-(4-Fluorobenzoyl)piperazine-1-carbonyl)benzyl)quinazoline-2,4(1H,3H)-dione ¹H NMR (CD₃OD): 8.15 (d, J=6.9 Hz, 1H), 7.66-7.61 (m, 1H), 7.59-7.44 (m, 6H), 7.28-7.21 (m, 4H), 5.45 (s, 2H), 3.65-3.40 (m, 8H). MS: m/z 487.2 [M+H]⁺.

Example 97

1-(4-(4-(Pyridin-2-yl)piperazine-1-carbonyl)benzyl)quinazoline-2,4(1H,3H)-dione

¹H NMR (CD₃OD): 8.15 (d, J=4.8 Hz, 2H), 8.16 (dd, J=8.0 and 1.1 Hz, 1H), 7.65 (t, J=6.9 Hz, 1H), 7.49-7.41 (m, 4H), 7.32-7.28 (m, 2H), 6.64 (t, J=4.8 Hz, 1H), 5.46 (s, 2H), 3.80-3.40 (m, 8H). MS: m/z 443.3 [M+H]⁺.

Example 98

1-(4-(4-(4-Bromobenzoyl)piperazine-1-carbonyl)benzyl)quinazoline-2,4(1H,3H)-dione ¹H NMR (CD₃OD): 8.16 (d, J=7.8 Hz, 1H), 7.88-7.63 (m, 3H), 7.49-7.39 (m, 6H), 7.32-7.27 (m, 2H), 5.45 (s, 2H), 3.90-3.42 (m, 8H). MS: 547.2 [M+H]⁺.

Example 99

1-(4-(4-(Cyclopentylcarbonyl)piperazine-1-carbonyl)benzyl)quinazoline-2,4(1H,3H)-dione ¹H NMR (CD₃OD): 8.15 (dd, J=8.1 and 1.5 Hz, 1H), 7.64 (t, J=8.0 Hz, 1H), 7.49-7.42 (m, 4H), 7.31-7.26 (m, 2H), 5.45 (s, 2H), 3.83-3.39 (m, 8H), 3.09-3.00 (m, 1H), 2.02-1.51 (m, 8H). MS: 461.3 [M+H]⁺.

The following compounds were prepared from 5-chloro-1-(3-carboxybenzyl)quinazoline-2,4(1H,3H)-dione (prepared from 5-chloroquinazoline-2,4(1H,3H)-dione and methyl 3-(bromomethyl)benzoate using a procedure similar to those used for Examples 1 and 2), and the corresponding substituted piperazine using a procedure similar to those described for the synthesis of compound of Example 3.

Example 100

5-Chloro-1-(3-(4-(pyrimidin-2-yl)piperazine-1-carbonyl)benzyl)quinazoline-2,4(1H,3H)-dione ¹H NMR (CD₃OD): 8.38 (d, J=4.8 Hz, 2H), 7.60-7.50 (m, 3H), 7.45-7.39 (m, 2H), 7.35-7.20 (m, 2H), 7.26 (d, J=8.4 Hz, 1H), 6.66 (t, J=4.7 Hz, 1H), 5.48 (s, 2H), 4.00-3.40 (m, 8H). MS: m/z 477.2 [M+H]⁺.

Example 101

5-Chloro-1-(3-(4-(cyclopentylcarbonyl)piperazine-1-carbonyl)benzyl)quinazoline-2,4(1H,3H)-dione ¹H NMR (CD₃OD): 7.60-7.49 (m, 3H), 7.40-7.35 (m, 2H), 7.31 (d, J=9.0 Hz, 1H), 7.23 (d, J=9.0 Hz, 1H), 5.46 (s, 2H), 3.85-2.90 (m, 9H), 2.00-1.55 (m, 8H). MS: m/z 495.3 [M+H]⁺.

Example 102

5-Chloro-1-(3-(4-(cyclohexylcarbonyl)piperazine-1-carbonyl)benzyl)quinazoline-2,4(1H,3H)-dione ¹H NMR (DMSO-d₆): 11.68 (s, 1H), 7.53 (t, J=8.3 Hz, 1H), 7.45-7.39 (m, 2H), 7.30-7.20 (m, 3H), 7.15 (d, J=8.7 Hz, 1H), 5.34 (s, 2H), 3.70-3.00 (m, 9H), 1.80-1.00 (m, 10H). MS: m/z 509.3 [M+H]⁺.

The following compounds were prepared from 5-chloro-1-(3-carboxy-4-fluorobenzyl)quinazoline-2,4(1H,3H)-dione (prepared from 5-chloroquinazoline-2,4(1H,3H)-dione and methyl 5-(bromomethyl)-2-fluorobenzoate using a procedure similar to those used for Examples 1 and 2), and the corresponding substituted piperazine using a procedure similar to those described for the synthesis of compound of Example 3.

Example 103

5-Chloro-1-(4-fluoro-3-(4-(pyrimidin-2-yl)piperazine-1-carbonyl)benzyl)quinazoline-2,4(1H,3H)-dione ¹H NMR (DMSO-d₆): 11.69 (s, 1H), 8.39 (d, J=4.5 Hz, 2H), 7.50 (t, J=7.8 Hz, 1H), 7.47-7.39 (m, 2H), 7.32-7.25 (m, 2H), 7.20 (d, J=9.0 Hz, 1H), 6.67 (t, J=4.5 Hz, 1H), 5.32 (s, 2H), 3.81-3.33 (m, 8H). MS: m/z 495.2 [M+H]⁺.

Example 104

5-Chloro-1-(3-(4-(cyclopentylcarbonyl)piperazine-1-carbonyl)-4-fluorobenzyl)quinazoline-2,4(1H,3H)-dione ¹H NMR (DMSO-d₆): 11.69 (s, 1H), 7.58 (t, J=7.8 Hz, 1H), 7.47-7.42 (m, 1H), 7.38 (d, J=6.0 Hz, 1H), 7.31-7.25

(m, 2H), 7.18-7.14 (m, 1H), 5.31 (s, 2H), 3.70-3.00 (m, 9H), 1.85-1.40 (m, 8H). MS: m/z 513.3 [M+H]$^+$.

Example 105

5-Chloro-1-(3-(4-(cyclohexylcarbonyl)piperazine-1-carbonyl)-4-fluorobenzyl)quinazoline-2,4(1H,3H)-dione $^1$H NMR (DMSO-d$_6$): 11.67 (s, 1H), 7.53 (t, J=8.3 Hz, 1H), 7.45-7.41 (m, 1H), 7.35 (dd, J=6.2 and 2.0 Hz, 1H), 7.31-7.20 (m, 2H), 7.15 (s, 1H), 5.29 (s, 2H), 3.70-3.00 (m, 9H), 1.80-1.00 (m, 10H). MS: m/z 527.3 [M+H]$^+$.

Example 106

5-Chloro-1-(4-fluoro-3-(4-(pyridin-2-yl)piperazine-1-carbonyl)benzyl)quinazoline-2,4(1H,3H)-dione $^1$H NMR (DMSO-d$_6$): 11.66 (s, 1H), 8.11 (d, J=1.8 Hz, 1H), 7.57-7.52 (m, 2H), 7.45-7.37 (m, 2H), 7.31-7.20 (m, 2H), 7.17 (d, J=8.7 Hz, 1H), 6.81 (d, J=8.7 Hz, 1H), 6.56 (t, J=6.0 Hz, 1H), 5.30 (s, 2H), 3.80-3.10 (m, 8H). MS: m/z 494.2 [M+H]$^+$.

Example 107

5-Chloro-1-(4-fluoro-3-(4-(thiophene-2-carbonyl)piperazine-1-carbonyl)benzyl)quinazoline-2,4(1H,3H)-dione $^1$H NMR (DMSO-d$_6$): 11.68 (s, 1H), 7.76 (dd, J=5.0 and 1.1 Hz, 1H), 7.46 (t, J=8.4 Hz, 1H), 7.49-7.36 (m, 3H), 7.30-7.19 (m, 2H), 7.15-7.05 (m, 2H), 5.30 (s, 2H), 3.80-3.15 (m, 8H). MS: m/z 527.2 [M+H]$^+$.

The following compounds were prepared from 5-chloro-1-(6-fluoro-3-carboxybenzyl)quinazoline-2,4(1H,3H)-dione (prepared from 5-chloroquinazoline-2,4(1H,3H)-dione and methyl 3-(bromomethyl)-4-fluorobenzoate using a procedure similar to those used for Examples 1 and 2), and the corresponding substituted piperazine using a procedure similar to those described for the synthesis of compound of Example 3.

Example 108

5-Chloro-1-(3-(4-(cyclohexylcarbonyl)piperazine-1-carbonyl)-6-fluorobenzyl)quinazoline-2,4(1H,3H)-dione $^1$H NMR (DMSO-d$_6$): 11.70 (s, 1H), 7.55 (t, J=8.7 Hz, 1H), 7.45-7.34 (m, 2H), 7.27 (d, J=7.5 Hz, 1H), 7.17 (d, J=6.9 Hz, 1H), 7.13 (d, J=7.8 Hz, 1H), 5.33 (s, 2H), 3.80-3.00 (m, 9H), 1.80-1.10 (m, 10H). MS: m/z 527.3 [M+H]$^+$.

Example 109

5-Chloro-1-(3-(4-(cyclopentylcarbonyl)piperazine-1-carbonyl)-6-fluorobenzyl)quinazoline-2,4(1H,3H)-dione $^1$H NMR (DMSO-d$_6$): 11.71 (s, 1H), 7.57 (t, J=8.3 Hz, 1H), 7.45-7.25 (m, 3H), 7.20 (d, J=7.5 Hz, 1H), 7.14 (d, J=8.7 Hz, 1H), 5.35 (s, 2H), 3.70-2.80 (m, 9H), 1.85-1.40 (m, 8H). MS: m/z 513.3 [M+H]$^+$.

Example 110

5-Chloro-1-(6-fluoro-3-(4-(pyrimidin-2-yl)piperazine-1-carbonyl)benzyl)quinazoline-2,4(1H,3H)-dione $^1$H NMR (DMSO-d$_6$): 11.68 (s, 1H), 8.35 (d, J=4.5 Hz, 2H), 7.56 (t, J=8.4 Hz, 1H), 7.45-7.27 (m, 3H), 7.22 (d, J=6.6 Hz, 1H), 7.15 (d, J=8.7 Hz, 1H), 6.64 (t, J=4.5 Hz, 1H), 5.34 (s, 2H), 3.80-3.10 (m, 8H). MS: m/z 495.3 [M+H]$^+$.

The following compounds were prepared from 6-chloro-1-(3-carboxybenzyl)quinazoline-2,4(1H,3H)-dione (prepared from 6-chloroquinazoline-2,4(1H,3H)-dione and methyl 3-(bromomethyl)benzoate using a procedure similar to those used for Examples 1 and 2), and the corresponding substituted piperazine using a procedure similar to those described for the synthesis of compound of Example 3.

Example 111

6-Chloro-1-(3-(4-(pyrimidin-2-yl)piperazine-1-carbonyl)benzyl)quinazoline-2,4(1H,3H)-dione $^1$H NMR (CD$_3$OD) 8.37 (d, J=4.8 Hz, 2H), 8.09 (d, J=2.7 Hz, 1H), 7.64 (dd, J=9.2 and 2.6 Hz, 1H), 7.55-7.45 (m, 2H), 7.45-7.35 (m, 2H), 7.32 (d, J=9.0 Hz, 1H), 6.66 (t, J=4.7 Hz, 1H), 5.45 (s, 2H), 4.00-3.33 (m, 8H). MS: m/z 477.2 [M+H]$^+$.

Example 112

6-Chloro-1-(3-(4-(cyclopentylcarbonyl)piperazine-1-carbonyl)benzyl)quinazoline-2,4(1H,3H)-dione $^1$H NMR (DMSO-d$_6$): 11.87 (s, 1H), 7.94 (d, J=2.7 Hz, 1H), 7.70 (dd, J=9.0 and 2.7 Hz, 1H), 7.46-7.38 (m, 2H), 7.31-7.23 (m, 3H), 5.35 (s, 2H), 3.70-2.80 (m, 9H), 1.90-1.40 (m, 8H). MS: m/z 495.2 [M+H]$^+$.

Example 113

6-Chloro-1-(3-(4-(cyclohexylcarbonyl)piperazine-1-carbonyl)benzyl)quinazoline-2,4(1H,3H)-dione $^1$H NMR (DMSO-d$_6$): 11.88 (s, 1H), 7.94 (d, J=2.4 Hz, 1H), 7.74 (dd, J=9.0 and 2.4 Hz, 1H), 7.46-7.37 (m, 2H), 7.32-7.23 (m, 3H), 5.35 (s, 2H), 3.80-3.10 (m, 9H), 1.80-1.10 (m, 10H). MS: m/z 509.3 [M+H]$^+$.

Example 114

6-Chloro-1-(3-(4-(pyridin-2-yl)piperazine-1-carbonyl)benzyl)quinazoline-2,4(1H,3H)-dione $^1$H NMR (DMSO-d$_6$): 11.95 (s, 1H), 8.21-8.20 (m, 1H), 8.02 (s, 1H), 7.82-7.78 (m, 1H), 7.66-7.60 (m, 1H), 7.49-7.42 (m, 5H), 6.89 (d, J=3.0 Hz, 1H), 6.75 (t, J=6.0 Hz, 1H), 5.44 (s, 2H), 3.85-3.29 (m, 8H). MS: m/z 476.3 [M+H]$^+$.

Example 115

6-Chloro-1-(3-(4-(thiophene-2-carbonyl)piperazine-1-carbonyl)benzyl)quinazoline-2,4(1H,3H)-dione $^1$H NMR (DMSO-d$_6$): 11.87 (s, 1H), 7.92 (d, J=2.7 Hz, 1H), 7.76 (d, J=4.8 Hz, 1H), 7.67 (dd, J=8.9 and 2.6 Hz, 1H), 7.50-7.35 (m, 3H), 7.32-7.29 (m, 2H), 7.23 (d, J=9.0 Hz, 1H), 7.12 (dd, J=4.8 and 3.6 Hz, 1H), 5.33 (s, 2H), 3.79-3.45 (m, 8H). MS: m/z 509.2 [M+H]$^+$.

Example 116

6-Chloro-1-(3-(4-(cyclobutylcarbonyl)piperazine-1-carbonyl)benzyl)quinazoline-2,4(1H,3H)-dione $^1$H NMR (DMSO-d$_6$): 11.87 (s, 1H), 7.93 (d, J=2.4 Hz, 1H), 7.68 (dd, J=9.0 and 2.4 Hz, 1H), 7.43-7.35 (m, 2H), 7.31-7.22 (m, 3H), 5.33 (s, 2H), 3.60-3.00 (m, 9H), 2.20-1.60 (m, 6H). MS: m/z 481.3 [M+H]$^+$.

The following compounds were prepared from 6-chloro-1-(3-carboxy-4-fluorobenzyl)quinazoline-2,4(1H,3H)-dione (prepared from 6chloroquinazoline-2,4(1H,3H)-dione and methyl 5(bromomethyl)-2-fluorobenzoate using a procedure similar to those used for Examples 1 and 2), and the corresponding substituted piperazine using a procedure similar to those described for the synthesis of compound of Example 3.

Example 117

6-Chloro-1-(4-fluoro-3-(4-pyrimidin-2-yl)piperazine-1-carbonyl)benzyl)quinazoline-2,4(1H,3H)-dione $^1$H NMR (DMSO-d$_6$): 11.84 (s, 1H), 8.37 (d, J=4.8 Hz, 2H), 7.92 (s, 1H), 7.69 (dd, J=8.9 and 2.6 Hz, 1H), 7.47-7.36 (m, 2H), 7.30-7.24 (m, 2H), 6.65 (t, J=4.8 Hz, 1H), 5.30 (s, 2H), 3.78-3.21 (m, 8H). MS: m/z 495.2 [M+H]$^+$.

Example 118

6-Chloro-1-(3-(4-(cyclopentylcarbonyl)piperazine-1-carbonyl)benzyl)quinazoline-2,4(1H,3H)-dione $^1$H NMR (DMSO-d$_6$): 11.85 (s, 1H), 7.92. (d, J=2.4 Hz, 1H), 7.68 (dd, J=9.0 and 2.4 Hz, 1H), 7.44-7.41 (m, 1H), 7.36-7.34 (m, 1H), 7.30-7.15 (m, 2H), 5.29 (s, 2H), 3.70-2.80 (m, 9H), 1.80-1.40 (m, 8H). MS: m/z 513.3 [M+H]$^+$.

Example 119

6-Chloro-1-(3-(4-(cyclohexylcarbonyl)piperazine-1-carbonyl)-4-fluorobenzyl)quinazoline-2,4(1H,3H)-dione $^1$H NMR (DMSO-d$_6$): 11.85 (s, 1H), 7.92 (d, J=2.1 Hz, 1H), 7.68 (dd, J=8.7 and 2.4 Hz, 1H), 7.45-7.39 (m, 1H), 7.35 (d, J=5.4 Hz, 1H), 7.31-7.15 (m, 2H), 5.29 (s, 2H), 3.70-3.00 (m, 9H), 1.80-1.10 (m, 10H). MS: m/z 527.3 [M+H]$^+$.

Example 120

6-Chloro-1-(4-fluoro-3-(4-(pyridin-2-yl)piperazine-1-carbonyl)benzyl)quinazoline-2,4(1H,3H)-dione $^1$H NMR (DMSO-d$_6$): 8.10 (d, J=3.6 Hz, 1H), 7.92 (s, 1H), 7.69 (d, J=9.0 Hz, 1H), 7.54 (t, J=9.0 Hz, 1H), 7.45-7.36 (m, 2H), 7.30-7.23 (m, 2H), 6.81 (d, J=7.8 Hz, 1H), 6.66 (t, J=6.3 Hz, 1H), 5.30 (s, 2H), 3.68-3.21 (m, 8H). MS: m/z 494.2 [M+H]$^+$.

Example 121

6-Chloro-1-(4-fluoro-3-(4-(thiophene-2-carbonyl)piperazine-1-carbonyl)benzyl)quinazoline-2,4(1H,3H)-dione $^1$H NMR (DMSO-d$_6$): 11.86 (s, 1H), 7.92 (s, J=2.4 Hz, 1H), 7.76 (d, J=4.2 Hz, 1H), 7.68 (dd, J=9.0 and 2.4 Hz, 1H), 7.46-7.36 (m, 3H), 7.30-7.22 (m, 2H), 7.12 (dd, J=5.0 and 3.8 Hz, 1H), 5.30 (s, 2H), 3.68-3.21 (m, 8H). MS: m/z 527.2 [M+H]$^+$.

Example 122

6-Chloro-1-(3-(4-(cyclopropylcarbonyl)piperazine-1-carbonyl)-4-fluorobenzyl)quinazoline-2,4(1H,3H)-dione $^1$H NMR (DMSO-d$_6$): 11.85 (s, 1H), 7.94 (s, 1H), 7.70 (dd, J=8.4 and 2.1 Hz, 1H), 7.47-7.23 (m, 4H), 5.31 (s, 2H), 3.59-3.09 (m, 8H), 2.01-1.96 (m, 1H), 0.77-0.69 (m, 4H). MS: m/z 485.3 [M+H]$^+$.

The following compounds were prepared from 6-chloro-1-(6-fluoro-3-carboxybenzyl)quinazoline-2,4(1H,3H)-dione (prepared from 6-chloroquinazoline-2,4(1H,3H)-dione and methyl 3-(bromomethyl)-4-fluorobenzoate using a procedure similar to those used for Examples 1 and 2), and the corresponding substituted piperazine using a procedure similar to those described for the synthesis of compound of Example 3.

Example 123

6-Chloro-1-(6-fluoro-3-(4-(pyrimidin-2-yl)piperazine-1-carbonyl)benzyl)quinazoline-2,4(1H,3H)-dione $^1$H NMR (DMSO-d$_6$): 11.88 (s, 1H), 8.36 (d, J=4.5 Hz, 2H), 7.93 (d, J=2.4 Hz, 1H), 7.73 (dd, J=9.0 and 2.4 Hz, 1H), 7.36-7.20 (m, 4H), 6.55 (t, J=4.8 Hz, 1H), 5.37 (s, 2H), 3.78-3.21 (m, 8H). MS: m/z 495.2 [M+H]$^+$.

Example 124

6-Chloro-1-(3-(4-(cyclopentylcarbonyl)piperazine-1-carbonyl)-6-fluorobenzyl)quinazoline-2,4(1H,3H)-dione $^1$H NMR (DMSO-d$_6$): 11.87 (s, 1H), 7.94 (d, J=2.4 Hz, 1H), 7.71 (dd, J=9.2 and 2.3 Hz, 1H), 7.42-7.32 (m, 2H), 7.23-7.17 (m, 2H), 5.34 (s, 2H), 3.59-3.09 (m, 9H), 1.71-1.56 (m, 8H). MS: m/z 513.3 [M+H]$^+$.

Example 125

6-Chloro-1-(3-(4-(cyclohexylcarbonyl)piperazine-1-carbonyl)-6-fluorobenzyl)quinazoline-2,4(1H,3H)-dione $^1$H NMR (DMSO-d$_6$): 11.87 (s, 1H), 7.93 (d, J=2.4 Hz, 1H), 7.70 (dd, J=8.9 and 2.6 Hz, 1H), 7.41-7.31 (m, 2H), 7.22-7.16 (m, 2H), 5.33 (s, 2H), 3.54-3.10 (m, 9H), 1.70-1.15 (m, 10H). MS: m/z 577.3 [M+H]⁺.

Example 126

6-Chloro-1-(6-fluoro-3-(4-(thiophene-2-carbonyl) piperazine-1-carbonyl)benzyl)quinazoline-2,4(1H,3H)-dione ¹H NMR (DMSO-d₆): 11.86 (s, 1H), 7.93 (d, J=2.4 Hz, 1H), 7.76 (d, J=4.8 Hz, 1H), 7.67 (dd, J=9.0 and 1.8 Hz, 1H), 7.43-7.32. (m, 3H), 7.22-7.19 (m, 2H), 7.12 (t, J=4.2 Hz, 1H), 5.33 (s, 2H), 3.54-3.19 (m, 8H). MS: m/z 527.2 [M+H]⁺.

The following compounds were prepared from 5-fluoro-1-(3-carboxybenzyl)quinazoline-2,4(1H,3H)-dione (prepared from 5-fluoroquinazoline-2,4(1H,3H)-dione and methyl 3-(bromomethyl)benzoate using a procedure similar to those used for Examples 1 and 2), and the corresponding substituted piperazine using a procedure similar to those described for the synthesis of compound of Example 3.

Example 127

5-Fluoro-1-(3-(4-(pyrimidin-2-yl)piperazine-1-carbonyl)benzyl)quinazoline-2,4(1H,3H)-dione ¹H NMR (CD₃OD): 8.35 (d, J=4.8 HZ, 2H), 7.61 (td, J=8.4 and 5.7 Hz, 1H), 7.50-7.32 (m, 4H), 7.06 (d, J=8.4 Hz, 1H), 6.99 (dd, J=10.8 and 8.4 Hz, 1H), 6.64 (t, J=4.8 Hz, 1H), 5.48 (s, 2H), 3.89-3.38 (s, 8H). MS: m/z 461.2 [M+H]⁺.

Example 128

1-(3-(4-(Cyclopentylcarbonyl(piperazine-1-carbonyl)benzyl)-5-fluoroquinazoline-2,4(1H,3H)-dione ¹H NMR (DMSO-d₆): 11.67 (s, 1H), 7.65-7.57 (m, 1H), 7.41-7.39 (m, 2H), 7.31-7.27 (m, 2H), 7.05-6.97 (m, 2H), 5.32 (s, 2H), 3.69-2.90 (m, 9H), 1.81-1.51 (m, 8H). MS: m/z 479.3 [M+H]⁺.

Example 129

1-(3-(4-(Cyclohexylcarbonyl(piperazine-1-carbonyl) benzyl)-5-fluoroquinazoline-2,4(1H,3H)-dione ¹H NMR (DMSO-d₆): 11.69 (s, 1H), 7.62 (td, J=8.4 and 6.0 Hz, 1H), 7.46-7.41 (m, 2H), 7.32-7.29 (m, 2H), 7.05-6.99 (m, 2H), 5.34 (s, 2H), 3.79-3.11 (m, 9H), 1.71-1.61 (m, 5H), 1.33-1.17 (m, 5H). MS: m/z 493.3 [M+H]⁺.

Example 130

5-Fluoro-1-(3-(4-(pyridin-2-yl)piperazine-1-carbonyl)benzyl)quinazoline-2,4(1H,3H)-dione ¹H NMR (DMSO-d₆): 11.67 (s, 1H), 8.10 (d, J=3.6 Hz, 1H), 7.66-7.51 (m, 2H), 7.44-7.29 (m, 4H), 7.04-6.98 (m, 2H), 6.80 (d, J=8.7 Hz, 1H), 6.64 (t, J=6.6 Hz, 1H), 5.33 (s, 2H), 3.79-3.41 (m, 8H). MS: m/z 460.3 [M+H]⁺.

Example 131

5-Fluoro-1-(3-(4-(thiophene-2-carbonyl)piperazine-1-carbonyl)benzyl)quinazoline-2,4(1H,3H)-dione ¹H NMR (DMSO-d₆): 11.67 (s, 1H), 7.77 (d, J=5.1 Hz, 1H), 7.59 (td, J=6.0 and 8.4 Hz, 1H), 7.44-7.29 (m, 5H), 7.14 (d, J=3.9 Hz, 1H), 7.02-6.95 (m, 2H), 5.33 (s, 2H), 3.64-3.41 (m, 8H). MS: m/z 493.2 [M+H]⁺.

The following compounds were prepared from 1-(3-carboxy-4-fluorobenzyl)-5-fluoroquinazoline-2,4(1H,3H)-dione (prepared from 5-fluoroquinazoline-2,4(1H,3H)-dione and methyl 5-(bromomethyl)-2-fluorobenzoate using a procedure similar to those used for Examples 1 and 2), and the corresponding substituted piperazine using a procedure similar to those described for the synthesis of compound of Example 3.

Example 132

5-Fluoro-1-(4-fluoro-3-(4-(pyrimidin-2-yl)piperazine-1-carbonyl)benzyl)quinazoline-2,4(1H,3H)-dione ¹H NMR (DMSO-d₆): 11.65 (s, 1H), 8.38 (d, J=4.8 Hz, 2H), 7.95-7.66 (m, 1H), 7.47-7.38 (m, 2H), 7.28 (t, J=9.0 Hz, 1H), 7.05-6.99 (m, 2H), 6.66 (t, J=4.8 Hz, 1H), 5.30 (s, 2H), 3.82-3.79 (m, 2H), 3.69-3.61 (m, 4H), 3.23-3.21 (m, 2H). MS: m/z 479.2 [M+H]⁺.

Example 133

1-(3-(4-(Cyclopentylcarbonyl(piperazine-1-carbonyl)-4-fluorobenzyl)-5-fluoroquinazoline-2,4(1H,3H)-dione ¹H NMR (DMSO-d₆): 11.66 (s, 1H), 7.65-7.58 (m, 1H), 7.47-7.41 (m, 1H), 7.38 (d, J=5.7 Hz, 1H), 7.27 (t, J=9.0 Hz, 1H), 7.05-6.98 (m, 2H), 5.29 (s, 2H), 3.59-2.89 (m, 9H), 1.79-1.45 (m, 8H). MS: m/z 497.3 [M+H]⁺.

Example 134

1-(3-(4-(Cyclohexylcarbonyl(piperazine-1-carbonyl)-4-fluorobenzyl)-5-fluoroquinazoline-2,4(1H,3H)-dione ¹H NMR (DMSO-d₆): 11.67 (s, 1H), 7.66-7.59 (m, 1H), 7.47-7.43 (m, 1H), 7.38 (d, J=6.0 Hz, 1H), 7.28 (t, J=8.9 Hz, 1H), 7.05-6.99 (m, 2H), 5.30 (s, 2H), 3.55-3.12 (m, 9H), 1.62-1.06 (m, 10H). MS: m/z 511.3 [M+H]⁺.

Example 135

5-Fluoro-1-(4-fluoro-3-(4-(pyridin-2-yl)piperazine-1-carbonyl)benzyl)quinazoline-2,4(1H,3H)-dione ¹H NMR (DMSO-d₆): 11.65 (s, 1H), 8.11 (dd, J=5.0 and 1.7 Hz, 1H), 7.70-7.50 (m, 2H), 7.48-7.37 (m, 2H), 7.27 (t, J=9.0 Hz, 1H), 7.04-6.98 (m, 2H), 6.81 (d, J=8.7 Hz, 6.66 (t, J=5.7 Hz, 1H), 5.29 (s, 2H), 3.70-3.68 (m, 2H), 3.57-3.54 (m, 2H), 3.38-3.34 (m, 2H), 3.24-3.22 (m, 2H). MS: m/z 478.2 [M+H]⁺.

Example 136

5-Fluoro-1-(4-fluoro-3-(4-(thiophene-2-carbonyl) piperazine-1-carbonyl)benzyl)quinazoline-2,4(1H,3H)-dione ¹H NMR (DMSO-d₆): 11.64 (s, 1H), 7.77 (d, J=4.8 Hz, 1H), 7.64-7.56 (m, 1H), 7.46-7.37 (m, 3H), 7.27 (t, J=9.0

Hz, 1H), 7.13 (t, J=4.8 Hz, 1H), 7.02-6.97 (m, 2H), 5.30 (s, 2H), 3.70-3.23 (m, 8H). MS: m/z 511.2 [M+H]$^+$.

Example 137

1-(3-(4-Benzoylpiperazine-1-carbonyl)-4-fluorobenzyl)-5-fluoroquinazoline-2,4(1H,3H)-dione $^1$H NMR (DMSO-d$_6$): 11.67 (s, 1H), 7.60-7.27 (m, 9H), 7.05-6.95 (m, 2H), 5.30 (s, 2H), 3.66-3.29 (m, 8H). MS: m/z 505.3 [M+H]$^+$.

Compound of Example 138 was prepared from 1-(3-carboxybenzyl)-8-fluoroquinazoline-2,4(1H,3H)-dione (prepared from 8-fluoroquinazoline-2,4(1H,3H)-dione and methyl 3-(bromomethyl)benzoate using a procedure similar to those used for Examples 1 and 2), and the corresponding substituted piperazine using a procedure similar to those described for the synthesis of compound of Example 3.

Example 138

1-(3-(4-(Cyclohexylcarbonyl)piperazine-1-carbonyl)benzyl)-8-fluoroquinazoline-2,4(1H,3H)-dione $^1$H NMR (DMSO-d$_6$): 11.90 (s, 1H), 7.91 (d, J=7.2 Hz, 1H), 7.59-7.51 (m, 1H), 7.44-7.33 (m, 2H), 7.29-7.28 (m, 3H), 5.40 (s, 2H), 3.59-3.19 (m, 9H), 1.61-1.24 (m, 10H). MS: m/z 493.3 [M+H]$^+$.

The following compounds were prepared from 6-fluoro-1-(3-carboxybenzyl) quinazoline-2,4(1H,3H)-dione (prepared from 6-fluoroquinazoline-2,4(1H,3H)-dione and methyl 3-(bromomethyl)benzoate using procedures similar to those of compounds of Examples 1 and 2), and the corresponding substituted piperazine using a procedure similar to those described for the synthesis of compound of Example 3.

Example 139

6-Fluoro-1-(3-(4-(pyrimidin-2-yl)piperazine-1-carbonyl)benzyl)quinazoline-2,4(1H,3H)-dione $^1$H NMR (DMSO-d$_6$): 11.86 (s, 1H), 8.38 (d, J=4.5 Hz, 2H), 7.73 (dd, J=8.1 and 3.0 Hz, 1H), 7.57 (td, J=9.0 and 3.3 Hz, 1H), 7.36-7.27 (m, 5H), 6.67 (t, J=4.7 Hz, 1H), 5.36 (s, 2H), 3.65-3.30 (m, 8H). MS: m/z 461.2 [M+H]$^+$.

Example 140

6-Fluoro-1-(3-(4-(pyridin-2-yl)piperazine-1-carbonyl)benzyl)quinazoline-2,4(1H,3H)-dione $^1$H NMR (DMSO-d$_6$): 11.85 (s, 1H), 8.13 (d, J=3.3 Hz, 1H), 7.73 (dd, J=8.4 and 3.0 Hz, 1H), 7.61-7.53 (m, 2H), 7.46-7.38 (m, 2H), 7.35-7.28 (m, 3H), 6.82 (d, J=8.4 Hz, 1H), 6.67 (t, J=4.8 Hz, 1H), 5.36 (s, 2H), 3.76-3.33 (m, 8H). MS: m/z 460.3 [M+H]$^+$.

Example 141

6-Fluoro-1-(3-(4-(thiophene-2-carbonyl)piperazine-1-carbonyl)benzyl)quinazoline-2,4(1H,3H)-dione $^1$H NMR (DMSO-d$_6$): 11.85 (s, 1H), 7.77-7.76 (m, 2H), 7.73 (dd, J=8.4 and 3.0 Hz, 1H), 7.54-7.14 (m, 6H), 7.13 (t, J=4.4 Hz, 1H), 5.35 (s, 2H), 3.66-3.30 (m, 8H), m/z 493.2 [M+H]$^+$.

Example 142

1-(3-(4-(Cyclohexylcarbonyl)piperazine-1-carbonyl)benzyl)-6-fluoroquinazoline-2,4(1H,3H)-dione $^1$H NMR (DMSO-d$_6$): 11.86 (s, 1H), 7.74 (dd, J=8.1 and 3.0 Hz, 1H), 7.56 (m, 1H), 7.43-7.41 (m, 2H), 7.32-7.29 (m, 3H), 5.36 (s, 2H), 3.60-3.10 (m, 9H), 1.61-1.29 (m, 10H). MS: m/z 493.3 [M+H]$^+$.

Example 143

1-(3-(4-(Cyclopentylcarbonyl)piperazine-1-carbonyl)benzyl)-6-fluoroquinazoline-2,4(1H,3H)-dione $^1$H NMR (CD$_3$OD): 7.84 (dd, J=8.4 and 3.0 Hz, 1H), 7.52-7.43 (m, 5H), 7.34 (dd, J=9.2 and 4.1 Hz, 1H), 5.46 (s, 2H), 3.72-3.11 (m, 9H), 1.88-1.66 (m, 8H). MS: m/z 479.3 [M+H]$^+$.

The following compounds were prepared from 6-fluoro-1-(3-carboxy-4-fluorobenzyl)quinazoline-2,4(1H,3H)-dione (prepared from 6-fluoroquinazoline-2,4(1H,3,1)-dione and methyl 5-(bromomethyl)-2-fluorobenzoate using procedures similar to those of compounds of Examples 1 and 2), and the corresponding substituted piperazine using a procedure similar to those described for the synthesis of compound of Example 3.

Example 144

6-Fluoro-1-(4-fluoro-3-(4-(pyrimidin-2-yl)piperazine-1-carbonyl)benzyl)quinazoline-2,4(1H,3H)-dione $^1$H NMR (DMSO-d$_6$): 11.83 (s, 1H), 8.39 (d, J=4.8 Hz, 2H), 7.74 (dd, J=8.4 and 3.0 Hz, 1H), 7.60-7.54 (m, 1H), 7.41-7.29 (m, 4H), 6.67 (t, J=4.8 Hz, 1H), 5.32 (s, 2H), 3.81-3.23 (m, 8H). MS: m/z 479.3 [M+H]$^+$.

Example 145

6-Fluoro-1-(4-fluoro-3-(4-(pyridin-2-yl)piperazine-1-carbonyl)benzyl)quinazoline-2,4(1H,3H)-dione $^1$H NMR (DMSO-d$_6$): 11.85 (s, 1H), 8.12 (dd, J=4.8 and 1.5 Hz, 1H), 7.72 (dd, J=8.3 and 3.2 Hz, 1H), 7.60-7.53 (m, 2H), 7.47-7.40 (m, 2H), 7.32-7.26 (m, 2H), 6.83 (d, J=8.7 Hz, 1H), 6.68 (dd, J=6.9 and 5.1 Hz, 1H), 5.33 (s, 2H), 3.72-3.25 (m, 8H). MS: m/z 478.3 [M+H]$^+$.

Example 146

6-Fluoro-1-(4-fluoro-3-(4-(thiophene-2-carbonyl)piperazine-1-carbonyl)benzyl)quinazoline-2,4(1H,3H)-dione $^1$H NMR (DMSO-d$_6$): 11.83 (s, 1H), 7.77-7.70 (m, 2H), 7.57-7.51 (m, 1H), 7.41-7.37 (m, 3H), 7.31-7.25 (m, 2H), 7.12 (t, J=4.2 Hz, 1H), 5.31 (s, 2H), 3.70-3.16 (m, 8H). MS: m/z 511.2 [M+H]$^+$.

Example 147

1-(3-(4-(Cyclohexylcarbonyl)piperazine-1-carbonyl)-4-fluorobenzyl)-6-fluoroquinazoline-2,4(1H,3H)-dione $^1$H NMR (DMSO-d$_6$): 11.83 (s, 1H), 7.72 (dd, J=8.3 and 3.2 Hz, 1H), 7.57-7.50 (m, 1H), 7.45-7.41 (m, 1H), 7.36 (d, J=6.3 Hz, 1H), 7.29-7.23 (m, 2H), 5.30 (s, 2H), 3.53-3.10 (m, 9H), 1.60-1.21(m, 10H). MS: m/z 511.3 [M+H]$^+$.

Example 148

1-(3-(4-(Cyclopentylcarbonyl)piperazine-1-carbonyl)-4-fluorobenzyl)-6-fluoroquinazoline-2,4(1H,3H)-dione $^1$H NMR (DMSO-d$_6$): 11.83 (s, 1H), 7.73 (dd, J=8.4 and 3.0 Hz, 1H), 7.55 (t, J=8.4 Hz, 1H), 7.46-7.42 (m, 1H), 7.36 (d, J=6.0 Hz, 1H), 7.30-7.24 (m, 2H), 5.31 (s, 2H), 3.56-3.12 (m, 9H), 1.60-1.56 (m, 8H). MS: m/z 479.3 [M+H]$^+$.

The following compounds were prepared from 6-fluoro-1-(3-carboxy-6-fluorobenzyl)quinazoline-2,4(1H,3H)-dione (prepared from 6-fluoroquinazoline-2,4(1H,3H)-dione and methyl 3-(bromomethyl)-4-fluorobenzoate using procedures similar to those of compounds of Examples 1 and 2), and the corresponding substituted piperazine or piperidine using a procedure similar to those described for the synthesis of compound of Example 3.

Example 149

6-Fluoro-1-(6-fluoro-3-(4-(pyrimidin-2-yl)piperazine-1-carbonyl)benzyl)quinazoline-2,4(1H,3H)-dione $^1$H NMR (DMSO-d$_6$): 11.85 (s, 1H), 8.38 (d, J=4.5 Hz, 2H), 7.74 (dd, J=8.3 and 3.2 Hz, 1H), 7.62-7.55 (m, 1H), 7.39-7.33 (m, 2H), 7.30-7.20 (m, 2H), 6.66 (t, J=4.8 Hz, 1H), 5.37 (s, 2H), 3.65-3.30 (m, 8H). MS: 479.3 [M+H]$^+$.

Example 150

6-Fluoro-1-(6-fluoro-3-(4-(pyridin-2-yl)piperazine-1-carbonyl)benzyl)quinazoline-2,4(1H,3H)-dione $^1$H NMR (DMSO-d$_6$): 11.85 (s, 1H), 8.12 (d, J=3.3 Hz, 1H), 7.74 (d, J=8.4 Hz, 1H), 7.63-7.52 (m, 2H), 7.40-7.26 (m, 3H), 7.21 (d, J=7.2 Hz, 1H), 6.77 (d, J=8.4 Hz, 1H), 6.66 (t, J=5.9 Hz, 1H), 5.37 (s, 2H), 3.51-3.32 (m, 8H). MS: m/z 478.3 [M+H]$^+$.

Example 151

6-Fluoro-1-(6-fluoro-3-(4-(thiophene-2-carbonyl)piperazine-1-carbonyl)benzyl)quinazoline-2,4(1H,3H)-dione $^1$H NMR (DMSO-d$_6$): 11.83 (s, 1H), 7.75-7.69 (m, 2H), 7.52-7.49 (m, 1H), 7.39-7.30 (m, 3H), 7.23-7.17 (m, 2H), 7.11 (t, J=4.2 Hz, 1H), 5.33 (s, 2H), 3.70-3.13 (m, 8H). MS: m/z 511.2 [M+H]$^+$.

Example 152

1-(3-(4-(Cyclohexylcarbonyl)piperazine-1-carbonyl)-6-fluorobenzyl)-6-fluoroquinazoline-2,4(1H,3H)-dione $^1$H NMR (DMSO-d$_6$): 11.86 (s, 1H), 7.76 (dd, J=8.1 and 3.0 Hz, 1H), 7.60-7.54 (m, 1H), 7.39-7.35 (m, 2H), 7.24 (dd, J=9.2 and 4.1 Hz, 1H), 7.18 (d, J=6.9 Hz, 1H), 5.36 (s, 2H), 3.53-3.10 (m, 9H), 1.70-1.25 (m, 10H). MS: m/z 511.3 [M+H]$^+$.

Example 153

1-(3-(4-(Cyclopentylcarbonyl)piperazine-1-carbonyl)-6-fluorobenzyl)-6-fluoroquinazoline-2,4(1H,3H)-dione $^1$H NMR (DMSO-d$_6$): 7.72 (dd, J=8.6 and 3.9 Hz, 1H), 7.58-7.51 (m, 1H), 7.36-7.33 (m, 2H), 7.23 (dd, J=9.5 and 3.8 Hz, 1H), 7.16 (d, J=7.2 Hz, 1H), 5.33 (s, 2H), 3.31-2.63 (m, 9H), 1.73-1.43 (m, 8H). MS: m/z 479.3 [M+H]$^+$.

The following compounds were prepared from 5-fluoro-1-(3-carboxy-6-fluorobenzyl)quinazoline-2,4(1H,3H)-dione and the corresponding substituted piperazine using procedure similar to those described for the synthesis of compound of Example 3.

Example 154

5-Fluoro-1-(6-fluoro-3-(4-(pyrimidin-2-yl)piperazine-1-carbonyl)benzyl)quinazoline-2,4(1H,3H)-dione $^1$H NMR (DMSO-d$_6$): 11.68 (s, 1H), 8.38 (d, J=4.5 Hz, 2H), 7.67-7.65 (m, 1H), 7.40-7.33 (m, 2H), 7.21 (d, J=7.2 Hz, 1H), 7.08-7.00 (m, 2H), 6.66 (t, J=4.8 Hz, 1H), 5.35 (s, 2H), 3.81-3.23 (m, 8H). MS: m/z 479.3 [M+H]$^+$.

Example 155

5-Fluoro-1-(6-fluoro-3-(4-(pyridin-2-yl)piperazine-1-carbonyl)benzyl)quinazoline-2,4(1H,3H)-dione $^1$H NMR (DMSO-d$_6$): 11.66 (s, 1H), 8.10 (d, J=3.3 Hz, 1H), 7.69-7.61 (m, 1H), 7.53 (t, J=6.9 Hz, 1H), 7.40-7.31 (m, 2H), 7.21 (d, J=6.6 Hz, 1H), 7.08-6.99 (m, 2H), 6.76 (d, J=8.7 Hz, 1H), 6.65 (t, J=6.9 Hz, 1H), 5.34 (s, 2H), 3.51-3.30 (m, 8H). MS: m/z 478.3 [M+H]$^+$.

Example 156

5-Fluoro-1-(6-fluoro-3-(4-(thiophene-2-carbonyl)piperazine-1-carbonyl)benzyl)quinazoline-2,4(1H,3H)-dione $^1$H NMR (DMSO-d$_6$): 11.69 (s, 1H), 7.78 (d, J=4.5 Hz, 1H), 7.64-7.60 (m, 1H), 7.38-7.35 (m, 3H), 7.22 (d, J=6.0 Hz, 1H), 7.16-7.13 (m, 1H), 7.00-6.94 (m, 2H), 5.33 (s, 2H), 3.32-3.15 (m, 8H). MS: m/z 511.2 [M+H]$^+$.

Example 157

1-(3-(4-(Cyclohexylcarbonyl)piperazine-1-carbonyl)-6-fluorobenzyl)-5-fluoroquinazoline-2,4(1H,3H)-dione $^1$H NMR (DMSO-d$_6$): 11.70 (s, 1H), 7.68-7.61 (m, 1H), 7.39-7.33 (m, 2H), 7.21 (d, J=7.2 Hz, 1H), 7.06-6.97 (m, 2H), 5.34 (s, 2H), 3.53-3.10 (m, 9H), 1.70-1.24 (m, 10H). MS: m/z 511.3 [M+H]$^+$.

Example 158

1-(3-(4-(Cyclopentylcarbonyl)piperazine-1-carbonyl)-6-fluorobenzyl)-5-fluoroquinazoline-2,4(1H,3H)-dione $^1$H NMR (DMSO-d$_6$): 11.68 (s, 1H), 7.67-7.60 (m, 1H), 7.41-7.32 (m, 2H), 7.20 (d, J=7.5 Hz, 1H), 7.06-6.97 (m, 2H), 5.33 (s, 2H), 3.60-3.15 (m, 9H), 1.60-1.55 (m, 8H). MS: m/z 497.3 [M+H]$^+$.

The following compounds were prepared from 5-methyl-1-(3-carboxybenzyl)quinazoline-2,4(1H,3H)-dione and the corresponding substituted piperazine using a procedure similar to those described for the synthesis of compound of Example 3.

Example 159

5-Methyl-1-(3-(4-(pyrimidin-2-yl)piperazine-1-carbonyl)benzyl)quinazoline-2,4(1H,3H)-dione $^1$H NMR (CD$_3$OD): 8.37 (d, J=4.8 Hz, 2H), 7.49-7.47 (m, 3H), 7.42-7.36 (m, 2H), 7.14-7.08 (m, 2H), 6.66 (t, J=5.0 Hz, 1H), 5.46 (s, 2H), 3.91-3.62 (m, 8H), 2.79 (s, 3H). MS: m/z 457.3 [M+H]$^+$.

Example 160

1-(3-(4-(Cyclopentylcarbonyl)piperazine-1-carbonyl)benzyl)-5-methylquinazoline-2,4(1H,3H)-dione $^1$H NMR (CD$_3$OD): 7.49-7.36 (m, 5H), 7.14-7.08 (m, 2H), 5.46 (s, 2H), 3.82-3.10 (m, 9H), 2.80 (s, 3H), 1.88-1.56 (m, 8H). MS: m/z 475.3 [M+H]$^+$.

The following compounds were prepared from 1-(3-carboxybenzyl)-7-chloroquinazoline-2,4(1H,3H)-dione and the corresponding substituted piperazine using a procedure similar to those described for the synthesis of compound of Example 3.

Example 161

7-Chloro-1-(3-(4-(pyrimidin-2-yl)piperazine-1-carbonyl)benzyl)quinazoline-2,4(1H,3H)-dione $^1$H NMR (DMSO-d$_6$): 11.81 (s, 1H), 8.37 (d, J=4.8 Hz, 2H), 8.00 (d, J=8.4 Hz, 1H), 7.40-7.27 (m, 6H), 6.65 (t, J=4.7 Hz, 1H), 5.36 (s, 2H), 3.77-3.63 (m, 8H). MS: m/z 477.2 [M+H]$^+$.

Example 162

7-Chloro-1-(3-(4-(cyclopentylcarbonyl)piperazine-1-carbonyl)benzyl)quinazoline-2,4(1H,3H)-dione $^1$H NMR (DMSO-d$_6$): 11.85 (s, 1H), 8.02 (d, J=9.0 Hz, 1H), 7.44-7.29 (m, 6H), 5:36 (s, 2H), 3.40-3.10 (m, 9H), 1.81-1.51 (m, 8H). MS: m/z 495.3 [M+H]$^+$.

The following compounds were prepared from the corresponding substituted 1-(3-carboxybenzyl)quinazoline-2,4(1H,3H)-dione and substituted piperazine using a procedure similar to those described for the synthesis of compound of Example 3.

Example 163

1-(3-(4-(Cyclopropylcarbonyl)piperazine-1-carbonyl)-4-fluorobenzyl)-5-fluoroquinazoline-2,4(1H,3H)-dione $^1$H NMR (DMSO-d$_6$): 11.65 (s, 1H), 7.65-7.57 (m, 1H), 7.46-7.41 (m, 1H), 7.38-7.35 (m, 1H), 7.30-7.23 (m, 1H), 7.04-6.98 (m, 2H), 5.29 (s, 2H), 3.75-3.15 (m, 8H), 1.99-1.96 (m, 1H), 0.72-0.69 (m, 4H). MS: m/z 469.5 [M+H]$^+$.

Example 164

6-Chloro-1-(3-(4-benzoylpiperazine-1-carbonyl)-4-fluorobenzyl)quinazoline-2,4(1H,3H)-dione $^1$H NMR (DMSO-d$_6$): 11.85 (s, 1H), 7.91 (s, 1H), 7.68-7.62 (m, 1H), 7.44-7.35 (m, 7H), 7.28-7.22 (m, 2H), 5.29 (s, 2H), 3.64-3.21 (m, 8H). MS: m/z 521.5 [M+H]$^+$.

Example 165

1-(3-(4-(Cyclobutylcarbonyl)piperazine-1-carbonyl)benzyl)-5-fluoroquinazoline-2,4(1H,3H)-dione $^1$H NMR (DMSO-d$_6$): 11.66 (s, 1H), 7.64-7.57 (m, 1H), 7.43-7.36 (m, 2H), 7.29-7.26 (m, 2H), 7.04-6.98 (m, 2H), 5.32 (s, 2H), 3.56-3.00 (m, 9H), 2.17-1.66 (m, 6H). MS: m/z 465.6 [M+H]$^+$.

Example 166

1-(3-(4-(Cyclobutylcarbonyl)piperazine-1-carbonyl)-4-fluorobenzyl)-5-fluoroquinazoline-2,4(1H,3H)-dione $^1$H NMR (DMSO-d$_6$): 11.65 (s, 1H), 7.65-7.57 (m, 1H), 7.46-7.40 (m, 1H), 7.36 (d, J=5.4 Hz, 1H), 7.26 (t, J=9.0 Hz, 1H), 7.04-6.99 (m, 2H), 5.28 (s, 2H), 3.55-3.09 (m, 9H), 2.18-1.67 (m, 6H). MS: m/z 483.3 [M+H]$^+$.

Example 167

6-Chloro-1-(3-(4-(cyclobutylcarbonyl)piperazine-1-carbonyl)-6-fluorobenzyl)quinazoline-2,4(1H,3H)-dione $^1$H NMR (DMSO-d$_6$): 11.87 (s, 1H), 7.95 (d, J=2.4 Hz, 1H), 7.69 (dd, J=8.9 and 2.6 Hz, 1H), 7.42-7.30 (m, 2H), 7.22-7.15 (m, 2H), 5.33 (s, 2H), 3.55-3.09 (m, 9H), 2.14-1.72 (m, 6H). MS: m/z 499.3 [M+H]$^+$.

Example 168

5-Chloro-1-(3-(4-(cyclobutylcarbonyl)piperazine-1-carbonyl)-4-fluorobenzyl)quinazoline-2,4(1H,3H)-dione $^1$H NMR (DMSO-d$_6$): 11.69 (s, 1H), 7.55 (t, J=8.3 Hz, 1H), 7.46-7.42 (m, 1H), 7.37 (d, J=6.3 Hz, 1H), 7.30-7.24 (m, 2H), 7.18-7.13 (m, 1H), 5.31 (s, 2H), 3.56-3.11 (m, 9H), 2.10-1.73 (m, 6H). MS: m/z 499.3 [M+H]$^+$.

Example 169

6-Chloro-1-(3-(4-(cyclobutylcarbonyl)piperazine-1-carbonyl)-4-fluorobenzyl)quinazoline-2,4(1H,3H)-dione $^1$H NMR (DMSO-d$_6$): 11.88 (s, 1H), 7.94 (s, 1H), 7.70 (dd, J=9.0 and 2.7 Hz, 1H), 7.46-7.42 (m, 1H), 7.36 (dd, J=6.3 and 1.8 Hz, 1H), 7.31-7.21 (m, 2H), 5.30 (s, 2H), 3.56-3.11 (m, 9H), 2.50-1.73 (m, 6H). MS: m/z 499.3 [M+H]$^+$.

Example 170

5-Chloro-1-(3-(4-(cyclobutylcarbonyl)piperazine-1-carbonyl)-6-fluorobenzyl)quinazoline-2,4(1H,3H)-dione $^1$H NMR (DMSO-$d_6$): 11.69 (s, 1H), 7.57 (t, J=8.3 Hz, 1H), 7.38-7.29 (m, 3H), 7.20 (d, J=6.9 Hz, 1H), 7.15 (d, J=8.7 Hz, 1H), 5.35 (s, 2H), 3.56-3.00 (m, 9H), 2.12-1.74 (m, 6H). MS: m/z 499.4 [M+H]$^+$.

Example 171

5-Chloro-1-(6-fluoro-3-(4-(thiophene-2-carbonyl)piperazine-1-carbonyl)benzyl)quinazoline-2,4(1H,3H)-dione $^1$H NMR (DMSO-$d_6$): 11.72 (s, 1H), 7.79 (d, J=5.1 Hz, 1H), 7.54 (t, J=8.3 Hz, 1H), 7.39-7.36 (m, 3H), 7.23 (m, 2H), 7.14-7.11 (m, 2H), 5.35 (s, 2H), 3.66-3.10 (m, 8H). MS: m/z 527.2 [M+H]$^+$.

Example 172

5-Fluoro-1-(4-fluoro-3-(4-(furan-2-carbonyl)piperazine-1-carbonyl)benzyl)quinazoline-2,4(1H,3H)-dione $^1$H NMR (DMSO-$d_6$): 11.67 (s, 1H), 7.85 (s, 1H), 7.66-7.58 (m, 1H), 7.46-7.39 (m, 2H), 7.29 (t, J=9.0 Hz, 1H), 7.04-6.98 (m, 3H), 6.64-6.63 (m, 1H), 5.31 (s, 2H), 3.73-3.70 (m, 4H), 3.55-3.54 (m, 2H), 3.23-3.22 (m, 2H). MS: m/z 495.3 [M+H]$^+$.

Example 173

5-Chloro-1-(4-fluoro-3-(4-(pyridin-2-yl)piperazine-1-carbonyl)benzyl)quinazoline-2,4(1H,3H)-dione $^1$H NMR (DMSO-$d_6$): 11.70 (s, 1H), 8.12 (dd, J=4.8 and 1.2 Hz, 1H), 7.62-7.52 (m, 2H), 7.45-7.31 (m, 3H), 7.22 (d, J=7.5 Hz, 1H), 7.15 (d, J=8.4 Hz, 1H), 6.75 (d, J=8.7 Hz, 1H), 6.68-6.64 (m, 1H), 5.36 (s, 2H), 3.69-3.21 (m, 8H). MS: m/z 494.3 [M+H]$^+$.

Example 174

6-Chloro-1-(6-fluoro-3-(4-(pyridin-2-yl)piperazine-1-carbonyl)benzyl)quinazoline-2,4(1H,3H)-dione $^1$H NMR (DMSO-$d_6$): 11.86 (s, 1H), 8.08 (d, J=3.9 Hz, 1H), 7.92 (d, J=2.4 Hz, 1H), 7.72 (dd, J=9.0 and 2.4 Hz, 1H), 7.66-7.59 (m, 1H), 7.44-7.32 (m, 2H), 7.24 (d, J=9.0 Hz, 1H), 7.20 (d, J=7.8 Hz, 1H), 6.84 (d, J=7.5 Hz, 1H), 6.70 (t, J=5.4 Hz, 1H), 5.34 (s, 2H), 3.69-3.21 (m, 8H). MS: m/z 494.3 [M+H]$^+$.

Example 175

6-Chloro-1-(5-fluoro-3-(4-(pyrimidin-2-yl)piperazine-1-carbonyl)benzyl)quinazoline-2,4(1H,3H)-dione $^1$H NMR (DMSO-$d_6$): 11.83 (s, 1H), 8.36 (d, J=4.8 Hz, 2H), 7.92 (d, J=2.4 Hz, 1H), 7.70 (d, J=8.7 Hz, 1H), 7.24-7.18 (m, 4H), 6.64 (t, J=4.8 Hz, 1H), 5.34 (s, 2H), 3.69-3.21 (m, 8H). MS: m/z 495.3 [M+H]$^+$.

Example 176

5-Fluoro-1-(5-fluoro-3-(4-(pyrimidin-2-yl)piperazine-1-carbonyl)benzyl)quinazoline-2,4(1H,3H)-dione $^1$H NMR (DMSO-$d_6$): 11.63 (s, 1H), 8.36 (d, J=4.8 Hz, 2H), 7.66-7.61 (m, 1H), 7.29 (d, J=9.3 Hz, 1H), 7.19-7.16 (m, 2H), 7.05-6.98 (m, 2H), 6.65 (t, J=4.8 Hz, 1H), 5.33 (s, 2H), 3.80-3.20 (m, 8H). MS: m/z 479.3 [M+H]$^+$.

Example 177

1-(3-(4-(Cyclopentylpiperazine-1-carbonyl)benzyl)quinazoline-2,4(1H,3H)-dione $^1$H NMR (DMSO-$d_6$): 11.71 (s, 1H), 8.02 (dd, J=8.0 and 1.4 Hz, 1H), 7.63 (t, J=7.1 Hz, 1H), 7.43-7.36 (m, 2H), 7.26-7.21 (m, 4H), 5.34 (s, 2H), 3.65-3.30 (m, 9H), 1.48-1.22 (m, 8H). MS: m/z 4:33 [M+H]$^+$.

Example 178

1-(3-(4-(Cyclopropylcarbonyl)piperazine-1-carbonyl)-4-fluorobenzyl)-6-fluoroquinazoline-2,4(1H,3H)-dione $^1$H NMR (DMSO-$d_6$): 11.84 (s, 1H), 7.74 (dd, J=8.1 and 3.0 Hz, 1H), 7.56 (t, J=8.4 Hz, 1H), 7.45-7.39 (m, 2H), 7.31-7.25 (m, 2H), 5.32 (s, 2H), 3.54-3.16 (m, 8H), 1.92 (m, 1H), 0.73-0.70 (m, 4H). MS: m/z 469.3 [M+H]$^+$.

Example 179

1-(3-(4-(Cyclobutylcarbonyl)piperazine-1-carbonyl)benzyl)-6-fluoroquinazoline-2,4(1H,3H)-dione $^1$H NMR (DMSO-$d_6$): 11.86 (s, 1H), 7.75 (dd, J=8.3 and 2.9 Hz, 1H), 7.56 (t, J=8.7 Hz, 1H), 7.43-7.40 (m, 2H), 7.31-7.26 (m, 3H), 5.35 (s, 2H), 3.52-3.31 (m, 9H), 2.18-1.75 (m, 6H). MS: m/z 465.3 [M+H]$^+$.

Example 180

1-(3-(4-(Cyclobutylcarbonyl)piperazine-1-carbonyl)-4-fluorobenzyl)-6-fluoroquinazoline-2,4(1H,3H)-dione $^1$H NMR (DMSO-$d_6$): 11.84 (s, 1H), 7.74 (d, J=8.1 Hz, 1H), 7.59-7.53 (m, 1H), 7.46-7.44 (m, 1H), 7.37 (d, J=5.7 Hz, 1H), 7.31-7.25 (m, 2H), 5.31 (s, 2H), 3.57-3.11 (m, 9H), 2.14-1.74 (m, 6H). MS: m/z 483.3 [M+H]$^+$.

Example 181

1-(3-(4-(Benzoylpiperazine-1-carbonyl)-4-fluorobenzyl)-6-fluoroquinazoline-2,4(1H,3H)-dione $^1$H NMR (DMSO-$d_6$): 11.84 (s, 1H), 7.74 (dd, J=8.1 and 2.7 Hz, 1H), 7.55-7.53 (m, 1H), 7.46-7.42 (m, 7H), 7.30-7.24 (m, 2H), 5.31 (s, 2H), 3.67-3.20 (m, 8H). MS: m/z 505.3 [M+H]$^+$.

Example 182

1-(3-(4-(Cyclobutylcarbonyl)piperazine-1-carbonyl)-6-fluorobenzyl)-5-fluoroquinazoline-2,4(1H,3H)-dione $^1$H NMR (DMSO-$d_6$): 11.68 (s, 1,H), 7.66-7.59 (m, 1H), 7.36-7.33 (m, 2H), 7.18 (d, J=7.2 Hz, 1H), 7.07-6.96 (m, 2H), 5.32 (s, 2H), 3.60-3.01 (m, 9H), 2.11-1.73 (m, 6H). MS: m/z 483.4

Example 183

1-(3-(4-(Cyclobutylcarbonyl)piperazine-1-carbonyl)-6-fluorobenzyl)-6-fluoroquinazoline-2,4(1H,3H)-dione $^1$H NMR (DMSO-$d_6$): 11.84 (s, 1,H), 7.73 (dd, J=8.1 and 2.7 Hz, 1H), 7.56 (t, J=8.4 Hz, 1H), 7.36-7.30 (m, 2H), 7.24-7.14 (m, 2H), 5.34 (s, 2H), 3.60-3.01 (m, 9H), 2.14-1.72 (m, 6H). MS: m/z 483.3 [M+H]$^+$.

Example 184

5-Fluoro-1-(6-fluoro-3-(4-(furan-2-carbonyl)piperazine-1-carbonyl)benzyl)quinazoline-2,4(1H,3H)-dione $^1$H NMR (DMSO-$d_6$): 11.70 (s, 1H), 7.86 (s, 1H), 7.67-7.59 (m, 1H), 7.39-7.36 (m, 2H), 7.23 (d, J=7.2 Hz, 1H), 7.05-6.97 (m, 3H), 6.65-6.63 (m, 1H), 5.34 (s, 2H), 3.70-3.10 (m, 8H). MS: m/z 495.4 [M+H]$^+$.

Example 185

6-Fluoro-1-(4-fluoro-3-(4-(furan-2-carbonyl)piperazine-1-carbonyl)benzyl)quinazoline-2,4(1H,3H)-dione $^1$H NMR (DMSO-$d_6$): 11.84 (s, 1H), 7.84 (s, 1H), 7.74 (dd, J=8.4 and 3.0 Hz, 1H), 7.59-7.53 (m, 1H), 7.45-7.39 (m, 2H), 7.32-7.26 (m, 2H), 7.02 (d, J=3.3 Hz, 1H), 6.63 (dd, J=3.3 Hz and 1.8 Hz, 1H), 5.32 (s, 2H), 3.67-3.23 (m, 8H). MS: m/z 495.3 [M+H]$^+$.

Example 186

6-Fluoro-1-(5-fluoro-3-(4-(pyrimidin-2-yl)piperazine-1-carbonyl)benzyl)quinazoline-2,4(1H,3H)-dione $^1$H NMR (DMSO-$d_6$): 11.83 (s, 1H), 8.39 (d, J=4.5 Hz, 2H), 7.74 (dd, J=8.3 and 3.2 Hz, 1H), 7.60-7.54 (m, 1H), 7.33-7.29 (m, 2H), 7.27-7.18 (m, 2H), 6.67 (t, J=4.8 Hz, 1H), 5.36 (s, 2H), 3.80-3.35 (m, 8H). MS: m/z 479.4 [M+H]$^+$.

Example 187

1-(6-Chloro-3-(4-(pyrimidin-2-yl)piperazine-1-carbonyl)benzyl)-6-fluoroquinazoline-2,4(1H,3H)-dione $^1$H NMR (DMSO-$d_6$): 11.86 (s, 1H), 8.37 (d, J=4.8 Hz, 2H), 7.76-7.69 (m, 1H), 7.65 (d, J=8.1 Hz, 1H), 7.60-7.59 (m, 1H), 7.38 (dd, J=8.3 and 1.7 Hz, 1H), 7.13-7.09 (m, 2H), 6.65 (t, J=4.7 Hz, 1H), 5.32 (s, 2H), 3.73-3.03 (m, 8H). MS: m/z 495.3 [M+H]$^+$.

Example 188

6-Fluoro-1-(4-fluoro-3-(4-(thiazol-2-yl)piperazine-1-carbonyl)benzyl)quinazoline-2,4(1H,3H)-dione $^1$H NMR (DMSO-$d_6$): 11.82 (s, 1,H), 7.71 (dd, J=8.4 and 3.0 Hz, 1H), 7.58-7.51 (m, 1H), 7.41-7.38 (m, 2H), 7.30-7.23 (m, 2H), 7.17 (d, J=3.6 Hz, 1H), 6.88 (d, J=3.6 Hz, 1H), 5.30 (s, 2H), 3.73-3.26 (m, 8H). MS: m/z 484.3 [M+H]$^+$.

Example 189

5-Fluoro-1-(4-fluoro-3-(4-(thiazol-2-yl)piperazine-1-carbonyl)benzyl)quinazoline-2,4(1H,3H)-dione $^1$H NMR (DMSO-$d_6$): 11.65 (S, 1H), 7.65-7.57 (m, 1H), 7.43-7.38 (m, 2H), 7.27 (t, J=9.0 Hz, 1H), 7.17 (d, J=3.6 Hz, 1H), 7.04-6.98 (m, 2H), 6.87 (d, J=3.6 Hz, 1H), 5.29 (s, 2H), 3.73-3.26 (m, 8H). MS: m/z 484.3 [M+H]$^+$.

Example 190

1-(4-Fluoro-3-(4-(thiazol-2-yl)piperazine-1-carbonyl)benzyl)quinazoline-2,4(1H,3H)-dione $^1$H NMR (DMSO-$d_6$): 11.70 (s, 1H), 8.00 (d, J=8.1 Hz, 1H), 7.64 (t, J=7.9 Hz, 1H), 7.46-7.38 (m, 2H), 7.30-7.22 (m, 3H), 7.17 (d, J=3.6 Hz, 1H), 6.87 (d, J=3.6 Hz, 1H), 5.31 (s, 2H), 3.79-3.23 (m, 8H). MS: m/z 466.3 [M+H]$^+$.

Example 191

1-(3-(4-(Cyclohexylcarbamoyl)piperazine-1-carbonyl)benzyl)quinazoline-2,4(1H,3H)-dione $^1$H NMR (DMSO-$d_6$): 11.67 (s, 1H), 8.01 (d, J=7.8 Hz, 1H), 7.63 (t, J=7.8 Hz, 1H), 7.40-7.37 (m, 2H), 7.30-7.22 (m, 4H), 6.20 (d, J=4.0 Hz, 1H), 5.33 (s, 2H), 3.80-3.00 (m, 9H), 1.80-1.00 (m, 10H). MS: m/z 490.4 [M+H]$^+$.

The following salts were prepared from the corresponding free base via stirring the free base in HCl/ethyl acetate for 2.5 h at room temperature, followed by evaporation of the solvents.

Example 192

1-(4-Fluoro-3-(4-(pyrimidin-2-yl)piperazine-1-carbonyl)benzyl)quinazoline-2,4(1H,3H)-dione hydrochloride $^1$H NMR (DMSO-$d_6$): 11.71 (s, 1H), 8.38 (d, J=4.8 Hz, 2H), 8.00 (d, J=6.9 Hz, 1H), 7.64 (t, J=7.8 Hz, 1H), 7.46-7.39 (m, 2H), 7.30-7.21 (m, 3H), 6.67 (t, J=4.8 Hz, 1H), 5.31 (s, 2H), 3.81-3.78 (m, 2H), 3.67-3.62 (m, 4H), 3.24-3.20 (m, 2H). MS: m/z 461.2 [M+H]$^+$.

Example 193

5-Fluoro-1-(4-fluoro-3-(4-(pyrimidin-2-yl)piperazine-1-carbonyl)benzyl)quinazoline-2,4(1H,3H)-dione hydrochloride $^1$H NMR (DMSO-$d_6$): 11.66 (s, 1H), 8.41 (d, J=4.5 Hz, 2H), 7.67-7.59 (m, 1H), 7.47-7.39 (m, 2H), 7.28 (t, J=4.5 Hz, 1H), 7.06-6.99 (m, 2H), 6.70 (t, J=4.8 Hz, 1H), 5.31 (s, 2H), 3.82-3.81 (m, 2H), 3.69-3.64 (m, 4H), 3.25-3.22 (m, 2H). MS: m/z 479.3 [M+H]+.

Example 194

1-(3-(4-(Pyrimidin-2-yl)piperazine-1-carbonyl)benzyl)quinazoline-2,4(1H,3H)-dione hydrochloride 1H NMR (DMSO-d6): 11.72 (s, 1H), 8.37 (d, J=4.8 Hz, 2H), 8.01 (d, J=6.9 Hz, 1H), 7.64 (t, J=6.9 Hz, 1H), 7.50-7.20 (m, 6H), 6.66 (t, J=4.7 Hz, 1H), 5.35 (s, 2H), 4.10-3.20 (m, 8H). MS: m/z 443.3 [M+H]+.

Example 195

1-(3-((4-(Pyridin-2-yl)piperazin-1-yl)methyl)benzyl)quinazoline-2,4(1H,3H)-dione a) 1-(3-(Hydroxymethyl)benzyl)quinazoline-2,4(1H,3H)-dione: To the solution of 1-(3-methoxycarbonylbenzyl)quinazoline-2,4(1H,3H)-dione (0.5 g, 1.6 mmol) in THF (30 mL) and ethanol (10 mL) was added NaBH4 (1.2 g, 32 mmol) at room temperature under N2. It was stirred at room temperature for 4 h, then refluxed overnight. The reaction mixture was quenched with HCl (2N), then concentrated. The residue was diluted with H2O (10 mL), and it was extracted with ethyl acetate (3×10 mL). The combined organic layers were washed with brine, dried over anhydrous Na2SO4, and concentrated to afford the crude product, which was used for the next reaction without purification.

b) 1-(3-(Methanesulfonoylmethyl)benzyl)quinazoline-2,4(1H,3H)-dione: To a solution of 1-(3-(hydroxymethyl)benzyl)quinazoline-2,4(1H,3H)-dione (0.1 g, 0.35 mmol) and triethylamine (0.1 g, 1.1 mmol) in dry DCM (2 mL) was added MsCl dropwise at 10° C. under N2. The mixture was stirred for 2 h, and was used for the next reaction directly.

c) 1-(3-((4-(Pyridin-2-yl)piperazin-1-yl)methyl)benzyl)quinazoline-2,4(1H,3)-dione: A solution of 1-(pyridin-2-yl)piperazine (0.057 g, 0.35 mmol) in dry DCM (0.2 mL) was added to the above solution at room temperature under N2, and the mixture was refluxed overnight. The reaction mixture was concentrated, and the residue was diluted with H2O (2 mL). It was extracted with ethyl acetate (3×10 mL). The combined organic layers was washed with brine, dried with anhydrous Na2SO4, and concentrated. The crude product was purified by preparative TLC to give the title compound (5 mg) as white solid. 1H NMR (DMSO-d6): 8.09 (d, J=3.3 Hz, 1H), 8.02 (d, J=6.6 Hz, 1H), 7.66-7.61 (m, 1H), 7.54-7.48 (m, 1H), 7.29-7.15 (m, 6H), 6.78 (d, J=8.7 Hz, 1H), 6.64-6.59 (m, 1H), 5.32 (s, 2H), 3.42-3.39 (m, 4H), 2.40-2.37 (m, 4H). MS: m/z 428.3 [M+H]+.

The following compounds were prepared from 1-(3-aminobenzyl)quinazoline-2,4(1H,3H)-dione (prepared from quinazoline-2,4(1,H,3H)-dione and 1-(bromomethyl)-3-nitrobenzene followed by reduction) and the corresponding substituted acetic acid using a procedure similar to those described for the synthesis of compound of Example 3.

Example 196

1-(3-(Naphthalen-2-yl)acetamidobenzyl)quinazoline-2,4(1H,3)-dione

1H NMR (DMSO-d6): 11.72 (brs, 1H), 10.23 (s, 1H), 8.10-7.99 (m, 1H), 7.90-7.76 (m, 4H), 7.62-7.56 (m, 2H), 7.46-7.38 (m, 4H), 7.26-7.16 (m, 3H), 7.05-6.90 (m, 1H), 5.25 (s, 2H), 3.75 (s, 2H). MS: m/z 436.4 [M+H]+.

Example 197

1-(3-(3,4-Dimethoxyphenyl)acetamidobenzyl)quinazoline-2,4(1H,3)-dione

1H NMR (DMSO-d6): 11.70 (brs, 1H), 10.03 (s, 1H), 8.01 (dd, J=7.8 and 1.2 Hz, 1H), 7.65-7.55 (m, 2H), 7.34 (s, 1H), 7.27-7.17 (m, 3H), 6.98 (d, J=7.8 Hz, 1H), 6.83-6.77 (m, 3H), 5.26 (s, 2H), 3.69(s, 6H), 3.47 (s, 2H). MS: m/z 446.3 [M+H]+.

Example 198

1-(3-([1,2,4]Triazolo[4,3-a]pyridine-6-carbonyl)benzyl)quinazoline-2,4(1H,3)-dione a) 1-(3-(N-Methoxy-N-methylcarbamoyl)benzyl)quinazoline-2,4(1H,3)-dione: To a solution of 1-(3-carboxybenzyl)quinazoline-2,4(1H,3H)-dione (0.5 g, 1.68 mmol), HATU (0.96 g, 2.53 mmol) and DIEA (0.9 g, 7 mmol) in dry DCM (20 mL) was added N,O-dimethylhydroxylamine hydrochloride (0.2 g, 2.0 mmol) at room temperature under N2, then the mixture was heated to 4° C. and stirred overnight. The reaction solution was concentrated, the residue was diluted with H2O and it was extracted with ethyl acetate (3×10 mL). The combined organic layers were washed with water and brine, dried over anhydrous Na2SO4 and concentrated. The crude product was purified via chromatography to give the title compound (0.4 g, 70% yield).

b) 1-(3-([1,2,4]triazolo[4,3-a]pyridine-6-carbonyl)benzyl)quinazoline-2,4(1/13H)-dione: To a solution of 6-bromo-[1,2,4]triazolo[4,3-a]pyridine (35 mg, 0.18 mmol) in anhydrous THF (1 mL) was added n-BuLi (0.15 mL, 0.38 mmol) dropwise at −65° C. under N2, then it was maintained at this temperature for 3 h. To this solution was added dropwise a solution of 1-(3-(N-methoxy-N-methylcarbamoyl)benzyl)quinazoline-2,4(1H,3H)-dione (50 mg, 0.15 mmol) in THF (1 mL), then it was stirred for 4 h at −65° C. It was allowed to warm to 0° C. for over 4 h. The reaction solution was poured into saturated aqueous NH4Cl, extracted with ethyl acetate (3×10 mL). The combined organic layers were washed with brine, dried over anhydrous Na2SO4, and concentrated. The crude product was purified by preparative TLC to give the title compound (6.5 mg, 11% yield) as white solid. 1H NMR (CDxOD+CDCl3): 9.42 (d, J=7.2 Hz, 1H), 8.41-8.39 (m, 2H), 8.10 (d, J=7.2 Hz, 1H), 7.95 (d, J=9.0 Hz, 1H), 7.58-7.45 (m, 4H), 7.18-7.11 (m, 3H), 5.38 (s, 2H). MS: m/z 398.2 [M+H]+.

The following compounds were prepared from the corresponding substituted 1-(3-carboxybenzyl)quinazoline-2,4 (1H,3H)-dione or 1-((2-carboxylpyridin-6-yl)methyl)quinazoline-2,4(1H,3H)-dione and substituted amine using a procedure similar to those described for the synthesis of compound of Example 3.

Example 199

6-Fluoro-1-((2-(4-(pyrimidin-2-yl)piperazine-1-carbonyl)pyridin-6-yl)methyl)quinazoline-2,4(1H,3H)-dione 1H NMR (DMSO-d6): 11.84 (s, 1H), 8.39 (d, J=4.8 Hz, 2H), 7.94 (t, J=7.8 Hz, 1H), 7.72-7.70 (m, 1H), 7.57-7.53

(m, 3H), 7.34-7.30 (m, 1H), 6.67 (t, J=4.8 Hz, 1H), 5.46 (s, 2H), 3.73-3.63 (m, 4H), 3.42-3.32 (m, 4H). MS: m/z 462.5 [M+H]$^+$.

Example 200

5-Fluoro-1-(4-fluoro-3-(4-methoxybenzylcarbamoyl)benzyl)quinazoline-2,4 (1H,3H)-dione $^1$H NMR (DMSO-d$_6$): 11.70 (s, 1H), 8.79 (t, J=5.3 Hz, 1H), 7.66-7.57 (m, 2H), 7.46-7.41 (m, 1H), 7.27-7.20 (m, 3H), 7.08-6.99 (m, 2H), 6.90-6.87 (m, 2H), 5.30 (s, 2H), 4.37 (d, J=6.0 Hz, 2H), 3.73 (s, 3H). MS: m/z 452.2 [M+H]$^+$.

Example 201

1-(3-(3-Chlorobenzylcarbamoyl)-4-fluorobenzyl)-5-fluoroquinazoline-2,4 (1H,3H)-dione $^1$H NMR (DMSO-d$_6$): 11.70 (s, 1H), 9.01 (t, J=5.1 Hz, 1H), 7.75-7.68 (m, 2H), 7.57-7.52 (m, 1H), 7.48-7.32 (m, 5H), 7.18-7.08 (m, 2H), 5.31 (s, 2H), 4.45 (d, J=5.7 Hz, 2H). MS: m/z 456.1 [M+H]$^+$.

Example 202

1-(3-(Benzylcarbamoyl)-4-fluorobenzyl)-5-fluoroquinazoline-2,4 (1H,3H)-dione $^1$H NMR (DMSO-d$_6$): 11.70 (s, 1H), 8.87 (t, J=5.1 Hz, 1H), 7.67-7.59 (m, 2H), 7.47-7.42 (m, 1H), 7.36-7.22 (m, 6H), 7.09-6.99 (m, 2H), 5.31 (s, 2H), 4.45 (d, J=6.0 Hz, 1H). MS: m/z 422.3 [M+H]$^+$.

Example 203

5-Methoxy-1-(3-(4-(pyrimidin-2-yl)piperazine-1-carbonyl)benzyl)quinazoline-2,4 (1H,3H)-dione $^1$H NMR (DMSO-d$_6$): 11.32 (s, 1H), 8.38 (d, J=4.8 Hz, 2H), 7.53 (t, J=8.4 Hz, 1H), 7.44-7.29 (m, 4H), 6.85 (d, J=8.4 Hz, 1H), 6.75 (d, J=8.4 Hz, 1H), 6.67 (t, J=4.8 Hz, 1H), 5.33 (s, 2H), 3.84 (s, 3H), 3.79-3.42 (m, 8H). MS: m/z 473.3 [M+H]$^+$.

Example 204

6-Methoxy-1-(3-(4-(pyrimidin-2-yl)piperazine-1-carbonyl)benzyl)quinazoline-2,4 (1H,3H)-dione $^1$H NMR (DMSO-d$_6$): 11.71 (s, 1H), 8.38 (d, J=4.8 Hz, 2H), 7.47-7.40 (m, 3H), 7.34-7.26 (m, 3H), 7.20 (d, J=9.3 Hz, 1H), 6.67 (t, J=4.8 Hz, 1H), 5.35 (s, 2H), 3.80 (s, 3H), 3.63-3.46 (m, 8H). MS: m/z 473.3 [M+H]$^+$.

Example 205

1-(3-(5-Bromopyrimidin-2-aminocarbamoyl)-4-fluorobenzyl)-5-fluoroquinazoline-2,4 (1H,3H)-dione $^1$H NMR (DMSO-d$_6$): 11.73 (s, 1H), 10.27 (s, 1H), 9.43 (s, 1H), 8.50 (s, 2H), 7.68-7.52 (m, 3H), 7.28 (t, J=9.3 Hz, 1H), 7.11-7.00 (m, 2H), 5.33 (s, 2H). MS: m/z 503.0 [M+H]$^+$.

Example 206

1-(3-(4-(Pyrimidin-2-yl)piperazine-1-carbonyl)benzyl)-7-(trifluoromethyl)quinazoline-2,4 (1H,3H)-dione $^1$H NMR (300 M, DMSO-d$_6$): 11.96 (s, 1H), 8.36 (d, J=4.8 Hz, 2H), 8.19 (d, J=8.1 Hz, 1H), 7.55 (d, J=8.4 Hz, 1H), 7.47 (s, 1H), 7.43-7.39 (m, 3H), 7.33-7.30 (m, 1H), 6.65 (t, J=4.7 Hz, 1H), 5.44 (s, 2H), 3.59-3.46 (m, 8H). MS: m/z 511.2 [M+H]$^+$.

Example 207

6,7-Ethylenedioxo-1-(3-(4-(pyrimidin-2-yl)piperazine-1-carbonyl)benzyl)quinazoline-2,4 (1H,3H)-dione $^1$H NMR (DMSO-d$_6$): 11.55 (s, 1H), 8.39 (d, J=4.8 Hz, 2H), 7.44-7.34 (m, 5H), 6.75 (s, 1H), 6.67 (t, J=4.8 Hz, 1H), 5.29 (s, 2H), 4.32-4.27 (m, 4H), 3.88-3.56 (m, 8H). MS: m/z [M+H]$^+$.

Example 208

5-Fluoro-1-(6-methoxy-3-(4-(pyrimidin-2-yl)piperazine-1-carbonyl)benzyl)quinazoline-2,4 (1H,3H)-dione $^1$H NMR (DMSO-d$_6$): 11.65 (s, 1H), 8.37 (d, J=4.8 Hz, 2H), 7.67-7.60 (m, 1H), 7.39 (dd, J=8.4 and 1.8 Hz, 1H), 7.16 (d, J=8.4 Hz, 1H), 7.07-6.98 (m, 2H), 6.87 (d, J=8.4 Hz, 1H), 6.65 (t, J=4.7 Hz, 1H), 5.20 (s, 2H), 3.95 (s, 3H), 3.82-3.16 (m, 8H). MS: m/z 491.2 [M+H]$^+$.

Example 209

7-Methoxy-1-(3-(4-(pyrimidin-2-yl)piperazine-1-carbonyl)benzyl)quinazoline-2,4 (1H,3H)-dione $^1$H NMR (DMSO-d$_6$): 11.54 (s, 1H), 8.37 (d, J=4.8 Hz, 2H), 7.92 (d, J=8.7 Hz, 1H), 7.42-7.30 (m, 4H), 6.84 (dd, J=8.9 and 2.3 Hz, 1H), 6.68-6.63 (m, 2H), 5.34 (s, 2H), 3.76 (s, 3H), 3.71-3.51 (m, 8H). MS: m/z 473.3 [M+H]$^+$.

Example 210

5-Fluoro-1-(4-fluoro-3-(4-(tetrahydrofuran-2-carbonyl)piperazine-1-carbonyl)benzyl)quinazoline-2,4 (1H,3H)-dione $^1$H NMR (DMSO-d$_6$): 11.67 (s, 1H), 7.66-7.59 (m, 1H), 7.47-7.42 (m, 1H), 7.38 (d, J=6.0 Hz, 1H), 7.28 (t, J=9.0 Hz, 1H), 7.10-6.95 (m, 2H), 5.30 (s, 2H), 4.75-4.50 (m, 1H), 3.85-3.45 (m, 8H), 3.25-3.00 (m, 2H), 2.15-1.70 (m, 4H). MS: m/z 499.3 [M+H]$^+$.

Example 211

5-Fluoro-1-(4-nitro-3-(4-(pyrimidin-2-yl)piperazine-1-carbonyl)benzyl)quinazoline-2,4 (1H,3H)-dione $^1$H NMR (DMSO-d$_6$): 11.71 (s, 1H), 8.40 (d, J=3.9 Hz, 2H), 8.17 (d, J=8.7 Hz, 1H), 7.63-7.57 (m, 3H), 7.07-6.94 (m, 2H), 6.69 (t, J=4.4 Hz, 1H), 5.45 (s, 2H), 3.85-3.84 (m, 2H), 3.70-3.69 (m, 2H), 3.61-3.59 (m, 2H), 3.21-3.18 (m, 2H). MS: m/z 506.2 [M+H]$^+$.

Example 212

1-(3-(4-Cyclohexylpiperazine-2-carbonyl)-4-fluorobenzyl)-5-fluoroquinazoline-2,4 (1H,3H)-dione $^1$H NMR (DMSO-d$_6$): 11.68 (s, 1H), 7.66-7.58 (m, 1H), 7.45-7.40 (m, 1H), 7.30-7.23 (m, 2H), 7.06-6.99 (m, 2H), 5.30 (s, 2H), 3.56-3.07 (m, 8H), 2.33-2.25 (m, 1H), 1.72-1.04 (m, 10H). MS: m/z 483.5 [M+H]$^+$.

Example 213

5-Fluoro-1-(4-fluoro-3-(4-phenylpiperazine-1-carbonyl)benzyl)quinazoline-2,4 (1H,3H)-dione $^1$H NMR (DMSO-d$_6$): 11.68 (s, 1H), 7.67-7.60 (m, 1H), 7.48-7.38 (m, 2H), 7.32-7.20 (m, 3H), 7.07-7.00 (m, 2H), 6.94-6.91 (m, 2H), 6.82 (t, J=7.2 Hz, 1H), 5.31 (s, 2H), 3.85-3.65 (m, 2H), 3.45-3.10 (m, 4H), 3.10-2.90 (m, 2H). MS: m/z 477.4 [M+H]$^+$.

Example 214

5-Fluoro-1-(4-fluoro-3-(4-phenylpiperidine-1-carbonyl)benzyl)quinazoline-2,4 (1H,3H)-dione $^1$H NMR (DMSO-d$_6$): 11.68 (s, 1H), 7.62-7.56 (m, 1H), 7.45-7.37 (m, 2H), 7.33-7.18 (m, 6H), 7.04-6.93 (m, 2H), 5.45-5.15 (m, 2H), 4.70-4.55 (m, 1H), 3.50-3.05 (m, 2H), 2.95-2.65 (m, 2H), 1.80-1.20 (m, 4H). MS: m/z 476.4 [M+H]$^+$.

Example 215

1-(4-Bromo-3-(4-(pyrimidin-2-yl)piperazine-1-carbonyl)benzyl)-5-fluoroquinazoline-2,4 (1H,3H)-dione $^1$H NMR (DMSO-d$_6$): 11.67 (s, 1H), 8.30 (d, J=4.8 Hz, 2H), 7.66-7.58 (m, 2H), 7.37 (d, J=1.8 Hz, 1H), 7.34 (dd, J=8.4 and 2.1 Hz, 1H), 7.06-6.97 (m, 2H), 6.66 (t, J=4.8 Hz, 1H), 5.37-5.22 (m, 2H), 3.82-3.11 (m, 8H). MS: m/z 539.3 [M+H]$^+$.

Example 216

6,7-Methylenedioxo-1-(3-(4-(pyrimidin-2-yl)piperazine-1-carbonyl)benzyl)quinazoline-2,4 (1H,3H)-dione $^1$H NMR (DMSO-d$_6$): 11.64 (s, 1H), 8.39 (d, J=4.5 Hz, 2H), 7.44-7.32 (m, 5H), 6.95 (s, 1H), 6.67 (t, J=4.4 Hz, 1H), 6.14 (s, 2H), 5.33 (s, 2H), 3.81-3.65 (m, 8H). MS: m/z 487.2 [M+H]$^+$.

Example 217

1-(3-(4-(Cyclohexylmethyl)piperazine-1-carbonyl)-4-fluorobenzyl)-5-fluoroquinazoline-2,4 (1H,3H)-dione $^1$H NMR (DMSO-d$_6$): 11.70 (s, 1H), 7.66-7.58 (m, 1H), 7.44-7.40 (m, 1H), 7.32-7.23 (m, 2H), 7.05-6.99 (m, 2H), 5.30 (s, 2H), 3.70-3.50 (m, 2H), 3.20-3.00 (m, 2H), 2.38-2.28 (m, 2H), 2.20-2.10 (m, 2H), 2.05 (d, J=6.6 Hz, 2H), 1.73-1.63 (m, 5H), 1.45-1.39 (m, 1H), 1.30-1.00 (m, 3H), 0.90-0.70 (m, 2H). MS: m/z 497.3 [M+H]$^+$.

Example 218

8-Fluoro-1-(3-(4-(pyrimidin-2-yl)piperazine-1-carbonyl)benzyl)quinazoline-2,4 (1H,3H)-dione $^1$H NMR (DMSO-d$_6$): 11.93 (s, 1H), 8.38 (d, J=4.8 Hz, 2H), 7.89 (d, J=7.8 Hz, 1H), 7.60-7.52 (m, 1H), 7.45-7.22 (m, 5H), 6.66 (t, J=4.8 Hz, 1H), 5.40 (s, 2H), 3.90-3.20 (m, 8H). MS: m/z 461.2 [M+H]$^+$.

Example 219

6-Amino-1-(3-(4-(pyrimidin-2-yl)piperazine-1-carbonyl)benzyl)quinazoline-2,4(1H,3H)-dione A mixture of 6-nitro-1-(3-(4-(pyrimidin2-yl)piperazine-1-carbonyl)benzyl)-quinazoline-2,4(1H,3H)-dione (50 mg, 0.10 mmol) in EtOH (10 mL) with Fe powder (33.5 mg, 0.60 mmol) and sat. NH$_4$Cl solution (0.2 mL) were refluxed under N$_2$ overnight. The mixture was filtered to remove the solid. The solution was concentrated and purified by flash chromatography (DCM:MeOH=50:3) to give the title compound (10.79 mg, 23.6% yield) as yellow solid. $^1$H NMR (DMSO-d$_6$): 11.46 (s, 1H), 8.39 (d, J=4.8 Hz, 2H), 7.42-7.31 (m, 4H), 7.20 (d, J=2.7 Hz, 1H), 7.00 (d, J=8.7 Hz, 1H), 6.89 (dd, J=8.7 and 2.7 Hz, 1H), 6.67 (t, J=4.8 Hz, 1H), 5.26 (s, 4H), 3.81-3.68 (m, 8H). MS: m/z 458.3 [M+H]$^+$.

Example 220

1-(2-(4-(Pyrimidin-2-yl)piperazine-1-carbonyl)benzyl)quinazoline-2,4 (1H,3H)-dione The title compound was prepared from 1-(2-carboxybenzyl)quinazoline-2,4(1H,3H)-dione (prepared from quinazoline-2,4(1H,3H)-dione and methyl 2-(bromomethyl)benzoate using a procedure similar to those used for compounds of Example 1 and 2), and 2-(piperazin-1-yl)pyrimidine using a procedure similar to that described for the synthesis of compound of Example 3. $^1$H NMR (DMSO-d$_6$): 11.76 (s, 1H), 8.40 (d, J=4.8 Hz, 2H), 8.03-8.00 (m, 1H), 7.70-7.50 (m, 1H), 7.35-7.00 (m, 6H), 6.68 (t, J=4.8 Hz, 1H), 5.25 (s, 2H), 4.10-3.60 (m, 8H). MS: m/z 443.2 [M+H]$^+$.

Example 221

1-(3-(4-(Pyrimidin-2-yl)piperazine-1-carbonyl)phenyl)quinazoline-2,4 (1H,3H)-dione a) Methyl 3-(3-(2-bromobenzoyl)ureido)benzoate: To a solution of 2-bromobenzamide (2.0 g, 10.0 mmol) in DCM (30 mL) was added oxalyl chloride (1.65 g, 13.0 mmol) and it was heated under reflux for 23 h. To the reaction mixture was added methyl 3-aminobenzoate (1.66 g, 11.0 mmol) and it was stirred for 20 min. The mixture was poured into water, and the precipitate was filtered. It was recrystallized from ethanol to give the crude product (1.80 g, 48%), which was used for the next step without further purification.
b) 1-(3-Methoxycarbonylphenyl)quinazoline-2,4(1H, 3H)-dione: A mixture of methyl 3-(3-(2-bromobenzoyl) ureido)benzoate (1.8 g. 4.8 mmol), potassium tert-butoxide (2.69 g, 24 mmol) and DMF (20 mL) was stirred at 70-80° C. under nitrogen for 2.25 h. It was cooled, diluted with water, and the mixture was filtered. The crude product was purified by preparative TLC (EtOAc) to give the title compound (0.34 g, 24% yield) as white solid. MS: m/z 297 [M+H]⁺.

c) 1-(3-Carboxyphenyl)quinazoline-2,4(1H,3H)-dione: The title compound was prepared from 1(3-methoxycarbonylphenyl)quinazoline-2,4(1H,3H)-dione and NaOH using a procedure similar to those of compound of Example 2, and was isolated as white solid. MS: m/z 283 [M+H]⁺.

d) 1-(3-(4-(Pyrimidin-2-yl)piperazine-1-carbonyl)phenyl)quinazoline-2,4(1H,3H)-dione: The title compound was prepared from 1-(3-carboxyphenyl)quinazoline-2,4(1H,3H)-dione and 2-(piperazin-1-yl)pyrimidine using a procedure similar to those of compound of Example 3, and was isolated as white solid. ¹H NMR (DMSO-d₆): 11.72 (s, 1H), 8.36 (d, J=4.8 Hz, 2H), 8.02 (d, J=6.6 Hz, 1H), 7.69-7.55 (m, 5H), 7.25 (t, J=7.5 Hz, 1H), 6.65 (t, J=4.7 Hz, 1H), 6.48 (d, J=8.4 Hz, 1H), 3.80-3.20 (m, 8H). MS: m/z 429.1 [M+H]⁺.

Example 222

8-Chloro-1-(3-methoxycarbonylbenzyl)quinazoline-2,4(1H,3H)-dione and 8-chloro-3-(3-methoxycarbonylbenzyl)quinazoline-2,4(1H,3H)-dione To a suspension of 8-chloroquinazoline-2,4(1H,3H)-dione (5.1 g, 25.9 mmol) in toluene (50 mL) and hexamethyldisilazane (HMDS, 10.4, g, 64.9 mmol) was added sulfuric acid (0.25 g, 2.6 mmol). The mixture was heated to reflux and refluxed for 8 h until a clear solution was obtained. The solvent and excessive HMDS was removed via vacuum evaporation, and methyl 3-(bromomethyl)benzoate (5.9 g, 25.9 mmol) and DMF (1 mL) was added to the residue. The reaction mixture was heated to 160° C. and was stirred at this temperature for 3 h. It was diluted with 1,4-dioxane (6 mL) at 100° C., and then methanol (10 mL) was added at 70° C. and it was stirred for 30 min. The mixture was cooled to 5° C. and the precipitates were collected. The solids was washed with methanol (10 mL) and water (20 mL), dried under vacuum for 12 h to give the title compound 8-chloro-3-(3-methoxycarbonylbenzyl)quinazoline-2,4(1H,3H)-dione (2.6 g, 29.1% yield) as gray solid. MS: m/z 477.1 [M+H]⁺. The filtrate was concentrated, and the residue was purified by preparative TLC (PE:EA=1:1) to give the other title compound 8-chloro-1-(3-methoxycarbonylbenzyl)quinazoline-2,4(1H,3H)-dione (0.2 g, 1.8%) as yellow solid. MS: m/z 477.1 [M+H]⁺.

Example 223

8-Chloro-3-(3-(4-(pyrimidin-2-yl)piperazine-1-carbonyl)benzyl)quinazoline-2,4(1H,3H)-dione The compound was prepared from 8-chloro-3-(3carboxybenzyl)quinazoline-2,4(1H,3H)-dione (prepared from 8-Chloro-3 (3-methoxycarbonylbenzyl)quinazoline-2,4(1H, 3H)-dione and NaOH using a procedure similar to those of compound of Example 2), and 2-(piperazin-1-yl)pyrimidine using, a procedure similar to those described for the synthesis of compound of Example 3. ¹H NMR (DMSO-d₆): 11.15 (s, 1H), 8.38 (d, J=4.8 Hz, 2H), 7.95 (d, J=7.8 Hz, 1H), 7.82 (d, J=7.5 Hz, 1H), 7.50-7.30 (m, 4H), 7.23 (t, J=7.8 Hz, 1H), 6.67 (t, J=4.8 Hz, 1H), 5.14 (s, 2H), 3.90-3.55 (m, 8H). MS: m/z 477.1 [M+H]⁺.

Example 224

8-Chloro-1-(3-(4-(pyrimidin-2-yl)piperazine-1-carbonyl)benzyl)quinazoline-2,4(1H,3H)-dione The compound was prepared from 8-chloro-1-(3-carboxybenzyl)quinazoline-2,4(1H,3H)-dione (prepared from 8-chloro-1-(3-methoxycarbonylbenzyl)quinazoline-2,4(1H, 3H)-dione and NaOH using a procedure similar to those of compound of Example 2), and 2-(piperazin-1-yl)pyrimidine using a procedure similar to those described for the synthesis of compound of Example 3. ¹H NMR (DMSO-d₆): 11.94 (s, 1H), 8.38 (d, J=4.8 Hz, 2H), 8.05 (d, J=6.6 Hz, 1H), 7.77 (d, J=6.6 Hz, 1H), 7.50-7.20 (m, 5H), 6.66 (t, J=4.8 Hz, 1H), 5.53 (s, 2H), 3.90-3.50 (m, 8H). MS: m/z 477.1 [M+H]⁺.

Example 225

8-Methyl-3-(3-(4-(pyrimidin-2-yl)piperazine-1-carbonyl)benzyl)quinazoline-2,4(1H,3H)-dione The compound was prepared from 8-methyl-3-(3-carboxybenzyl)quinazoline-2,4(1H,3H)-dione (prepared from 8-methylquinazoline-2,4(1H,3H)-dione and methyl 3-(bromomethyl)benzoate using a procedure similar to those used for Examples 222 and 223), and 2-(piperazin-1-yl)pyrimidine using a procedure similar to those described for the synthesis of compound of Example 3. ¹H NMR (DMSO-d₆): 10.81 (s, 1H), 8.36 (d, J=4.5 Hz, 2H), 7.83 (d, J=7.5 Hz, 1H), 7.52 (d, J=7.2 Hz, 1H), 7.45-7.30 (m, 4H), 7.13 (t, J=7.7 Hz, 1H), 6.67 (t, J=4.7 Hz, 1H), 5.15 (s, 2H), 3.92-3.46 (m, 8H), 2.36 (s, 3H). MS: m/z 457.3 [M+H]⁺.

Example 226

8-Methyl-1-(3-(4-(pyrimidin-2-yl)piperazine-1-carbonyl)benzyl)quinazoline-2,4(1H,3H)-dione a) 8-Methyl-1H-benzo[d][1,3]oxazine-2,4-dione: To a solution of 2-amino-3-methylbenzoic acid (5.03 g, 33.3 mmol) in THF (50 mL) was added triphosgene (9.92 g, 33.4 mmol). The mixture was stirred at room temperature for 15 min and then filtered. The precipitate was washed by THF and water, dried to give the title compound (5.10 g, 86.4% yield) as white solid. MS: m/z 178.1 [M+H]⁺.

b) 2-Amino-N-tert-butyl-3-methylbenzamide: To a solution of 8-methyl-1H-benzo[d][1,3]oxazine-2,4-dione (3.89 g, 22.0 mmol) in DMF (30 mL) were added DMAP (0.27 g, 2.2 mmol) and tert-butylamine (2.55 mL, 24.1 mmol). It was stirred at room temperature overnight, then the mixture was poured into water and the precipitate was filtered. The solid was washed with water and dried to give the product (1.68 g, 37.1% yield). MS: m/z 207.2 [M+H]⁺.

c) 3-Tert-butyl-8-methylquinazoline-2,4(1H,3H)-dione: To a solution of 2-amino-N-tert-butyl-3-methylbenzamide (0.52 g, 2.5 mmol) in THF (20 mL) were added CDI (0.85 g, 5.2 mmol). It was refluxed overnight, cooled to room temperature, then the mixture was poured into water and the precipitate was filtered. The solid was washed with water and dried to give the title compound (0.25 g, 42.6% yield). ¹H NMR (DMSO-d₆): 10.33 (s, 1H), 7.68 (d, J=7.8 Hz, 1H), 7.41 (d, J=7.2 Hz, 1H), 7.04 (t, J=7.6 Hz, 1H), 2.31 (s, 3H), 1.66 (s, 9H).

d) 3-Tert-butyl-8-methyl-1-(3-methoxycarbonylbenzyl) quinazoline-2,4(1H,3H)-dione: A mixture of 3-tert-butyl-8-methylquinazoline-2,4(1H,3H)-dione (1.00 g, 4.3 mmol), methyl 3-(bromomethyl)benzoate (0.99 g, 4.3 mmol) and MeONa (0.28 g, 5.2 mmol) in DMF (15 mL) was stirred at 50° C. overnight. The resulting mixture was used directly for next step reaction. MS: m/z 403.2 [M+H]$^+$.

e) 8-Methyl-1-(3-carboxybenzyl)quinazoline-2,4(1H,3H)-dione: To the reaction mixture from above was added 6N HCl (a.q., 40 mL), and the mixture was heated at 80° C. for 6 h. It was cooled to room temperature, poured into water and the precipitate was filtered. The solid was washed with water and dried to give the title compound (0.27 g, 20.1% yield). MS: m/z 311.1 [M+H]$^+$.

f) 8-Methyl-1-(3-(4-(pyrimidin-2-yl)piperazine-1-carbonyl)benzyl)quinazoline-2,4(1H,3H)-dione: The title compound was prepared from 8-methyl-1-(3-carboxybenzyl)quinazoline-2,4(1H,3H)-dione and 2-(piperazin-1-yl)pyrimidine using a procedure similar to those described for the synthesis of compound of Example 3. $^1$H NMR (DMSO-$d_6$): 11.70 (s, 1H), 8.38 (d, J=4.8 Hz, 2H), 7.92 (d, J=6.9 Hz, 1H), 7.50-7.26 (m, 5H), 7.17 (t, J=7.5 Hz, 1H), 6.65 (t, J=4.8 Hz, 1H), 5.35 (s, 2H), 3.85-3.15 (m, 8H), 2.35 (s, 3H). MS: m/z 457.2 [M+H]$^+$.

Example 227

8-Methoxy-1-(3-(4-(pyrimidin-2-yl)piperazine-1-carbonyl)benzyl)quinazoline-2,4(1H,3H)-dione The compound was prepared from 2-amino-3-methoxylbenzoic acid using procedures similar to those described for the synthesis of compound of Example 226. $^1$H NMR (DMSO-$d_6$): 11.76 (s, 1H), 8.38 (d, J=4.8 Hz, 2H), 7.65 (d, J=6.6 Hz, 1H), 7.45-7.17 (m, 6H), 6.67 (t, J=4.7 Hz, 1H), 5.51 (s, 2H), 3.80-3.64 (m, 8H), 3.56 (s, 3H). MS: m/z 473.2 [M+H]$^+$.

Example 228

3-(3-(4-(Pyrimidin-2-yl)piperazine-1-carbonyl)benzyl)quinazoline-2,4(1H,3H)-dione a) 3-(3-Methoxycarbonylbenzyl)quinazoline-2,4(1H,3H)-dione: A suspension of quinazoline-2,4(1H,3H)-dione (2.5 g, 15.4 mmol), methyl 3-(bromomethyl)benzoate (3.56 g, 15.4 mmol) and K$_2$CO$_3$(4.26 g, 30.8 mmol) in DMF (30 mL) was stirred at room temperature overnight. To the mixture was added 150 mL water and the precipitates were collected. The crude product was purified by chromatography on silica (CH$_2$Cl$_2$: MeOH=200:1) to give the title compound (0.87 g, 18.2% yield) as white solid. $^1$H NMR (DMSO-$d_6$): 11.51 (s, 1H), 8.00-7.90 (m, 2H), 7.84 (d, J=7.5 Hz, 1H), 7.75-7.55 (m, 2H), 7.47 (t, J=7.8 Hz, 1H), 7.30-7.15 (m, 2H), 5.14 (s, 2H), 3.83 (s, 3H). MS: m/z 311.2 [M+H]$^+$.

b) 3-(3-Carboxybenzyl)quinazoline-2,4(1H,3H)-dione: The title compound was prepared from 3-(3-methoxycarbonylbenzyl)quinazoline-2,4(1H,3H)-dione using a procedure similar to those described for the synthesis of compound of Example 2. MS: m/z 297.2 [M+H]$^+$.

c) 3-(3-(4-(Pyrimidin-2-yl)piperazine-1-carbonyl)benzyl) quinazoline-2,4(1H,3H)-dione: The title compound was prepared from 3-(3-carboxybenzyl)quinazoline-2,4(1H,3H)-dione and 2-(piperazin-1-yl)pyrimidine using a procedure similar to those described for the synthesis of compound of Example 3. $^1$H NMR (DMSO-$d_6$): 11.55 (s, 1H), 8.36 (d, J=4.8 Hz, 2H), 7.93 (d, J=6.9 Hz, 1H), 7.66 (t, J=7.1 Hz, 1H), 7.45-7.26 (m, 4H), 7.25-7.12 (m, 2H), 6.65 (t, J=4.7 Hz, 1H), 5.11 (s, 2H), 3.90-3.20 (m, 8H). MS: m/z 443.3 [M+H]$^+$.

Example 229

1-(3-(4-(Pyrimidin-2-yl)piperazine-1-carbonyl)benzyl)quinazoline-2,4(1H,3H)-dione The compound was prepared from 1-(3-carboxyphenethyl)quinazoline-2,4(1H,3H)-dione (prepared from quinazoline-2,4(1H,3H)-dione and methyl 3-(2-bromoethyl)benzoate using a procedure similar to those used for Examples 1 and 2) and 2-(piperazin-1-yl)pyrimidine using a procedure similar to those described for the synthesis of compound of Example 3. $^1$H NMR (DMSO-$d_6$): 11.54 (s, 1H), 8.37 (d, J=4.8 Hz, 2H), 7.78 (dd, J=7.8 and 1.5 Hz, 1H), 7.73 (t, J=6.9 Hz, 1H), 7.52 (d, J=7.2 Hz, 1H), 7.35-7.22 (m, 5H), 6.66 (t, J=4.7 Hz, 1H), 4.28 (t, J=7.5 Hz, 2H), 3.80-3.20 (m, 8H), 2.95 (t, J=7.4 Hz, 1H). MS: m/z 457.4 [M+H]$^+$.

Example 230

8-Hydroxy-1-(3-(4-(pyrimidin-2-yl)piperazine-1-carbonyl)benzyl)quinazoline-2,4(1H,3H)-dione A solution of BBr$_3$ (4N in DCM, 10 mL, 40 mmol) was added dropwise to a mixture of 8-methoxy-1-(3-(4-(pyrimidin-2-yl)piperazine-1-carbonyl)benzyl)quinazoline-2,4(1H,3H)-dione (60 mg, 0.13 mmol) in DCM (25 mL) at −70° C. The mixture was warmed to room temperature and stirred at r.t overnight. After cooled at ice-bath, 10 mL MeOH was added dropwise and then NH$_4$Cl (a.q.) was added. The mixture was extracted by DCM (50 mL×2), the combined organic layer was dried to give crude product which was purified by TLC (DCM/MeOH=20:1) to give the target product (7.64 mg, 13.1% yield). $^1$H NMR (DMSO-$d_6$): 11.64 (s, 1H), 10.34 (s, 1H), 8.36 (d, J=4.8 Hz, 2H), 7.51 (dd, J=6.8 and 2.6 Hz, 1H), 7.39-7.34 (m, 1H), 7.27-7.23 (m, 3H), 7.10-7.03 (m, 2H), 6.65 (t, J=4.7 Hz, 1H), 5.63 (s, 2H), 3.85-3.53 (m, 8H). MS: m/z 459.4 [M+H]$^+$.

Example 231

Evaluation of the Synergistic Potentiation Effects of 1-(3-(4-(pyrimidin-2-yl)piperazine-1-carbonyl)benzyl)quinazoline-2,4(1H,3H)-dione and Analogs on the Growth Inhibiting Activity of MMS Using a MTT Based Cell Viability Assay The synergistic potentiation effect of PARP inhibitors on the growth inhibiting activity of DNA damaging anticancer drugs such as methyl methanesulphonate (MMS) were measured with SW620 human colorectal cancer cells using a MTT based cell viability assay. Briefly, SW620 human colorectal cancer cells were used to measure the cell growth inhibiting activity of DNA alkylating anticancer drug MMS. The MMS concentration used in the assay was carefully titrated to a level at which NMS only had a minimal inhibitory effect on the cell growth, and under this conditions it was sensitive to detect the potentiation effect of 1-(arylmethyl)quinazoline-2,4(1H,3H)-diones on MMS's inhibiting activity on cell growth. SW620 cells were grown and maintained in RPMI1640 (Gibco) medium supplemented with 10% FBS (Hyclone). In the first day of experiment, 4000 cells were seeded to each well of a 96-well cell culture plate and incubated at 37° C. and 5% $CO_2$ in a cell culture incubator overnight. In the next day, the cell culture medium was removed. One hundred and eighty μl fresh medium containing 1.5 μg/ml MMS and 20 μl of 10-fold concentration of testing compounds or reference compounds (AZD2281 and ABT-888) were added to each well sequentially. The serial dilutions of the reference compounds and the compounds to be tested were made with a 1:3 and 1:10 fashion in DMSO. The 10-fold concentrated solutions of these compounds were made by mixing 10 μl of the serial dilutions in DMSO with 90 μl fresh medium. The final concentration of DMSO in the medium was 1%. The cells were incubated at 37° C. in 5% $CO_2$ cell culture incubator for additional 5 days (120 hours). Afterwards, the 96-well cell culture plate was taken out and 20 μl of MTT solution was added to each well and incubated at 37° C. for 4 h. The medium was removed and 100 μl DMSO was added to each well. The 96-well cell culture plates were shaked adequately for 10 min and readed in a Varioskan Flash plate reader (Thermo Fisher Scientific) at 520 and 690 nm. The data were analyzed by Prism 5 software (GraphPad). The obtained 520 nm absorbance readings substracting corresponding 690 nm reading were analyzed and plotted against the Log scale of the compound concentrations. The curves were fitted using the following equation to calculate the $IC_{50}$ value of each compound, Y(absorbance)=minimal absorbance value+(maximal absorbance value−minimal absorbance value)/(1+10^(Log C−Log $IC_{50}$), C was the compound concentration.

The calculated $IC_{50}$ values are listed in Table 1. These values reflect the potentiation effect of 1-(arylmethyl)quinazoline-2,4(1H,3H)-diones on the growth inhibiting activity of a fixed concentration of MMS in a MTT based cell viability assays.

TABLE 1

Substituted 1-(arylmethyl)quinazoline-2,4(1H,3H)-diones potentiate the growth inhibiting activity of MMS ($IC_{50}$)

| Example # | 1 | 2 | 3 | 4 | 5 | 6 | 7 | 8 |
|---|---|---|---|---|---|---|---|---|
| $IC_{50}$ (nM) | >10000 | >10000 | 90 | 12 | 5356 | 7026 | 5269 | 112 |
| Example # | 9 | 10 | 11 | 12 | 13 | 14 | 15 | 16 |
| $IC_{50}$ (nM) | 500 | 439 | 618 | 533 | 727 | 102 | 666 | 7259 |
| Example # | 17 | 18 | 19 | 20 | 21 | 22 | 23 | 24 |
| $IC_{50}$ (nM) | >10000 | >10000 | >10000 | 391 | >10000 | >10000 | 8.2 | 26 |
| Example # | 25 | 26 | 27 | 28 | 29 | 30 | 31 | 32 |
| $IC_{50}$ (nM) | 9.8 | 149 | 83 | >10000 | >10000 | 119 | 2595 | 106 |
| Example # | 33 | 34 | 35 | 36 | 37 | 38 | 39 | 40 |
| $IC_{50}$ (nM) | 130 | 294 | 265 | >10000 | >10000 | >10000 | 604 | 182 |
| Example # | 41 | 42 | 43 | 44 | 45 | 46 | 47 | 48 |
| $IC_{50}$ (nM) | 11 | 78 | 51 | 6.8 | 34 | 21 | 54 | 56 |
| Example # | 49 | 50 | 51 | 52 | 53 | 54 | 55 | 56 |
| $IC_{50}$ (nM) | 32 | 37 | 33 | 55 | 59 | 217 | 89 | 30 |
| Example # | 57 | 58 | 59 | 60 | 61 | 62 | 63 | 64 |
| $IC_{50}$ (nM) | 46 | 171 | >10000 | >10000 | 61 | 816 | 50 | 177 |
| Example # | 65 | 66 | 67 | 68 | 69 | 70 | 71 | 72 |
| $IC_{50}$ (nM) | 417 | 991 | 2054 | 673 | 352 | 136 | 70 | 80 |
| Example # | 73 | 74 | 75 | 76 | 77 | 78 | 79 | 80 |
| $IC_{50}$ (nM) | 3379 | >10000 | 2661 | ND | 2964 | 269 | 5543 | >10000 |
| Example # | 81 | 82 | 83 | 84 | 85 | 86 | 87 | 88 |
| $IC_{50}$ (nM) | 99 | 459 | 72 | 52 | 25 | 86 | 35 | 137 |
| Example # | 89 | 90 | 91 | 92 | 93 | 94 | 95 | 96 |
| $IC_{50}$ (nM) | ND | >10000 | >10000 | >10000 | >10000 | >10000 | >10000 | >10000 |
| Example # | 97 | 98 | 99 | 100 | 101 | 102 | 103 | 104 |
| $IC_{50}$ (nM) | >10000 | >10000 | >10000 | 202 | 117 | 87 | 45 | 8.3 |
| Example # | 105 | 106 | 107 | 108 | 109 | 110 | 111 | 112 |
| $IC_{50}$ (nM) | 7.9 | 105 | 6.3 | 78 | 48 | 72 | 27 | 14 |
| Example # | 113 | 114 | 115 | 116 | 117 | 118 | 119 | 120 |
| $IC_{50}$ (nM) | 9.6 | 51 | 19 | 48 | 5.1 | 0.82 | 0.72 | 42 |
| Example # | 121 | 122 | 123 | 124 | 125 | 126 | 127 | 128 |
| $IC_{50}$ (nM) | 4.5 | Td | 15 | 9.9 | 6.7 | 18 | 13 | 37 |
| Example # | 129 | 130 | 131 | 132 | 133 | 134 | 135 | 136 |
| $IC_{50}$ (nM) | 18 | 15 | 17 | 4.1 | 4.1 | 5.8 | 6.8 | 7.1 |
| Example # | 137 | 138 | 139 | 140 | 141 | 142 | 143 | 144 |
| $IC_{50}$ (nM) | 7.0 | 351 | 16 | 37 | 12 | 22 | 15 | 2.8 |
| Example # | 145 | 146 | 147 | 148 | 149 | 150 | 151 | 152 |
| $IC_{50}$ (nM) | 12 | 3.4 | 2.7 | 2.1 | 14 | 25 | 18 | 13 |
| Example # | 153 | 154 | 155 | 156 | 157 | 158 | 159 | 160 |
| $IC_{50}$ (nM) | 9.2 | 7.3 | 23 | 28 | 18 | 7.8 | 648 | 394 |
| Example # | 161 | 162 | 163 | 164 | 165 | 166 | 167 | 168 |
| $IC_{50}$ (nM) | 506 | 1193 | 28 | 6.2 | 49 | 4.0 | 5.2 | 15 |
| Example # | 169 | 170 | 171 | 172 | 173 | 174 | 175 | 176 |
| $IC_{50}$ (nM) | 3.4 | 120 | 70 | 9.5 | 228 | 94 | 16 | 15 |
| Example # | 177 | 178 | 179 | 180 | 181 | 182 | 183 | 184 |
| $IC_{50}$ (nM) | >10000 | 7.9 | 12 | 3.1 | 4.9 | 16 | 13 | 62 |
| Example # | 185 | 186 | 187 | 188 | 189 | 190 | 191 | 192 |
| $IC_{50}$ (nM) | 6.7 | 24 | 27 | 7.8 | 10 | 21 | 192 | 7.2 |
| Example # | 193 | 194 | 195 | 196 | 197 | 198 | 199 | 200 |

TABLE 1-continued

Substituted 1-(arylmethyl)quinazoline-2,4(1H,3H)-diones
potentiate the growth inhibiting activity of MMS ($IC_{50}$)

| $IC_{50}$ (nM) | 4.5 | 18 | 1440 | 985 | >10000 | >10000 | 19 | >10000 |
|---|---|---|---|---|---|---|---|---|
| Example # | 201 | 202 | 203 | 204 | 205 | 206 | 207 | 208 |
| $IC_{50}$ (nM) | >10000 | >10000 | >10000 | >10000 | >10000 | >10000 | >10000 | 37 |
| Example # | 209 | 210 | 211 | 212 | 213 | 214 | 215 | 216 |
| $IC_{50}$ (nM) | 103 | 10 | 145 | 19 | 58 | 517 | 1388 | >10000 |
| Example # | 217 | 218 | 219 | 220 | 221 | 223 | 224 | 225 |
| $IC_{50}$ (nM) | 2.5 | 103 | 481 | >10000 | >10000 | >10000 | 1113 | >10000 |
| Example # | 226 | 227 | 228 | 229 | 230 | AZD2281 | ABT-888 | |
| $IC_{50}$ (nM) | 84 | 13 | >10000 | >10000 | 2.6 | 28 | 2642 | |

ND, not determined.

In summary, 1-(3-(4-(pyrimidin-2-yl)piperazine-1-carbonyl)benzyl)quinazoline-2,4(1H,3H)-dione (Example 4) and analogs have excellent potentiation effects on the growth inhibiting activity of DNA damaging anticancer agent MMS in a MTT based cell viability assay.

Example 232

Determination of the Synergistic Potentiation Effect of 1-(3-(4-(pyrimidin-2-yl)piperazine-1-carbonyl) benzyl)quinazoline-2,4(1H,3)-dione and Analogs on MMS Induced Apoptosis Using a Cell Based caspase-3 Activity Assay Human breast cancer cell T47D was used to determine the potentiation effect of PARP inhibitors on the apoptosis inducing activity o DNA damaging anticancer drugs such as MMS. Intracellular caspase-3 activity was used to measure cell apoptosis. The dose response effect of MMS to induce intracellular caspase activity was carefully titrated and the concentration that only induces a minimal level of caspase activity was used to test the potentiation effect of PARP inhibitors. Briefly, T47D cells were grown in DMEM/F12 cell culture medium (Hyclone) supplemented with 0.2 U/ml insulin (Genview) and 10% FBS (Hyclone). A day before experiment, 20000 of T47D cells were seeded to each well of a 96-well cell culture plate and maintained at 37° C. and 5% $CO_2$ in a cell culture incubator overnight. On the day of experiment, cell culture medium was removed. One hundred and eighty μl of fresh medium containing 100 nM MMS was added to each well and followed by 20 μl medium containing 10 folds of the concentrations of experimental drugs or reference compounds (ADZ2281 and ABT-888). The serial dilutions of the compounds to be tested and the reference compounds were made in a 1:3 and 1:10 fashion in DMSO. The 10-fold compound solutions were made by mixing 10 μl DMSO serial dilution solutions with 90 μl fresh growth medium. Twenty four hours later, the cells in the 96-well plates were centrifuged at 1000 g for 5 min and the supernatants were removed. Fifty μl lysis buffer (100 mM Tris, pH 7.5, 0.1M NaCl, 1 mM EDTA, 0.01% Triton X-100) was added to each well and the plates were shaked horizontally for 30 min at 4° C. After centrifugation at 1000 g at 4° C. for 10 min, 20 μl of supernatant was transferred from each well to a corresponding well in a 384-well black plate. Twenty μl of buffer (20 mM PIPES, pH 7.4, 4 mM EDTA and 0.2% CHAPS) containing 20 μM fluorescent caspase-3 substrate ((Ac-DEVD)$_2$-R110, AnaSpec Cat #60304-5) was added to each well afterwards. The plates were shaked to uniformly mix the wells and incubated at 37° C. for 3 h. The fluorescence intensity was measured using the following wavelength: ex: 496 nm, em: 520 nm using a fluorescence plate reader (Varioskan Flash, Thermo Fisher Scientific). The caspase-3 activity induced by the compounds was expressed as a relative fluorescence unit (RFU). The obtained fluorescence readings were analyzed using a commercial graphic software (GraphPad Prism 5) and plotted against the Log value of the compound concentrations. The $EC_{50}$ values were obtained by fitting the data points with the equation of Y(fluorescence reading)=minimal fluorescence reading+(maximal fluorescence reading−minimal fluorescence reading)/(1+10^(Log EC50−Log C)), where C is the concentration of the testing compound.

The synergistic potentiation effect of compounds on MMS induced apoptosis in T470 cells is expressed as $EC_{50}$ values and listed in Table 2.

TABLE 2

Substituted 1-(arylmethyl)quinazoline-2,4(1H,3H)-diones
potentiate the apoptosis inducing activity of MMS ($EC_{50}$)

| Example # | 1 | 2 | 3 | 4 | 5 | 6 | 7 | 8 |
|---|---|---|---|---|---|---|---|---|
| $EC_{50}$ (nM) | >10000 | >10000 | 56 | 12 | 450 | 2518 | 2655 | 120 |
| Example # | 9 | 10 | 11 | 12 | 13 | 14 | 15 | 16 |
| $EC_{50}$ (nM) | 426 | 400 | 214 | 318 | 6601 | 39 | 803 | 9206 |
| Example # | 17 | 18 | 19 | 20 | 21 | 22 | 23 | 24 |
| $EC_{50}$ (nM) | 5018 | >10000 | >10000 | 139 | 5797 | >10000 | 4.0 | 20 |
| Example # | 25 | 26 | 27 | 28 | 29 | 30 | 31 | 32 |
| $EC_{50}$ (nM) | 3.9 | 20 | 51 | 5894 | >10000 | 39 | 112 | 96 |
| Example # | 33 | 34 | 35 | 36 | 37 | 38 | 39 | 40 |
| $EC_{50}$ (nM) | 96 | 104 | 238 | >10000 | 1914 | 267 | 614 | 29 |
| Example # | 41 | 42 | 43 | 44 | 45 | 46 | 47 | 48 |
| $EC_{50}$ (nM) | 2.2 | 11 | 18 | 5.7 | 11 | 6.6 | 2.6 | 8.2 |
| Example # | 49 | 50 | 51 | 52 | 53 | 54 | 55 | 56 |
| $EC_{50}$ (nM) | 10 | 13 | 20 | 22 | 18 | 124 | 20 | 16 |
| Example # | 57 | 58 | 59 | 60 | 61 | 62 | 63 | 64 |
| $EC_{50}$ (nM) | 22 | 108 | >10000 | >10000 | 17 | 379 | 15 | 51 |

TABLE 2-continued

Substituted 1-(arylmethyl)quinazoline-2,4(1H,3H)-diones
potentiate the apoptosis inducing activity of MMS ($EC_{50}$)

| Example # | 65 | 66 | 67 | 68 | 69 | 70 | 71 | 72 |
|---|---|---|---|---|---|---|---|---|
| $EC_{50}$ (nM) | 373 | 604 | 4820 | 635 | 76 | 34 | 67 | 41 |
| Example # | 73 | 74 | 75 | 76 | 77 | 78 | 79 | 80 |
| $EC_{50}$ (nM) | 811 | 2111 | 2869 | ND | 5206 | 112 | 3219 | 1192 |
| Example # | 81 | 82 | 83 | 84 | 85 | 86 | 87 | 88 |
| $EC_{50}$ (nM) | 63 | 154 | 21 | 18 | 7.6 | 27 | 27 | 67 |
| Example # | 89 | 90 | 91 | 92 | 93 | 94 | 95 | 96 |
| $EC_{50}$ (nM) | ND | 4168 | 1987 | 2926 | >10000 | >10000 | >10000 | >10000 |
| Example # | 97 | 98 | 99 | 100 | 101 | 102 | 103 | 104 |
| $EC_{50}$ (nM) | >10000 | >10000 | >10000 | 70 | 20 | 26 | 29 | 2.6 |
| Example # | 105 | 106 | 107 | 108 | 109 | 110 | 111 | 112 |
| $EC_{50}$ (nM) | 14 | 217 | 9.5 | 68 | 23 | 32 | 1.7 | 2.9 |
| Example # | 113 | 114 | 115 | 116 | 117 | 118 | 119 | 120 |
| $EC_{50}$ (nM) | 17 | 19 | 23 | 13 | 5.8 | 3.1 | 3.0 | 8.8 |
| Example # | 121 | 122 | 123 | 124 | 125 | 126 | 127 | 128 |
| $EC_{50}$ (nM) | 4.9 | 8.4 | 11 | 3.8 | 22 | 6.5 | 4.1 | 12 |
| Example # | 129 | 130 | 131 | 132 | 133 | 134 | 135 | 136 |
| $EC_{50}$ (nM) | 49 | 87 | 20 | 0.93 | 2.1 | 4.7 | 9.8 | 3.2 |
| Example # | 137 | 138 | 139 | 140 | 141 | 142 | 143 | 144 |
| $EC_{50}$ (nM) | 2.1 | 281 | 4.0 | 8.9 | 13 | 3.8 | 6.0 | 3.4 |
| Example # | 145 | 146 | 147 | 148 | 149 | 150 | 151 | 152 |
| $EC_{50}$ (nM) | 6.5 | 4.1 | 3.4 | 2.3 | 5.8 | 16 | 5.2 | 5.1 |
| Example # | 153 | 154 | 155 | 156 | 157 | 158 | 159 | 160 |
| $EC_{50}$ (nM) | 2.0 | 6.7 | 12 | 14 | 26 | 8.6 | 220 | 261 |
| Example # | 161 | 162 | 163 | 164 | 165 | 166 | 167 | 168 |
| $EC_{50}$ (nM) | 405 | 495 | 42 | 2.1 | 18 | 1.6 | 5.0 | 3.8 |
| Example # | 169 | 170 | 171 | 172 | 173 | 174 | 175 | 176 |
| $EC_{50}$ (nM) | 1.0 | 43 | 23 | 3.2 | 122 | 37 | 14 | 10 |
| Example # | 177 | 178 | 179 | 180 | 181 | 182 | 183 | 184 |
| $EC_{50}$ (nM) | 743 | 11 | 7.4 | 1.4 | 2.4 | 14 | 6.1 | 18 |
| Example # | 185 | 186 | 187 | 188 | 189 | 190 | 191 | 192 |
| $EC_{50}$ (nM) | 2.1 | 6.8 | 30 | ND | ND | ND | ND | 3.1 |
| Example # | 193 | 194 | 195 | 196 | 197 | 198 | 199 | 200 |
| $EC_{50}$ (nM) | 1.6 | 11 | 471 | >10000 | >10000 | >10000 | 4.9 | >10000 |
| Example # | 201 | 202 | 203 | 204 | 205 | 206 | 207 | 208 |
| $EC_{50}$ (nM) | >10000 | >10000 | >10000 | >10000 | >10000 | >10000 | >10000 | 24 |
| Example # | 209 | 210 | 211 | 212 | 213 | 214 | 215 | 216 |
| $EC_{50}$ (nM) | 294 | 15 | 166 | 45 | 590 | 654 | 743 | >10000 |
| Example # | 217 | 218 | 219 | 220 | 221 | 223 | 224 | 225 |
| $EC_{50}$ (nM) | 19 | 37 | 445 | >10000 | >10000 | >10000 | 274 | >10000 |
| Example # | 226 | 227 | 228 | 229 | 230 | AZD2281 | ABT-888 | |
| $EC_{50}$ (nM) | 24 | 40 | >10000 | >10000 | 3.2 | 24 | 3494 | |

ND, not determined.

In summary, as measured by the intracellular caspase activity, 1-(3-(4-(pyrimidin-2-yl)piperazine-1-carbonyl)benzyl)quinazoline-2,4(1H,3H)-dione (Example 4) and its analogs have shown potentiation effect on DNA damaging anticancer drug MMS induced cancer apoptosis.

Example 233

Determination of the Cell Growth Inhibiting Activity of 1-(3-(4-(pyrimidin-2-yl)piperazine-1-carbonyl)benzyl)quinazoline-2,4(1H,3H)-dione and Analogs BRCA-2 Deficient CAPAN-1 Pancreatic Duck Cancer Cells Using a MTT Based Cell Viability Assay BRCA-deficient cancer cells are sensitive to PARP inhibition. In the presence of PARP inhibitors, BRCA-deficient cancer cells could not grow and eventually will lead to death of cells. BRCA-2 deficient CAPAN-1 human pancreatic cancer cells were used to test the growth inhibiting activity of substituted 1-(arylmethyl)quinazoline-2,4(1H,3,H)-diones. Briefly, CAPAN-1 cells are grown and maintained in IMEM medium supplemented with 2.0% FBS. The assay takes 10 days to finish. On day 1, 6000 CAPAN-1 cells are seeded to each well of a 96-well plate. The cells are incubated at 37° C. in a cell culture incubator overnight. In the next day, serial dilutions of compounds to be tested and reference compound (AZD2281) were prepared with a 1:3 and 1:10 fashion in DMSO. Ten-fold compound solutions were made by mixing 10 μl DMSO serial dilution solutions with 90 μl fresh growth medium. The cell culture medium was removed and 180 μl fresh media with FBS and 20 μl of compound solutions were added to each well. The final concentration of DMSO was 1%. Cells were then returned to the $CO_2$ cell culture incubator and incubated at 37° C. for two days (day 3 and day 4). On day 5, the same procedure as what was done on day 2 was repeated. Cell culture medium was removed and fresh medium containing serial dilutions of compounds or reference compounds were added. Cells were returned to the $CO_2$ cell culture incubator and incubated for two more days. On day 8, same procedure was repeated again and fresh medium containing the testing compounds or reference compounds were added and incubated for an additional 2 days. On day 10, 20 µl of MTT reagent (5 mg/ml) was added to each well of the cell culture plate and incubated for 4 h. The cell culture media was removed and 100 µl DMSO was added to each well. The 96-well cell culture plates were shaked horizontally for 10 min and readed in a Varioskan Flash plate reader (Thermo Fisher Scientific) at 520 and 690 nm. The obtained 520 nm absorbance readings substracting corresponding 690 nm reading were analyzed using a commercial graphic software (GraphPad Prism 5) and plotted against the Log scale of the compound concentrations. The curves were fitted using the following equation to calculate the $IC_{50}$ value of each compound, Y(520 nm−690 nm)=minimal absorbance value+(maximal absorbance value−minimal absorbance value)/(1+10^(Log C−Log $IC_{50}$)), where C was the concentration of testing compounds.

The inhibitor effect of compounds on the CAPAN-1 cell growth is expressed as $IC_{50}$ values and listed in Table 3.

TABLE 3

Growth inhibition of CAPAN-1 cells by selected substituted 1-(arylmethyl)quinazoline-2,4(1H,3H)-diones ($IC_{50}$)

| Example # | 3 | 4 | 8 | 11 | 15 | 20 | 23 | 24 |
|---|---|---|---|---|---|---|---|---|
| $IC_{50}$ (nM) | 445 | 55 | 2360 | 1841 | >10000 | 4942 | 160 | 735 |
| Example # | 25 | 26 | 27 | 30 | 40 | 41 | 42 | 43 |
| $IC_{50}$ (nM) | 98 | 400 | 281 | 1785 | 1739 | 208 | 2539 | 974 |
| Example # | 44 | 45 | 46 | 48 | 49 | 50 | 51 | 56 |
| $IC_{50}$ (nM) | 318 | 668 | 446 | 168 | 421 | 173 | 402 | 1181 |
| Example # | 65 | 69 | 70 | 81 | 83 | 85 | 100 | 101 |
| $IC_{50}$ (nM) | 3189 | 1982 | 339 | 421 | 746 | 291 | 312 | 1049 |
| Example # | 103 | 104 | 105 | 107 | 111 | 112 | 113 | 117 |
| $IC_{50}$ (nM) | 665 | 452 | 97 | 161 | 77 | 767 | 170 | 39 |
| Example # | 118 | 119 | 123 | 124 | 127 | 128 | 132 | 133 |
| $IC_{50}$ (nM) | 54 | 56 | 111 | 137 | 44 | 442 | 17 | 22 |
| Example # | 134 | 136 | 139 | 140 | 142 | 143 | 144 | 145 |
| $IC_{50}$ (nM) | 45 | 40 | 36 | 155 | 223 | 73 | 78 | 146 |
| Example # | 147 | 149 | 150 | 152 | 154 | 155 | 157 | 161 |
| $IC_{50}$ (nM) | 47 | 52 | 176 | 121 | 56 | 142 | 202 | 3547 |
| Example # | 168 | 172 | 176 | 185 | 186 | 188 | 189 | 190 |
| $IC_{50}$ (nM) | 1465 | 389 | 187 | 358 | 167 | 472 | 736 | 1383 |
| Example # | 199 | 210 | 212 | 217 | AZD2281 | | | |
| $IC_{50}$ (nM) | 25 | 948 | 3445 | >10000 | 460 | | | |

In summary, 1-(3-(4-(pyrimidin-2-yl)piperazine-1-carbonyl)benzyl)quinazoline-2,4(1H,3H)-dione (Example 4) and analogs are excellent inhibitors of CAPAN-1 cell growth, suggesting that they are good PARP inhibitors.

Example 234

Measurement of the Inhibitory Effect of 1-(3-(4-(pyrimidin-2-yl)piperazine-1-carbonyl)benzyl)quinazoline-2,4(1H,3H)-dione and Analogs on PARP-1 Enzymtic Activity The measurement of PARP-1 enzymtic activity was achieved by using a commercial 96-well colorimetric assay kit (4676-096-K, Trevigen, Inc. Gaithersburg, Md. 20877 USA). Briefly, PARP-1 catalyzes the NAD-dependent addition of poly(ADP-ribose) to its nuclear protein substrates such as histones. The assay kit measures the incorporation of biotynylated poly(ADP-ribose) onto histone proteins in a 96-well format.

Reference compound (AZD2281) and compounds to be tested are serially diluted 1:10 with a 1× buffer. To each well of histone pre-coated plate 10 µl of 5-fold concentrations of testing compounds or reference compound, 15 µl of PARP-1 enzyme (0.5 unit) and 25 µl reaction buffer were added and the plates were incubated at room temperature for 60 min. The plates were washed with 200 µl PBS with 0.1% Triton X-100 twice and then with 200 µl PBS twice. The residual liquid was removed by carefully tapping the plates on paper towels. Equal volumes of PeroxyGlow™ solution A and B were mixed and 100 µl of the solution was added to each well. The luminescence readings were read immediately in a Varioskan Flash plate reader (Thermo Fisher Scientific). The obtained luminescence readings were analyzed using a commercial graphic software (GraphPad Prism 5) and plotted against the Log scale of the compound concentrations. The $IC_{50}$ values were obtained by fitting the data points with the equation of Y(Luminescence reading)=minimal luminescence reading+(maximal luminescence reading−minimal luminescence reading)/(1+10^(Log C−Log $EC_{50}$)), where C is the concentration of the testing compound.

TABLE 4

The inhibitory effect of substituted 1-(arylmethyl)quinazoline-2,4(1H,3H)-diones on PARP-1 enzymatic activity ($IC_{50}$)

| Example # | 3 | 4 | 8 | 14 | 25 | 44 | 127 | 132 | 135 | 139 |
|---|---|---|---|---|---|---|---|---|---|---|
| $IC_{50}$ (nM) | 4.2 | 0.96 | 5.3 | 2.3 | 0.21 | 0.88 | 0.37 | 1.19 | 1.74 | 1.3 |
| Example # | 144 | 147 | 189 | AZD2281 | | | | | | |
| $IC_{50}$ (nM) | 1.15 | 1.2 | 2.20 | 2.2 | | | | | | |

In summary, as measured in the PARP-1 enzymatic assay, 1-(3-(4-(pyrimidin-2-yl)piperazine-1-carbonyl)benzyl)quinazoline-2,4(1H,3H)-dione (Example 4) and analogs are potent PARP-1 inhibitors.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A pharmaceutical composition comprising:
   (a) a compound having a structure represented by the following Formula I, or a pharmaceutically acceptable salt thereof,

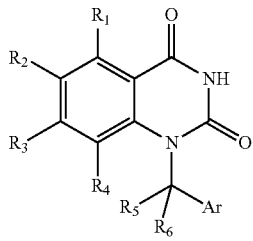

(I)

wherein:
   Ar is phenyl, pyridyl or furanyl having a substituted carbonyl at the meta-position;
   $R_1$ is halo, $NH_2$, $C_{1-6}$ alkyl, nitro, or hydroxyl; $R_2$-$R_4$ independently are H, halo, $NH_2$, $C_{1-6}$ alkyl, nitro or hydroxyl; or
   $R_2$ is halo, $NH_2$, $C_{1-6}$ alkyl, nitro, or hydroxyl; $R_1$, $R_3$ and $R_4$ independently are H, halo, $NH_2$, $C_{1-6}$ alkyl, nitro or hydroxyl; or
   $R_3$ is halo, $NH_2$, $C_{1-6}$ alkyl, nitro, or hydroxyl; $R_1$, $R_2$ and $R_4$ independently are H, halo, $NH_2$, $C_{1-6}$ alkyl, nitro or hydroxyl; or
   $R_4$ is halo, $NH_2$, $C_{1-6}$ alkyl, nitro, or hydroxyl; $R_1$-$R_3$ independently are H, halo, $NH_2$, $C_{1-6}$ alkyl, nitro or hydroxyl;
   $R_5$ is H;
   $R_6$ is H; and
   wherein the substituted carbonyl is a carbonyl substituted by piperazinyl or piperidyl optionally substituted by one substituent selected from the group consisting of: pyridyl; pyrimidinyl; $C_{3-8}$ cycloalkyl; $C_{1-6}$ alkyl optionally substituted by one $C_{3-8}$ cycloalkyl; benzoyl optionally substituted by one or more substituents selected from the group consisting of halo and $C_{1-6}$ alkoxyl; carbonyl optionally substituted by one substituent selected from the group consisting of $C_{3-8}$ cycloalkyl, thienyl, pyridyl, furanyl and tetrahydrofuranyl; $C_{1-6}$ alkyl sulfonyl; phenyl; pyrazinyl; benzo[d]isothiazol-3-yl; benzoisoxazolyl optionally substituted by one or more halo; thiazoyl; piperidyl; and phenoxyl; and
   (b) a pharmaceutically acceptable carrier.

2. The pharmaceutical composition of claim 1, wherein the compound has a structure represented by the following Formula II:

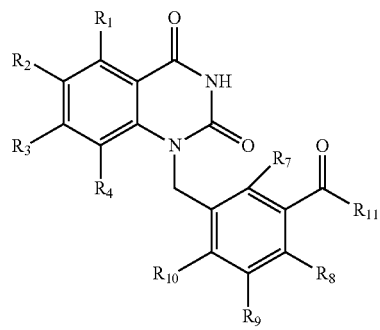

(II)

wherein:
   $R_1$ is halo, $NH_2$, $C_{1-6}$ alkyl, nitro, or hydroxyl; $R_2$-$R_4$ independently are H, halo, $NH_2$, $C_{1-6}$ alkyl, nitro or hydroxyl; or
   $R_2$ is halo, $NH_2$, $C_{1-6}$ alkyl, nitro, or hydroxyl; $R_1$, $R_3$ and $R_4$ independently are H, halo, $NH_2$, $C_{1-6}$ alkyl, nitro or hydroxyl; or
   $R_3$ is halo, $NH_2$, $C_{1-6}$ alkyl, nitro, or hydroxyl; $R_1$, $R_2$ and $R_4$ independently are H, halo, $NH_2$, $C_{1-6}$ alkyl, nitro or hydroxyl; or
   $R_4$ is halo, $NH_2$, $C_{1-6}$ alkyl, nitro, or hydroxyl; $R_1$-$R_3$ independently are H, halo, $NH_2$, $C_{1-6}$ alkyl, nitro or hydroxyl;
   $R_7$-$R_{10}$ independently are selected from the group consisting of H, halo, $NH_2$, $C_{1-6}$ alkoxyl, $C_{1-6}$ alkyl, halo $C_{1-6}$ alkyl, and nitro; and
   $R_{11}$ is piperazinyl or piperidyl, optionally substituted by one substituent selected from the group consisting of: pyridyl; pyrimidinyl; $C_{3-8}$ cycloalkyl; $C_{1-6}$ alkyl optionally substituted by one $C_{3-8}$ cycloalkyl; benzoyl optionally substituted by one or more substituents selected from the group consisting of halo and $C_{1-6}$ alkoxyl; carbonyl optionally substituted by one substituent selected from the group consisting of $C_{3-8}$ cycloalkyl, thienyl, pyridyl, furanyl and tetrahydrofuranyl; $C_{1-6}$ alkylsulfonyl; phenyl; pyrazinyl; benzo[d]isothiazol-3-yl; benzoisoxazolyl optionally substituted by one or more halo; thiazoyl; piperidyl; and phenoxyl.

3. The pharmaceutical composition of claim 1, wherein the compound has a structure represented by the following Formula III:

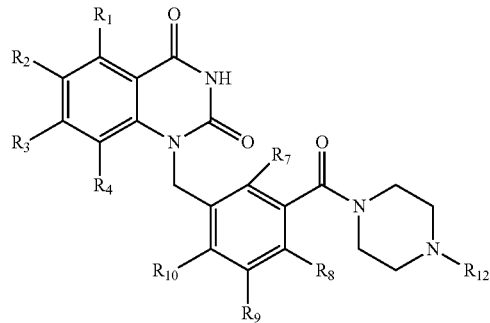

(III)

wherein:
   $R_1$ is halo, $NH_2$, $C_{1-6}$ alkyl, nitro, or hydroxyl; $R_2$-$R_4$ independently are H, halo, $NH_2$, $C_{1-6}$ alkyl, nitro or hydroxyl; or $R_2$ is halo, $NH_2$, $C_{1-6}$ alkyl, nitro, or hydroxyl; $R_1$, $R_3$ and $R_4$ independently are H, halo, $NH_2$, $C_{1-6}$ alkyl, nitro or hydroxyl; or $R_3$ is halo, $NH_2$, $C_{1-6}$ alkyl, nitro, or hydroxyl; $R_1$, $R_2$ and $R_4$ independently are H, halo, $NH_2$, $C_{1-6}$ alkyl, nitro or hydroxyl; or $R_4$ is halo, $NH_2$, $C_{1-6}$ alkyl, nitro, or hydroxyl; $R_1$-$R_3$ independently are H, halo, $NH_2$, $C_{1-6}$ alkyl, nitro or hydroxyl;

$R_7$-$R_{10}$ independently are selected from the group consisting of H, halo, $C_{1-6}$ alkoxyl and nitro; and $R_{12}$ is pyridyl; pyrimidinyl; $C_{3-8}$ cycloalkyl; $C_{1-6}$ alkyl optionally substituted by one $C_{3-8}$ cycloalkyl; benzoyl optionally substituted by one or more substituents selected from the group consisting of halo and $C_{1-6}$ alkoxyl; carbonyl optionally substituted by one substituent selected from the group consisting of $C_{3-8}$ cycloalkyl, thienyl, pyridyl, furanyl and tetrahydrofuranyl; $C_{1-6}$ alkyl sulfonyl; phenyl; pyrazinyl; benzo[d]isothiazol-3-yl;

benzoisoxazolyl optionally substituted by one or more halo; and thiazoyl.

4. The pharmaceutical composition of claim 3, wherein $R_1$ is fluoro, chloro, bromo or methyl;

$R_2$ is H, fluoro, chloro, bromo or methyl;

$R_3$ is H, fluoro, chloro or methyl;

$R_4$ is H, fluoro, chloro, methyl, or hydroxy; and

Each of $R_7$, $R_8$, $R_9$, or $R_{10}$ is H or fluoro.

5. The pharmaceutical composition of claim 3, wherein $R_1$ is halo;

$R_2$ is H, halo or $C_1$-$C_6$ alkyl;

$R_3$ is H, halo or $C_1$-$C_6$ alkyl;

$R_4$ is H, halo or $C_1$-$C_6$ alkyl;

$R_7$-$R_{10}$ independently are selected from the group consisting of H and halo; and $R_{12}$ is pyrimidinyl.

6. The pharmaceutical composition of claim 1, further comprising at least one known anticancer agent, or a pharmaceutically acceptable salt of said agent.

7. The pharmaceutical composition of claim 6, wherein the anticancer agent or pharmaceutically acceptable salt of said agent is selected from the group consisting of busulfan, melphalan, chlorambucil, cyclophosphamide, ifosfamide, temozolomide, bendamustine, cis-platin, mitomycin C, bleomycin, carboplatin, camptothecin, irinotecan, topotecan, doxorubicin, epirubicin, aclarubicin, mitoxantrone, elliptinium, etoposide, 5-azacytidine, gemcitabine, 5-fluorouracil, methotrexate, 5-fluoro-2'-deoxy-uridine, fludarabine, nelarabine, ara-C, alanosine, pralatrexate, pemetrexed, hydroxyurea, thioguanine, colchicine, vinblastine, vincristine, vinorelbine, paclitaxel, ixabepilone, cabazitaxel, docetaxel, campath, Panitumumab, Ofatumumab, Avastin, trastuzumab, Rituximab, imatinib, gefitinib, erlotinib, lapatinib, sorafenib, sunitinib, nilotinib, dasatinib, pazopanib, temsirolimus, everolimus, vorinostat, romidepsin, tamoxifen, letrozole, fulvestrant, mitoguazone, octreotide, retinoic acid, arsenic trioxide, zoledronic acid, bortezomib, thalidomide and lenalidomide.

8. The pharmaceutical composition of claim 7, wherein the compound has a structure represented by the following Formula III:

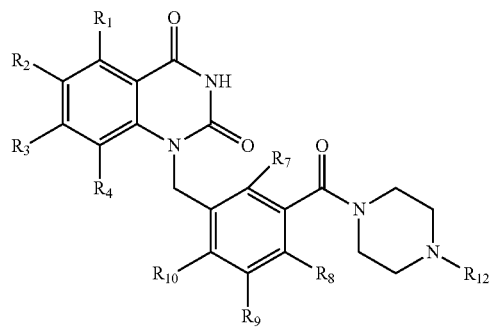

(III)

wherein:

$R_1$ is halo, $NH_2$, $C_{1-6}$ alkyl, nitro, or hydroxyl; $R_2$-$R_4$ independently are H, halo, $NH_2$, $C_{1-6}$ alkyl, nitro or hydroxyl; or $R_2$ is halo, $NH_2$, $C_{1-6}$ alkyl, nitro, or hydroxyl; $R_1$, $R_3$ and $R_4$ independently are H, halo, $NH_2$, $C_{1-6}$ alkyl, nitro or hydroxyl; or $R_3$ is halo, $NH_2$, $C_{1-6}$ alkyl, nitro, or hydroxyl; $R_1$, $R_2$ and $R_4$ independently are H, halo, $NH_2$, $C_{1-6}$ alkyl, nitro or hydroxyl; or $R_4$ is halo, $NH_2$, $C_{1-6}$ alkyl, nitro, or hydroxyl; $R_1$-$R_3$ independently are H, halo, $NH_2$, $C_{1-6}$ alkyl, nitro or hydroxyl;

$R_7$-$R_{10}$ independently are selected from the group consisting of H, halo, $C_{1-6}$ alkoxyl and nitro; and $R_{12}$ is pyridyl; pyrimidinyl; $C_{3-8}$ cycloalkyl; $C_{1-6}$ alkyl optionally substituted by one $C_{3-8}$ cycloalkyl; benzoyl optionally substituted by one or more substituents selected from the group consisting of halo and $C_{1-6}$ alkoxyl; carbonyl optionally substituted by one substituent selected from the group consisting of $C_{3-8}$ cycloalkyl, thienyl, pyridyl, furanyl and tetrahydrofuranyl; $C_{1-6}$ alkyl sulfonyl; phenyl; pyrazinyl; benzo[d]isothiazol-3-yl; benzoisoxazolyl optionally substituted by one or more halo; and thiazoyl.

9. The pharmaceutical composition of claim 8, wherein:

$R_1$ is halo;

$R_2$ is H, halo or $C_1$-$C_6$ alkyl;

$R_3$ is H, halo or $C_1$-$C_6$ alkyl;

$R_4$ is H, halo or $C_1$-$C_6$ alkyl;

$R_7$-$R_{10}$ independently are selected from the group consisting of H and halo; and $R_{12}$ is pyrimidinyl.

10. A pharmaceutical composition comprising:

(a) a compound selected from the group consisting of:

1-(3-(4-(Cyclopentylcarbonyl)piperazine-1-carbonyl)benzyl)-7-fluoroquinazoline-2,4(1H,3H)-dione;

7-Fluoro-1-(3-(4-(pyrimidin-2-yl)piperazine-1-carbonyl)benzyl)quinazoline-2,4(1H,3H)-dione;

1-(3-(4-(Cyclopentylcarbonyl)piperazine-1-carbonyl)benzyl)-7-methylquinazoline-2,4(1H,3H)-dione;

7-Methyl-1-(3-(4-(pyrimidin-2-yl)piperazine-1-carbonyl)benzyl)quinazoline-2,4(1H,3H)-dione;

6-Methyl-1-(3-(4-(pyrimidin-2-yl)piperazine-1-carbonyl)benzyl)quinazoline-2,4(1H,3H)-dione;

1-(3-(4-(Cyclopentylcarbonyl)piperazine-1-carbonyl)benzyl)-6-methylquinazoline-2,4(1H,3H)-dione;

1-(4-Fluoro-3-(4-(pyrimidin-2-yl)piperazine-1-carbonyl)benzyl)-6-methylquinazoline-2,4(1H,3H)-dione;

1-(3-(4-(Cyclohexylcarbonyl)piperazine-1-carbonyl)-4-fluorobenzyl)-6-methylquinazoline-2,4(1H,3H)-dione;

1-(3-(4-(Cyclopentylcarbonyl)piperazine-1-carbonyl)-4-fluorobenzyl)-6-methylquinazoline-2,4(1H,3H)-dione;
6-Bromo-1-(3-(4-(cyclohexylcarbonyl)piperazine-1-carbonyl)benzyl)quinazoline-2,4(1H,3H)-dione;
6-Bromo-1-(3-(4-(cyclopentylcarbonyl)piperazine-1-carbonyl)benzyl)quinazoline-2,4(1H,3H)-dione;
6-Bromo-1-(3-(4-(pyrimidin-2-yl)piperazine-1-carbonyl)benzyl)quinazoline-2,4(1H,3H)-dione;
1-(3-(4-(Cyclopentylcarbonyl)piperazine-1-carbonyl)benzyl)-6-nitroquinazoline-2,4(1H,3H)-dione;
6-Nitro-1-(3-(4-(pyrimidin-2-yl)piperazine-1-carbonyl)benzyl)quinazoline-2,4(1H,3H)-dione;
1-(3-(4-(Cyclohexylcarbonyl)piperazine-1-carbonyl)benzyl)-6-nitroquinazoline-2,4(1H,3H)-dione;
5-Chloro-1-(3-(4-(pyrimidin-2-yl)piperazine-1-carbonyl)benzyl)quinazoline-2,4(1H,3H)-dione;
5-Chloro-1-(3-(4-(cyclopentylcarbonyl)piperazine-1-carbonyl)benzyl)quinazoline-2,4(1H,3H)-dione;
5-Chloro-1-(3-(4-(cyclohexylcarbonyl)piperazine-1-carbonyl)benzyl)quinazoline-2,4(1H,3H)-dione;
5-Chloro-1-(4-fluoro-3-(4-(pyrimidin-2-yl)piperazine-1-carbonyl)benzyl)quinazoline-2,4(1H,3H)-dione;
5-Chloro-1-(3-(4-(cyclopentylcarbonyl)piperazine-1-carbonyl)-4-fluorobenzyl)quinazoline-2,4(1H,3H)-dione;
5-Chloro-1-(3-(4-(cyclohexylcarbonyl)piperazine-1-carbonyl)-4-fluorobenzyl)quinazoline-2,4(1H,3H)-dione;
5-Chloro-1-(4-fluoro-3-(4-(pyridin-2-yl)piperazine-1-carbonyl)benzyl)quinazoline-2,4(1H,3H)-dione;
5-Chloro-1-(4-fluoro-3-(4-(thiophene-2-carbonyl)piperazine-1-carbonyl)benzyl)quinazoline-2,4(1H,3H)-dione;
5-Chloro-1-(3-(4-(cyclohexylcarbonyl)piperazine-1-carbonyl)-6-fluorobenzyl)quinazoline-2,4(1H,3H)-dione;
5-Chloro-1-(3-(4-(cyclopentylcarbonyl)piperazine-1-carbonyl)-6-fluorobenzyl)quinazoline-2,4(1H,3H)-dione;
5-Chloro-1-(6-fluoro-3-(4-(pyrimidin-2-yl)piperazine-1-carbonyl)benzyl)quinazoline-2,4(1H,3H)-dione;
6-Chloro-1-(3-(4-(pyrimidin-2-yl)piperazine-1-carbonyl)benzyl)quinazoline-2,4(1H,3H)-dione;
6-Chloro-1-(3-(4-(cyclopentylcarbonyl)piperazine-1-carbonyl)benzyl)quinazoline-2,4(1H,3H)-dione;
6-Chloro-1-(3-(4-(cyclohexylcarbonyl)piperazine-1-carbonyl)benzyl)quinazoline-2,4(1H,3H)-dione;
6-Chloro-1-(3-(4-(pyridin-2-yl)piperazine-1-carbonyl)benzyl)quinazoline-2,4(1H,3H)-dione;
6-Chloro-1-(3-(4-(thiophene-2-carbonyl)piperazine-1-carbonyl)benzyl)quinazoline-2,4(1H,3H)-dione;
6-Chloro-1-(3-(4-(cyclobutylcarbonyl)piperazine-1-carbonyl)benzyl)quinazoline-2,4(1H,3H)-dione;
6-Chloro-1-(4-fluoro-3-(4-(pyrimidin-2-yl)piperazine-1-carbonyl)benzyl)quinazoline-2,4(1H,3H)-dione;
6-Chloro-1-(3-(4-(cyclopentylcarbonyl)piperazine-1-carbonyl)-4-fluorobenzyl)quinazoline-2,4(1H,3H)-dione;
6-Chloro-1-(3-(4-(cyclohexylcarbonyl)piperazine-1-carbonyl)-4-fluorobenzyl)quinazoline-2,4(1H,3H)-dione;
6-Chloro-1-(4-fluoro-3-(4-(pyridin-2-yl)piperazine-1-carbonyl)benzyl)quinazoline-2,4(1H,3H)-dione;
6-Chloro-1-(4-fluoro-3-(4-(thiophene-2-carbonyl)piperazine-1-carbonyl)benzyl)quinazoline-2,4(1H,3H)-dione;
6-Chloro-1-(3-(4-(cyclopropylcarbonyl)piperazine-1-carbonyl)-4-fluorobenzyl)quinazoline)-2,4(1H,3H)-dione;
6-Chloro-1-(6-fluoro-3-(4-(pyrimidin-2-yl)piperazine-1-carbonyl)benzyl)quinazoline-2,4(1H,3H)-dione;
6-Chloro-1-(3-(4-(cyclopentylcarbonyl)piperazine-1-carbonyl)-6-fluorobenzyl)quinazoline-2,4(1H,3H)-dione;
6-Chloro-1-(3-(4-(cyclohexylcarbonyl)piperazine-1-carbonyl)-6-fluorobenzyl)quinazoline-2,4(1H,3H)-dione;
6-Chloro-1-(6-fluoro-3-(4-(thiophene-2-carbonyl)piperazine-1-carbonyl)benzyl)quinazoline-2,4(1H,3H)-dione;
5-Fluoro-1-(3-(4-(pyrimidin-2-yl)piperazine-1-carbonyl)benzyl)quinazoline-2,4(1H,3H)-dione;
1-(3-(4-(Cyclopentylcarbonyl)piperazine-1-carbonyl)benzyl)-5-fluoroquinazoline-2,4(1H,3H)-dione;
1-(3-(4-(Cyclohexylcarbonyl)piperazine-1-carbonyl)benzyl)-5-fluoroquinazoline-2,4(1H,3H)-dione;
5-Fluoro-1-(3-(4-(pyridin-2-yl)piperazine-1-carbonyl)benzyl)quinazoline-2,4(1H,3H)-dione;
5-Fluoro-(1-(3-(4-(thiophene-2-carbonyl)piperazine-1-carbonyl)benzyl)quinazoline)-2,4(1H,3H)-dione;
5-Fluoro-1-(4-fluoro-3-(4-(pyrimidin-2-yl)piperazine-1-carbonyl)benzyl)quinazoline-2,4(1H,3H)-dione;
1-(3-(4-(Cyclopentylcarbonyl)piperazine-1-carbonyl)-4-fluorobenzyl)-5-fluoroquinazoline-2,4(1H,3H)-dione;
1-(3-(4-(Cyclohexylcarbonyl)piperazine-1-carbonyl)-4-fluorobenzyl)-5-fluoroquinazoline-2,4(1H,3H)-dione;
5-Fluoro-1-(4-fluoro-3-(4-(pyridin-2-yl)piperazine-1-carbonyl)benzyl)quinazoline-2,4(1H,3H)-dione;
5-Fluoro-1-(4-fluoro-3-(4-(thiophene-2-carbonyl)piperazine-1-carbonyl)benzyl)quinazoline-2,4(1H,3H)-dione;
1-(3-(4-Benzoylpiperazine-1-carbonyl)-4-fluorobenzyl)-5-fluoroquinazoline-2,4(1H,3H)-dione;
1-(3-(4-(Cyclohexylcarbonyl)piperazine-1-carbonyl)benzyl)-8-fluoroquinazoline-2,4(1H,3H)-dione;
6-Fluoro-1-(3-(4-(pyrimidin-2-yl)piperazine-1-carbonyl)benzyl)quinazoline-2,4(1H,3H)-dione;
6-Fluoro-1-(3-(4-(pyridin-2-yl)piperazine-1-carbonyl)benzyl)quinazoline-2,4(1H,3H)-dione;
6-Fluoro-1-(3-(4-(thiophene-2-carbonyl)piperazine-1-carbonyl)benzyl)quinazoline-2,4(1H,3H)-dione;
1-(3-(4-(Cyclohexylcarbonyl)piperazine-1-carbonyl)benzyl)-6-fluoroquinazoline-2,4(1H,3H)-dione;
1-(3-(4-(Cyclopentylcarbonyl)piperazine-1-carbonyl)benzyl)-6-fluoroquinazoline-2,4(1H,3H)-dione;
6-Fluoro-1-(4-fluoro-3-(4-(pyrimidin-2-yl)piperazine-1-carbonyl)benzyl)quinazoline-2,4(1H,3H)-dione;
6-Fluoro-1-(4-fluoro-3-(4-(pyridin-2-yl)piperazine-1-carbonyl)benzyl)quinazoline-2,4(1H,3H)-dione;
6-Fluoro-1-(4-fluoro-3-(4-(thiophene-2-carbonyl)piperazine-1-carbonyl)benzyl)quinazoline-2,4(1H,3H)-dione;
1-(3-(4-(Cyclohexylcarbonyl)piperazine-1-carbonyl)-4-fluorobenzyl)-6-fluoroquinazoline-2,4(1H,3H)-dione;
1-(3-(4-(Cyclopentylcarbonyl)piperazine-1-carbonyl)-4-fluorobenzyl)-6-fluoroquinazoline-2,4(1H,3H)-dione;
6-Fluoro-1-(6-fluoro-3-(4-(pyrimidin-2-yl)piperazine-1-carbonyl)benzyl)quinazoline-2,4(1H,3H)-dione;

6-Fluoro-1-(6-fluoro-3-(4-(pyridin-2-yl)piperazine-1-carbonyl)benzyl)quinazoline-2,4(1H,3H)-dione;
6-Fluoro-1-(6-fluoro-3-(4-(thiophene-2-carbonyl)piperazine-1-carbonyl)benzyl)quinazoline-2,4(1H,3H)-dione;
1-(3-(4-(Cyclohexylcarbonyl)piperazine-1-carbonyl)-6-fluorobenzyl)-6-fluoroquinazoline-2,4(1H,3H)-dione;
1-(3-(4-(Cyclopentylcarbonyl)piperazine-1-carbonyl)-6-fluorobenzyl)-6-fluoroquinazoline-2,4(1H,3H)-dione;
5-Fluoro-1-(6-fluoro-3-(4-(pyrimidin-2-yl)piperazine-1-carbonyl)benzyl)quinazoline-2,4(1H,3H)-dione;
5-Fluoro-1-(6-fluoro-3-(4-(pyridin-2-yl)piperazine-1-carbonyl)benzyl)quinazoline-2,4(1H,3H)-dione;
5-Fluoro-1-(6-fluoro-3-(4-(thiophene-2-carbonyl)piperazine-1-carbonyl)benzyl)quinazoline-2,4(1H,3H)-dione;
1-(3-(4-(Cyclohexylcarbonyl)piperazine-1-carbonyl)-6-fluorobenzyl)-5-fluoroquinazoline-2,4(1H,3H)-dione;
1-(3-(4-(Cyclopentylcarbonyl)piperazine-1-carbonyl)-6-fluorobenzyl)-5-fluoroquinazoline-2,4(1H,3H)-dione;
5-Methyl-1-(3-(4-(pyrimidin-2-yl)piperazine-1-carbonyl)benzyl)quinazoline-2,4(1H,3H)-dione;
1-(3-(4-(Cyclopentylcarbonyl)piperazine-1-carbonyl)benzyl)-5-methylquinazoline-2,4(1H,3H)-dione;
7-Chloro-1-(3-(4-(pyrimidin-2-yl)piperazine-1-carbonyl)benzyl)quinazoline-2,4(1H,3H)-dione;
7-Chloro-1-(3-(4-(cyclopentylcarbonyl)piperazine-1-carbonyl)benzyl)quinazoline-2,4(1H,3H)-dione;
1-(3-(4-(Cyclopropylcarbonyl)piperazine-1-carbonyl)-4-fluorobenzyl)-5-fluoroquinazoline)-2,4(1H,3H)-dione;
6-Chloro-(1-(3-(4-benzoylpiperazine-1-carbonyl)-4-fluorobenzyl)quinazoline)-2,4(1H,3H)-dione;
1-(3-(4-(Cyclobutylcarbonyl)piperazine-1-carbonyl)benzyl)-5-fluoroquinazoline-2,4(1H,3H)-dione;
1-(3-(4-(Cyclobutylcarbonyl)piperazine-1-carbonyl)-4-fluorobenzyl)-5-fluoroquinazoline-2,4(1H,3H)-dione;
6-Chloro-1-(3-(4-(cyclobutylcarbonyl)piperazine-1-carbonyl)-6-fluorobenzyl)quinazoline-2,4(1H,3H)-dione;
5-Chloro-1-(3-(4-(cyclobutylcarbonyl)piperazine-1-carbonyl)-4-fluorobenzyl)quinazoline-2,4(1H,3H)-dione;
6-Chloro-1-(3-(4-(cyclobutylcarbonyl)piperazine-1-carbonyl)-4-fluorobenzyl)quinazoline-2,4(1H,3H)-dione;
5-Chloro-1-(3-(4-(cyclobutylcarbonyl)piperazine-1-carbonyl)-6-fluorobenzyl)quinazoline-2,4(1H,3H)-dione;
5-Chloro-1-(6-fluoro-3-(4-(thiophene-2-carbonyl)piperazine-1-carbonyl)benzyl)quinazoline-2,4(1H,3H)-dione;
5-Fluoro-1-(4-fluoro-3-(4-(furan-2-carbonyl)piperazine-1-carbonyl)benzyl)quinazoline-2,4(1H,3H)-dione;
5-Chloro-1-(6-fluoro-3-(4-(pyridin-2-yl)piperazine-1-carbonyl)benzyl)quinazoline-2,4(1H,3H)-dione;
6-Chloro-1-(6-fluoro-3-(4-(pyridin-2-yl)piperazine-1-carbonyl)benzyl)quinazoline-2,4(1H,3H)-dione;
6-Chloro-1-(5-fluoro-3-(4-(pyrimidin-2-yl)piperazine-1-carbonyl)benzyl)quinazoline-2,4(1H,3H)-dione;
5-Fluoro-1-(5-fluoro-3-(4-(pyrimidin-2-yl)piperazine-1-carbonyl)benzyl)quinazoline-2,4(1H,3H)-dione;
1-(3-(4-(Cyclopropylcarbonyl)piperazine-1-carbonyl)-4-fluorobenzyl)-6-fluoroquinazoline-2,4(1H,3H)-dione;
1-(3-(4-(Cyclobutylcarbonyl)piperazine-1-carbonyl)benzyl)-6-fluoroquinazoline-2,4(1H,3H)-dione;
1-(3-(4-(Cyclobutylcarbonyl)piperazine-1-carbonyl)-4-fluorobenzyl)-6-fluoroquinazoline-2,4(1H,3H)-dione;
1-(3-(4-Benzoylpiperazine-1-carbonyl)-4-fluorobenzyl)-6-fluoroquinazoline-2,4(1H,3H)-dione;
1-(3-(4-(Cyclobutylcarbonyl)piperazine-1-carbonyl)-6-fluorobenzyl)-5-fluoroquinazoline-2,4(1H,3H)-dione;
1-(3-(4-(Cyclobutylcarbonyl)piperazine-1-carbonyl)-6-fluorobenzyl)-6-fluoroquinazoline-2,4(1H,3H)-dione;
5-Fluoro-1-(6-fluoro-3-(4-(furan-2-carbonyl)piperazine-1-carbonyl)benzyl)quinazoline-2,4(1H,3H)-dione;
6-Fluoro-1-(4-fluoro-3-(4-(furan-2-carbonyl)piperazine-1-carbonyl)benzyl)quinazoline-2,4(1H,3H)-dione;
6-Fluoro-1-(5-fluoro-3-(4-(pyrimidin-2-yl)piperazine-1-carbonyl)benzyl)quinazoline-2,4(1H,3H)-dione;
1-(6-Chloro-3-(4-(pyrimidin-2-yl)piperazine-1-carbonyl)benzyl)-6-fluoroquinazoline-2,4(1H,3H)-dione;
6-Fluoro-1-(4-fluoro-3-(4-(thiazol-2-yl)piperazine-1-carbonyl)benzyl)quinazoline-2,4(1H,3H)-dione;
5-Fluoro-1-(4-fluoro-3-(4-(thiazol-2-yl)piperazine-1-carbonyl)benzyl)quinazoline-2,4(1H,3H)-dione;
5-Fluoro1-(4-fluoro-3-(4-(pyrimidin-2-yl)piperazine-1-carbonyl)benzyl)quinazoline-2,4(1H,3H)-dione hydrochloride;
6-Fluoro-1-((2-(4-(pyrimidin-2-yl)piperazine-1-carbonyl)pyridin-6-yl)methyl)quinazoline-2,4(1H,3H)-dione;
5-Fluoro-1-(4-fluoro-3-(4-methoxybenzylcarbamoyl)benzyl)quinazoline-2,4(1H,3H)-dione;
1-(3-(3-Chlorobenzylcarbamoyl)-4-fluorobenzyl)-5-fluoroquinazoline-2,4(1H,3H)-dione;
1-(3-(Benzylcarbamoyl)-4-fluorobenzyl)-5-fluoroquinazoline-2,4(1H,3H)-dione;
5-Methoxy-1-(3-(4-(pyrimidin-2-yl)piperazine-1-carbonyl)benzyl)quinazoline-2,4(1H,3H)-dione;
6-Methoxy-1-(3-(4-(pyrimidin-2-yl)piperazine-1-carbonyl)benzyl)quinazoline-2,4(1H,3H)-dione;
1-(3-(5-Bromopyrimidin-2-aminocarbamoyl)-4-fluorobenzyl)-5-fluoroquinazoline-2,4(1H,3H)-dione;
1-(3-(4-(Pyrimidin-2-yl)piperazine-1-carbonyl)benzyl)-7-(trifluoromethyl)quinazoline-2,4(1H,3H)-dione;
5-Fluoro-1-(6-methoxy-3-(4-(pyrimidin-2-yl)piperazine-1-carbonyl)benzyl)quinazoline-2,4(1H,3H)-dione;
7-Methoxy-1-(3-(4-(pyrimidin-2-yl)piperazine-1-carbonyl)benzyl)quinazoline-2,4(1H,3H)-dione;
5-Fluoro-1-(4-fluoro-3-(4-(tetrahydrofuran-2-carbonyl)piperazine-1-carbonyl)benzyl)quinazoline-2,4(1H,3H)-dione;
5-Fluoro-1-(4-nitro-3-(4-(pyrimidin-2-yl)piperazine-1-carbonyl)benzyl)quinazoline-2,4(1H,3H)-dione;
1-(3-(4-Cyclohexylpiperazine-1-carbonyl)-4-fluorobenzyl)-5-fluoroquinazoline-2,4(1H,3H)-dione;
5-Fluoro-1-(4-fluoro-3-(4-phenylpiperazine-1-carbonyl)benzyl)quinazoline-2,4(1H,3H)-dione;

5-Fluoro-1-(4-fluoro-3-(4-phenylpiperidine-1-carbonyl)benzyl)quinazoline-2,4(1H,3H)-dione;
1-(4-Bromo-3-(4-(pyrimidin-2-yl)piperazine-1-carbonyl)benzyl)-5-fluoroquinazoline-2,4(1H,3H)-dione;
6,7-Methylenedioxo-1-(3-(4-(pyrimidin-2-yl)piperazine-1-carbonyl)benzyl)quinazoline-2,4(1H,3H)-dione;
1-(3-(4-(Cyclohexylmethyl)piperazine-1-carbonyl)-4-fluorobenzyl)-5-fluoroquinazoline-2,4(1H,3H)-dione;
8-Fluoro-1-(3-(4-(pyrimidin-2-yl)piperazine-1-carbonyl)benzyl)quinazoline-2,4(1H,3H)-dione;
6-Amino-1-(3-(4-(pyrimidin-2-yl)piperazine-1-carbonyl)benzyl)quinazoline-2,4(1H,3H)-dione;
8-Chloro-1-(3-(4-(pyrimidin-2-yl)piperazine-1-carbonyl)benzyl)quinazoline-2,4(1H,3H)-dione;
8-Methyl-1-(3-(4-(pyrimidin-2-yl)piperazine-1-carbonyl)benzyl)quinazoline-2,4(1H,3H)-dione;
8-Methoxy-1-(3-(4-(pyrimidin-2-yl)piperazine-1-carbonyl)benzyl)quinazoline-2,4(1H,3H)-dione;
8-Hydroxy-1-(3-(4-(pyrimidin-2-yl)piperazine-1-carbonyl)benzyl)quinazoline-2,4(1H,3H)-dione;
1-(3-(4-(Cyclopentylcarbonyl)piperazine-1-carbonyl)-4-fluorobenzyl)quinazoline-2,4-(1H,3H)-dione;
1-(3-(4-(Cyclohexylcarbonyl)piperazine-1-carbonyl)-4-fluorobenzyl)quinazoline-2,4-(1H,3H)-dione;
1-(3-(4-(Cyclobutylcarbonyl)piperazine-1-carbonyl)-4-fluorobenzyl)quinazoline-2,4-(1H,3H)-dione;
1-(4-Fluoro-3-(4-(furan-2-carbonyl)piperazine-1-carbonyl)benzyl)quinazoline-2,4-(1H,3H)-dione;
5-Chloro-1-(3-(4-(cyclopentylcarbonyl)piperazine-1-carbonyl)-4-fluorobenzyl)quinazoline-2,4-(1H,3H)-dione;
5-Chloro-1-(3-(4-(cyclohexylcarbonyl)piperazine-1-carbonyl)-4-fluorobenzyl)quinazoline-2,4-(1H,3H)-dione;
5-Chloro-1-(4-fluoro-3-(4-(thiophene-2-carbonyl)piperazine-1-carbonyl)benzyl)quinazoline-2,4-(1H,3H)-dione;
6-Chloro-1-(4-fluoro-3-(4-(pyrimidin-2-yl)piperazine-1-carbonyl)benzyl)quinazoline-2,4-(1H,3H)-dione;
6-Chloro-1-(3-(4-(cyclopentylcarbonyl)piperazine-1-carbonyl)-4-fluorobenzyl)quinazoline-2,4-(1H,3H)-dione;
6-Chloro-1-(3-(4-(cyclohexylcarbonyl)piperazine-1-carbonyl)-4-fluorobenzyl)quinazoline-2,4-(1H,3H)-dione;
6-Chloro-1-(4-fluoro-3-(4-(thiophene-2-carbonyl)piperazine-1-carbonyl)benzyl)quinazoline-2,4-(1H,3H)-dione;
6-Chloro-1-(3-(4-(cyclopropylcarbonyl)piperazine-1-carbonyl)-4-fluorobenzyl)quinazoline-2,4-(1H,3H)-dione;
6-Chloro-1-(3-(4-(cyclopentylcarbonyl)piperazine-1-carbonyl)-6-fluorobenzyl)quinazoline-2,4-(1H,3H)-dione;
6-Chloro-1-(3-(4-(cyclohexylcarbonyl)piperazine-1-carbonyl)-6-fluorobenzyl)quinazoline-2,4-(1H,3H)-dione;
1-(3-(4-(Cyclopentylcarbonyl)piperazine-1-carbonyl)-4-fluorobenzyl)-5-fluoroquinazoline-2,4-(1H,3H)-dione;
1-(3-(4-(Cyclohexylcarbonyl)piperazine-1-carbonyl)-4-fluorobenzyl)-5-fluoroquinazoline-2,4-(1H,3H)-dione;
5-Fluoro-1-(4-fluoro-3-(4-(thiophene-2-carbonyl)piperazine-1-carbonyl)benzyl)quinazoline-2,4-(1H,3H)-dione;
1-(3-(4-(Cyclohexylcarbonyl)piperazine-1-carbonyl)-4-fluorobenzyl)-6-fluoroquinazoline-2,4-(1H,3H)-dione;
6-Fluoro-1-(6-fluoro-3-(4-(pyridin-2-yl)piperazine-1-carbonyl)benzyl)quinazoline-2,4-(1H,3H)-dione;
1-(3-(4-(Cyclopentylcarbonyl)piperazine-1-carbonyl)-6-fluorobenzyl)-6-fluoroquinazoline-2,4-(1H,3H)-dione;
5-Fluoro-1-(6-fluoro-3-(4-(pyrimidin-2-yl)piperazine-1-carbonyl)benzyl)quinazoline-2,4-(1H,3H)-dione;
5-Fluoro-1-(6-fluoro-3-(4-(pyrimidin-2-yl)piperazine-1-carbonyl)benzyl)quinazoline-2,4-(1H,3H)-dione;
1-(3-(4-(Cyclopentylcarbonyl)piperazine-1-carbonyl)-6-fluorobenzyl)-5-fluoroquinazoline-2,4-(1H,3H)-dione;
6-Chloro-1-(3-(4-benzoylpiperazine-1-carbonyl)-4-fluorobenzyl)quinazoline-2,4-(1H,3H)-dione;
1-(3-(4-(Cyclobutylcarbonyl)piperazine-1-carbonyl)-4-fluorobenzyl)-5-fluoroquinazoline-2,4-(1H,3H)-dione;
6-Chloro-1-(3-(4-(cyclobutylcarbonyl)piperazine-1-carbonyl)-6-fluorobenzyl)quinazoline-2,4-(1H,3H)-dione;
6-Chloro-1-(3-(4-(cyclobutylcarbonyl)piperazine-1-carbonyl)-4-fluorobenzyl)quinazoline-2,4-(1H,3H)-dione;
1-(3-(4-(Cyclobutylcarbonyl)piperazine-1-carbonyl)-4-fluorobenzyl)-6-fluoroquinazoline-2,4-(1H,3H)-dione;
6-Fluoro-1-(4-fluoro-3-(4-(thiazol-2-yl)piperazine-1-carbonyl)benzyl)quinazoline-2,4-(1H,3H)-dione;
1-(3-(4-(Cyclohexylmethyl)piperazine-1-carbonyl)-4-fluorobenzyl)-5-fluoroquinazoline-2,4-(1H,3H)-dione; and
8-Hydroxy-1-(3-(4-(pyrimidin-2-yl)piperazine-1-carbonyl)benzyl)quinazoline-2,4-(1H,3H)-dione;
or a pharmaceutically acceptable salt thereof;
(b) a pharmaceutically acceptable carrier; and
(c) at least one known anticancer agent, or a pharmaceutically acceptable salt of said agent.

11. The pharmaceutical composition of claim 10, wherein the anticancer agent or a pharmaceutically acceptable salt of said agent is selected from the group consisting of busulfan, melphalan, chlorambucil, cyclophosphamide, ifosfamide, temozolomide, bendamustine, cis-platin, mitomycin C, bleomycin, carboplatin, camptothecin, irinotecan, topotecan, doxorubicin, epirubicin, aclarubicin, mitoxantrone, elliptinium, etoposide, 5-azacytidine, gemcitabine, 5-fluorouracil, methotrexate, 5-fluoro-2'-deoxy-uridine, fludarabine, nelarabine, ara-C, alanosine, pralatrexate, pemetrexed, hydroxyurea, thioguanine, colchicine, vinblastine, vincristine, vinorelbine, paclitaxel, ixabepilone, cabazitaxel, docetaxel, campath, Panitumumab, Ofatumumab, Avastin, trastuzumab, rituximab, imatinib, gefitinib, erlotinib, lapatinib, sorafenib, sunitinib, nilotinib, dasatinib, pazopanib, temsirolimus, everolimus, vorinostat, romidepsin, tamoxifen, letrozole, fulvestrant, mitoguazone, octreotide, retinoic acid, arsenic trioxide, zoledronic acid, bortezomib, thalidomide and lenalidomide.

12. A method of treating cancer, comprising administering to an individual in need thereof an effective amount of the pharmaceutical composition of claim 1, wherein the cancer is melanoma, non-Hodgkin's lymphomas, breast carcinoma, ovarian carcinoma, soft-tissue sarcoma, primary brain carcinoma, small-cell lung carcinoma, stomach carcinoma, colon carcinoma, head and neck carcinoma, pancreatic carcinoma renal cell carcinoma, or prostatic carcinoma.

13. The method of claim 12, further comprising administering at least one known anticancer agent, or a pharmaceutically acceptable salt of said agent.

14. The method of claim 13, wherein the anticancer agent or a pharmaceutically acceptable salt of said agent is selected from the group consisting of busulfan, melphalan, chlorambucil, cyclophosphamide, ifosfamide, temozolomide, bendamustine, cis-platin, mitomycin C, bleomycin, carboplatin, camptothecin, irinotecan, topotecan, doxorubicin, epirubicin, aclarubicin, mitoxantrone, elliptinium, etoposide, 5-azacytidine, gemcitabine, 5-fluorouracil, methotrexate, 5-fluoro-2'-deoxy-uridine, fludarabine, nelarabine, ara-C, alanosine, pralatrexate, pemetrexed, hydroxyurea, thioguanine, colchicine, vinblastine, vincristine, vinorelbine, paclitaxel, ixabepilone, cabazitaxel, docetaxel, campath, Panitumumab, Ofatumumab, Avastin, trastuzumab, rituximab, imatinib, gefitinib, erlotinib, lapatinib, sorafenib, sunitinib, nilotinib, dasatinib, pazopanib, temsirolimus, everolimus, vorinostat, romidepsin, tamoxifen, letrozole, fulvestrant, mitoguazone, octreotide, retinoic acid, arsenic trioxide, zoledronic acid, bortezomib, thalidomide and lenalidomide.

15. The method of claim 12, further comprising treating the individual with radiation-therapy.

16. A method of treating cancer, comprising administering to an individual in need thereof a pharmaceutical composition of claim 10, wherein the cancer is melanoma, non-Hodgkin's lymphomas, breast carcinoma, ovarian carcinoma, soft-tissue sarcoma, primary brain carcinoma, small-cell lung carcinoma, stomach carcinoma, colon carcinoma, head and neck carcinoma, pancreatic carcinoma, renal cell carcinoma, or prostatic carcinoma.

17. The method of claim 16, further comprising administering at least one known anticancer agent, or a pharmaceutically acceptable salt of said agent.

18. The method of claim 17, wherein the anticancer agent or a pharmaceutically acceptable salt of said agent in the pharmaceutical composition is selected from the group consisting of busulfan, melphalan, chlorambucil, cyclophosphamide, ifosfamide, temozolomide, bendamustine, cis-platin, mitomycin C, bleomycin, carboplatin, camptothecin, irinotecan, topotecan, doxorubicin, epirubicin, aclarubicin, mitoxantrone, elliptinium, etoposide, 5-azacytidine, gemcitabine, 5-fluorouracil, methotrexate, 5-fluoro-2'-deoxy-uridine, fludarabine, nelarabine, ara-C, alanosine, pralatrexate, pemetrexed, hydroxyurea, thioguanine, colchicine, vinblastine, vincristine, vinorelbine, paclitaxel, ixabepilone, cabazitaxel, docetaxel, campath, Panitumumab, Ofatumumab, Avastin, trastuzumab, rituximab, imatinib, gefitinib, erlotinib, lapatinib, sorafenib, sunitinib, nilotinib, dasatinib, pazopanib, temsirolimus, everolimus, vorinostat, romidepsin, tamoxifen, letrozole, fulvestrant, mitoguazone, octreotide, retinoic acid, arsenic trioxide, zoledronic acid, bortezomib, thalidomide and lenalidomide.

19. The method of claim 12, wherein the cancer is responsive to the inhibition of PARP activity.

20. The method of claim 12, wherein the cancer is colon carcinoma, breast carcinoma or pancreatic carcinoma.

21. The method of claim 16, wherein the cancer is responsive to the inhibition of PARP activity.

22. The method of claim 16, wherein the cancer is colon carcinoma, breast carcinoma or pancreatic carcinoma.

* * * * *

UNITED STATES PATENT AND TRADEMARK OFFICE
CERTIFICATE OF CORRECTION

PATENT NO. : 11,358,955 B2
APPLICATION NO. : 16/415803
DATED : June 14, 2022
INVENTOR(S) : Sui Xiong Cai et al.

It is certified that error appears in the above-identified patent and that said Letters Patent is hereby corrected as shown below:

On the Title Page

Page 2, item (56) under "OTHER PUBLICATIONS," left column, Line 7, change "inpatients" to -- in patients --.
Page 3, item (56) under "OTHER PUBLICATIONS," right column, Line 7, change "PARK" to -- PARP --.

In the Specification

Column 1, Line 18, change "NAD+" to -- $NAD^+$ --.
Column 16, Line 55, change "$H_2SO_3$" to -- $H_2SO_4$ --.
Column 18, Line 54, change "MeOna" to -- MeONa --.
Column 62, Line 48, change "$CD_cOD+CDCl_3$" to -- $CD_3OD+CDCl_3$ --.

Signed and Sealed this
Twenty-fourth Day of January, 2023

Katherine Kelly Vidal
*Director of the United States Patent and Trademark Office*